(12) United States Patent
Carlsson

(10) Patent No.: US 11,868,851 B2
(45) Date of Patent: *Jan. 9, 2024

(54) SYSTEMS AND METHODS FOR PREDICTING OUTCOMES USING A PREDICTION LEARNING MODEL

(71) Applicant: SymphonyAI Sensa LLC, Menlo Park, CA (US)

(72) Inventor: Gunnar Carlsson, Stanford, CA (US)

(73) Assignee: SymphonyAI Sensa LLC, Palo Alto, CA (US)

( * ) Notice: Subject to any disclaimer, the term of this patent is extended or adjusted under 35 U.S.C. 154(b) by 682 days.

This patent is subject to a terminal disclaimer.

(21) Appl. No.: 15/068,507

(22) Filed: Mar. 11, 2016

(65) Prior Publication Data

US 2016/0267397 A1 Sep. 15, 2016

Related U.S. Application Data

(60) Provisional application No. 62/131,767, filed on Mar. 11, 2015.

(51) Int. Cl.
*G06N 20/00* (2019.01)
*G06F 11/30* (2006.01)
(Continued)

(52) U.S. Cl.
CPC ......... *G06N 20/00* (2019.01); *G06F 11/3048* (2013.01); *G06F 16/35* (2019.01);
(Continued)

(58) Field of Classification Search
CPC ...... G06N 99/005; G06N 5/025; G06N 20/00; G06F 19/00; G06F 19/3437;
(Continued)

(56) References Cited

U.S. PATENT DOCUMENTS 6,226,408 B1 * 5/2001 Sirosh ............... G06K 9/6223
382/253
7,305,373 B1 * 12/2007 Cunningham ......... G06N 5/022
706/47

(Continued)

FOREIGN PATENT DOCUMENTS

CN 103544176 B * 8/2018
WO WO-2007147166 A2 * 12/2007 ............... G06N 5/02

OTHER PUBLICATIONS

Bengio et al., "Representation Learning: A Review and New Perspectives" Mar. 7, 2013, IEEE Transactions on Pattern Analysis and Machine Intelligence, vol. 35 Issue 8, pp. 1798-1828. (Year: 2013).*

(Continued)

*Primary Examiner* — Miranda M Huang
*Assistant Examiner* — Chase P. Hinckley
(74) *Attorney, Agent, or Firm* — Ahmann Kloke LLP

(57) ABSTRACT

A method comprises receiving a network of a plurality of nodes and a plurality of edges, each of the nodes comprising members representative of at least one subset of training data points, each of the edges connecting nodes that share at least one data point, grouping the data points into a plurality of groups, each data point being a member of at least one group, creating a first transformation data set, the first transformation data set including the training data set as well as a plurality of feature subsets associated with at least one group, values of a particular data point for a particular feature subset for a particular group being based on values of the particular data point if the particular data point is a member of the particular group, and applying a machine learning model to the first transformation data set to generate a prediction model.

17 Claims, 40 Drawing Sheets

(51) Int. Cl.
| | |
|---|---|
| *G06F 16/35* | (2019.01) |
| *G06N 7/01* | (2023.01) |
| *G06N 3/04* | (2023.01) |
| G06N 5/025 | (2023.01) |
| G16H 50/50 | (2018.01) |
| G16H 50/20 | (2018.01) |
| G06F 16/75 | (2019.01) |
| G06F 16/28 | (2019.01) |
| G06F 16/45 | (2019.01) |
| G06F 16/906 | (2019.01) |
| G06F 16/55 | (2019.01) |
| G06F 16/65 | (2019.01) |
| G05B 23/02 | (2006.01) |
| G06F 18/23 | (2023.01) |
| G06F 18/2137 | (2023.01) |

(52) U.S. Cl.
CPC .............. *G06N 3/04* (2013.01); *G06N 7/01* (2023.01); *G05B 23/0281* (2013.01); *G06F 16/285* (2019.01); *G06F 16/45* (2019.01); *G06F 16/55* (2019.01); *G06F 16/65* (2019.01); *G06F 16/75* (2019.01); *G06F 16/906* (2019.01); *G06F 18/2137* (2023.01); *G06F 18/23* (2023.01); *G06N 5/025* (2013.01); *G16H 50/20* (2018.01); *G16H 50/50* (2018.01)

(58) Field of Classification Search
CPC ...... G06F 19/345; G06F 16/285; G06F 16/35; G06F 16/45; G06F 16/55; G06F 16/65; G06F 16/75; G06F 16/906; G06F 11/3048; G16H 50/20; G16H 50/50; G06K 9/6218; G06K 9/6251; G05B 23/0281
USPC ........................................................ 706/12
See application file for complete search history.

(56) References Cited

U.S. PATENT DOCUMENTS

| | | | | |
|---|---|---|---|---|
| 8,560,477 | B1* | 10/2013 | Petrov | G06N 20/00 706/46 |
| 9,135,399 | B2* | 9/2015 | Seward | G16H 50/70 |
| 9,330,138 | B1* | 5/2016 | Shankar | G06F 16/282 |
| 9,336,186 | B1* | 5/2016 | Filippova | G06F 40/151 |
| 9,355,088 | B2* | 5/2016 | Simard | G06F 40/242 |
| 9,680,915 | B2* | 6/2017 | Pradhan | G06Q 30/0255 |
| 10,120,956 | B2* | 11/2018 | Chen | G06F 16/9024 |
| 10,229,520 | B2* | 3/2019 | Muraoka | G06N 5/04 |
| 10,311,085 | B2* | 6/2019 | Rezaei | G06Q 30/0269 |
| 10,572,817 | B2* | 2/2020 | Kardes | G06F 16/9024 |
| 10,628,748 | B2* | 4/2020 | Yu | G06N 20/00 |
| 10,891,334 | B2* | 1/2021 | Koutrika | G06F 16/93 |
| 2003/0041041 | A1* | 2/2003 | Cristianini | G06K 9/6215 706/12 |
| 2005/0125474 | A1* | 6/2005 | Pednault | G06F 17/18 708/400 |
| 2005/0209785 | A1* | 9/2005 | Wells | G16H 50/20 702/19 |
| 2006/0161814 | A1* | 7/2006 | Wocke | G06K 9/6251 714/26 |
| 2007/0064627 | A1* | 3/2007 | Campos | G06K 9/6224 370/255 |
| 2009/0254314 | A1* | 10/2009 | Ivosev | G06K 9/6247 702/189 |
| 2010/0310158 | A1* | 12/2010 | Fu | G06K 9/00362 382/159 |
| 2010/0313157 | A1* | 12/2010 | Carlsson | G06F 17/30601 715/769 |
| 2011/0082670 | A1* | 4/2011 | McAuley | G06F 17/10 703/2 |
| 2011/0106735 | A1* | 5/2011 | Weston | G06K 9/6231 706/12 |
| 2012/0054129 | A1* | 3/2012 | Aggarwal | G06N 20/00 706/12 |
| 2012/0201436 | A1* | 8/2012 | Oakley | G06T 3/4053 382/128 |
| 2013/0144916 | A1* | 6/2013 | Lum | G16H 50/70 707/790 |
| 2013/0290223 | A1* | 10/2013 | Chapelle | G06N 20/00 706/12 |
| 2013/0328880 | A1* | 12/2013 | Mande | G06T 11/206 345/440 |
| 2014/0071133 | A1* | 3/2014 | Chu | G06T 11/206 345/440 |
| 2014/0143251 | A1* | 5/2014 | Wang | G06F 16/285 707/737 |
| 2014/0247973 | A1* | 9/2014 | Moussavi | G06K 9/6227 382/133 |
| 2014/0279727 | A1 | 9/2014 | Baraniuk et al. | |
| 2014/0297642 | A1* | 10/2014 | Lum | G06F 16/90328 707/737 |
| 2015/0019463 | A1* | 1/2015 | Simard | G06F 17/2785 706/12 |
| 2015/0026103 | A1* | 1/2015 | Goldschmidt | G06N 20/00 706/12 |
| 2015/0033106 | A1* | 1/2015 | Stetson | G06F 16/904 715/215 |
| 2015/0134576 | A1* | 5/2015 | Shotton | G06F 16/285 706/12 |
| 2015/0213598 | A1* | 7/2015 | Madabhushi | G06V 20/698 382/128 |
| 2015/0269230 | A1* | 9/2015 | Kardes | G06Q 50/01 707/692 |
| 2015/0269494 | A1* | 9/2015 | Kardes | G06F 16/355 706/12 |
| 2015/0332165 | A1* | 11/2015 | Mermoud | G06N 20/00 706/12 |
| 2015/0347576 | A1* | 12/2015 | Endert | G06F 16/345 707/724 |
| 2015/0379423 | A1* | 12/2015 | Dirac | G06N 20/00 706/12 |
| 2015/0379426 | A1* | 12/2015 | Steele | G06N 20/00 706/12 |
| 2015/0379429 | A1* | 12/2015 | Lee | G06N 99/005 706/11 |
| 2015/0381206 | A1* | 12/2015 | Fainzilber | H03M 13/1108 714/758 |
| 2016/0055426 | A1* | 2/2016 | Aminzadeh | G06N 7/005 706/12 |
| 2016/0078361 | A1* | 3/2016 | Brueckner | H04L 67/10 706/12 |
| 2016/0092774 | A1* | 3/2016 | Wang | G06N 5/04 706/12 |
| 2016/0171089 | A1* | 6/2016 | Richard | G06F 16/9027 707/741 |
| 2016/0210552 | A1* | 7/2016 | Kasabov | G06N 3/049 |
| 2016/0224724 | A1* | 8/2016 | Zhao | G16B 20/10 |
| 2016/0261544 | A1* | 9/2016 | Conover | H04L 67/306 |
| 2017/0091673 | A1* | 3/2017 | Gupta | G06N 5/022 |
| 2017/0169276 | A1* | 6/2017 | Againn | A61B 5/4381 |
| 2017/0231550 | A1* | 8/2017 | Do | G06T 7/11 382/128 |
| 2017/0235871 | A1* | 8/2017 | Eden | G16B 40/20 703/2 |

OTHER PUBLICATIONS

Jia et al., "Feature Mining for Hyperspectral Image Classification" Feb. 5, 2013 Proceedings of the IEEE, vol. 10, No. 3, pp. 676-697. (Year: 2013).*

Handl et al., "Feature Subset Selection in Unsupervised Learning via Multiobjective Optimization" 2006 International Journal of Computational Intelligence Research, vol. 2, No. 3, pp. 217-238. (Year: 2006).*

(56) References Cited

OTHER PUBLICATIONS

Lynch et al., "Utilizing Fused Features to Mine Unknown Clusters in Training Data" 2006. (Year: 2006).*
Wang et al., "Multi-Label Relational Neighbor Classification using Social Context Features" Aug. 11, 2013 pp. 474-472. (Year: 2013).*
Kyan et al., "The Self-Organizing Hierarchical Variance Map" 2014 Chapter from "Unsupervised Learning: A Dynamic Approach", pp. 159-1196. (Year: 2014).*
Sunderrajan, Santhoshkumar "Distributed Tracking and Re-Identification in a Camera Network" Dec. 2014, Dissertation University of California, pp. i-168. (Year: 2014).*
Rodrigues et al., "Large Graph Analysis in the GMine System" Jan. 2013, IEEE Transactions on Knowledge and Data Engineering, vol. 25, No. 1: 106-1118. (Year: 2013).*
Zhou, Minguan, "Infinite Edge Partition Models for Overlapping Community Detection and Link Prediction" Jan. 25, 2015, pp. 1-11. (Year: 2015).*
Moazzezi, Reza, "A hierarchical framework for object recognition" 2014, pp. 1-23. (Year: 2014).*
Ni et al., "Ricci Curvature of the Internet Topology" Jan. 17, 2015. (Year: 2015).*
Prat-Perez et al., "High Quality, Scalable and Parallel Community Detection for Large Real Graphs" Apr. 7-11, 2014, pp. 225-235. (Year: 2014).*
Buzun et al., "EgoLP: Fast and Distributed Community Detection in Billion-node Social Networks" 2014, IEEE, pp. 553-540. (Year: 2014).*
Duarte-Carvajalino et al., "Hierarchical topological network analysis of anatomical human brain connectivity and differences related to sex and kinship" Nov. 12, 2011, Neuroimaging, pp. 3784-3804. (Year: 2011).*
Yang et al., "Community Detection in Networks with Node Attributes" Jan. 28, 2014. (Year: 2014).*
Mussmann et al., "Incorporating Assortativity and Degree Dependence into Scalable Network Models" Feb. 9, 2015, pp. 238-246. (Year: 2015).*
Mussman et al., "Assortativity in Chung Lu Random Graph Models" Aug. 24, 2014, (Year: 2014).*
Pfeiffer et al., "Attributed Graph Models: Modeling Network Structure with Correlated Attributes" Apr. 2014, pp. 831-841. (Year: 2014.*
Fasy et al., "Introduction to the R package TDA" Jan. 29, 2015, pp. 1-16. (Year: 2015).*
Yang et al., "Structure and Overlaps of Ground-Truth Communities in Networks" Apr. 2014, pp. 1-35. (Year: 2014).*
Rabbany et al., "Generalization of Clustering Agreements and Distances for Overlapping Clusters and Network Communities" Mar. 6, 2015, pp. 1-24. (Year: 2015).*
Ciglan et al., "On Community Detection in Real-World Networks and the Importance of Degree Assortativity" Aug. 2013, pp. 1007-1015. (Year: 2013).*
Bothorel et al., "Clustering attributed graphs: models, measures, and methods*" Jan. 7, 2015, pp. 1-22. (Year: 2015).*
Parimala et al., "Graph Clustering Based on Structural Attribute Neighborhood Similarity (SANS)" Mar. 5, 2015. (Year: 2015).*
Shao et al., "Community Detection via Local Dynamic Interaction" Sep. 29, 2014. (Year: 2014).*
Xu et al., "GBAGC: A General Bayesian Framework for Attributed Graph Clustering" Aug. 2014, pp. 1-43. (Year: 2014).*
Kwashie et al., "Mining Differential Dependencies: A Subspace Clustering Approach" 2014, pp. 50-61. (Year: 2014).*
Bauer et al., "Measuring Distance between Reeb Graphs" Jun. 2014, pp. 464-473. (Year: 2014).*
Lecci et al., "Statistical Analysis of Metric Graph Reconstruction" Oct. 2014, pp. 3425-3446. (Year: 2014).*
Wu et al., "Robust Local Community Detection: On Free Rider Effect and Its Elimination" Feb. 2015, pp. 798-809. (Year: 2015).*
Peng et al., "Accelerating Community Detection by Using K-core Subgraphs" Oct. 13, 2014. (Year: 2014).*
Silva et al., "On the Modular Dynamics of Financial Market Networks" Jan. 22, 2015, arXiv: 1501.05040v2, pp. 1-14. (Year: 2015).*
Chazal et al., "Robust Topological Inference: Distance to a Measure and Kernel Distance" Dec. 22, 2014, arXiv: 1412.7197v1, pp. 1-32. (Year: 2014).*
Bubenik, Peter "Statistical Topological Data Analysis using Persistence Landscapes" Jan. 23, 2015, arXiv: 1207.6437v4, pp. 1-26. (Year: 2015).*
Ye et al., "Entropic Graph Embedding via Multivariate Degree Distributions" Aug. 2014. (Year: 2014).*
Kardes et al., "Graph Based Induction of unresponsive routers in Internet topologies" Feb. 23, 2015, pp. 178-200. (Year: 2015).*
Carlsson et al., "Topological Data Analysis and Machine Learning Theory" Oct. 2012, pp. 1-11. (Year: 2012).*
Reininghaus et al., "A Stable Multi-Scale Kernel for Topological Machine Learning" Dec. 21, 2014, pp. 1-12. (Year: 2014).*
Yi et Gesbert, "Topological Interference Management with Transmitter Cooperation" Dec. 2, 2014, pp. 1-46. (Year: 2014).*
International Application No. PCT/US2016/022224, International Search Report and Written Opinion dated Jul. 7, 2016.
European Patent Application No. 16762687.8, Search Report dated Oct. 24, 2018.

* cited by examiner

| Patient ID | Gene 1 Expression | Gene 2 Expression | ... | Gene y Expression | Clinical Outcome |
|---|---|---|---|---|---|
| P1 | G1a | G2a | | Gya | Outcome P1 |
| P2 | G1b | G2b | | Gyb | Outcome P2 |
| P3 | G1c | G2c | | Gyc | Outcome P3 |
| ● | ● | ● | | ● | ● |
| ● | ● | ● | | ● | ● |
| ● | ● | ● | | ● | ● |
| Pn | G1n | G2n | | Gyn | Outcome Pn |

| Date | Equity Indices | | | Commodities | | Currencies | | | Fixed Income | |
|---|---|---|---|---|---|---|---|---|---|---|
| | SPX_Ret_1 | SPX_Ret_5 | Nikkei_VolChg_20 | ... | CRUDE_Rtn_200 CORN_VolChg_5 | ... | USDCHF_Rtn_50 USDCAD_Rtn_80 | ... | Corp_AAA_Chg_1 3Yr_UST_Chg_200 |
| 1/2/03 | 3.0% | 2.1% | -16.0% | | | | | | | |
| 1/3/03 | -0.1% | | | | | | | | | |
| 1/6/03 | | | | | | | | | | |
| ... | | | | | | | | | | |
| 11/27/13 | | | | | | | | | | |
| 11/28/13 | | | | | | | | | | |

- Number of rows: 2600, representing 10+ years of daily trading data
- Number of columns: 300 derived features

FIG. 34

| Testing Date | Similar Dates | | | | | | | | |
|---|---|---|---|---|---|---|---|---|---|
| 12/2/13 | 6/2/03 | 12/23/11 | 4/30/03 | 5/1/03 | 5/5/03 | 5/6/03 | 5/7/03 | 5/8/03 | 5/9/03 | 5/12/03 |
| 12/3/13 | 4/6/12 | 12/13/11 | 12/15/11 | 12/19/11 | 10/17/11 | 3/26/03 | 3/27/03 | 3/28/03 | 3/31/03 | 4/1/03 |
| 12/4/13 | 12/13/11 | 12/15/11 | 12/19/11 | 3/26/03 | 3/27/03 | 3/28/03 | 3/31/03 | 4/1/03 | 4/2/03 | 4/3/03 |
| 12/5/13 | 12/14/11 | 3/25/03 | 3/26/03 | 3/27/03 | 3/28/03 | 3/31/03 | 4/1/03 | 4/2/03 | 4/3/03 | 4/4/03 |
| 12/6/13 | 1/2/03 | 1/3/03 | 1/6/03 | 1/7/03 | 1/13/03 | 6/21/10 | 6/28/10 | 2/17/03 | 3/11/03 | 3/13/03 |
| 12/9/13 | 12/13/11 | 12/14/11 | 12/15/11 | 12/19/11 | 12/23/11 | 4/16/03 | 4/21/03 | 4/22/03 | 4/23/03 | 4/24/03 |
| 12/10/13 | 12/13/11 | 12/14/11 | 12/15/11 | 12/19/11 | 12/23/11 | 4/16/03 | 4/21/03 | 4/22/03 | 4/23/03 | 4/24/03 |
| 12/11/13 | 12/31/02 | 1/17/03 | 12/25/07 | 1/28/03 | 1/30/03 | 1/31/03 | 2/3/03 | 2/4/03 | 2/5/03 | 2/6/03 |
| 12/12/13 | 12/31/02 | 1/2/03 | 1/3/03 | 1/6/03 | 1/7/03 | 1/13/03 | 2/3/03 | 12/25/07 | 1/30/03 | 1/31/03 |
| 12/13/13 | 12/31/02 | 1/2/03 | 1/3/03 | 1/6/03 | 1/7/03 | 1/8/03 | 1/9/03 | 1/10/03 | 1/13/03 | 1/14/03 |
| 12/16/13 | 12/31/02 | 1/2/03 | 1/3/03 | 1/6/03 | 1/7/03 | 1/13/03 | 1/20/03 | 1/21/03 | 1/22/03 | 1/23/03 |
| 12/17/13 | 12/31/02 | 1/2/03 | 12/26/11 | 1/6/03 | 1/7/03 | 2/21/03 | 3/4/09 | 2/17/03 | 1/13/03 | 4/9/04 |
| 12/18/13 | 12/31/02 | 1/2/03 | 1/3/03 | 1/6/03 | 1/7/03 | 1/13/03 | 12/25/07 | 6/16/10 | 6/17/10 | 6/21/10 |
| 12/19/13 | 12/31/02 | 1/2/03 | 1/3/03 | 1/6/03 | 1/7/03 | 1/13/03 | 12/25/07 | 6/16/10 | 6/17/10 | 6/21/10 |
| 12/20/13 | 12/31/02 | 1/2/03 | 1/3/03 | 1/6/03 | 1/7/03 | 1/13/03 | 12/25/07 | 6/16/10 | 6/17/10 | 6/21/10 |

FIG. 37

SYSTEMS AND METHODS FOR PREDICTING OUTCOMES USING A PREDICTION LEARNING MODEL

CROSS REFERENCE TO RELATED APPLICATIONS

This application claims priority to U.S. Provisional Patent Application Ser. No. 62/131,767, filed Mar. 11, 2015 and entitled "TDA Prediction," which is hereby incorporated by reference herein.

BACKGROUND

1. Field of the Invention

Embodiments of the present invention(s) are directed to grouping of data points for data analysis and more particularly to generating a graph utilizing improved groupings of data points based on scores of the groupings.

2. Related Art

As the collection and storage of data has increased, there is an increased need to analyze and make sense of large amounts of data. Examples of large datasets may be found in financial services companies, oil expiration, biotech, and academia. Unfortunately, previous methods of analysis of large multidimensional datasets tend to be insufficient (if possible at all) to identify important relationships and may be computationally inefficient.

In one example, previous methods of analysis often use clustering. Clustering is often too blunt an instrument to identify important relationships in the data. Similarly, previous methods of linear regression, projection pursuit, principal component analysis, and multidimensional scaling often do not reveal important relationships. Existing linear algebraic and analytic methods are too sensitive to large scale distances and, as a result, lose detail.

Further, even if the data is analyzed, sophisticated experts are often necessary to interpret and understand the output of previous methods. Although some previous methods allow graphs depicting some relationships in the data, the graphs are not interactive and require considerable time for a team of such experts to understand the relationships. Further, the output of previous methods does not allow for exploratory data analysis where the analysis can be quickly modified to discover new relationships. Rather, previous methods require the formulation of a hypothesis before testing.

SUMMARY OF THE INVENTION(S)

Systems and methods for predicting outcomes using a prediction learning model is described herein. In one example, a non-transitory computer readable medium includes executable instructions. The instructions are executable by a processor to perform a method. The method comprises receiving a network of a plurality of nodes and a plurality of edges, each of the nodes of the plurality of nodes comprising members representative of at least one subset of training data points, each of the edges of the plurality of edges connecting nodes that share at least one data point of the training data points, the training data set including rows and columns, each row defining a data point of the training data set and each column defining a feature, the training data set including an initial number of columns, each column including values associated with a feature of a plurality of features, grouping the data points of the training data set into a plurality of groups, each group of the plurality of groups including a different subset of data points of the training data set, each data point of the training data set being a member of at least one group of the plurality of groups, creating a first transformation data set, the first transformation data set including the training data set as well as a plurality of feature subsets, each of the plurality of feature subsets being associated with at least one group of the plurality of groups, values of a particular data point for a particular feature subset for a particular group being based on values of the particular data point in the training data set if the particular data point is a member of the particular group, and applying a machine learning model to the first transformation data set to generate a prediction model.

The method may further comprise receiving an analysis data set, grouping data points of the analysis data set into one or more groups of the plurality of groups, creating a second transformation data set, the second transformation data set including the analysis data set as well as the plurality of feature subsets, each of the plurality of feature subsets being associated with the at least one group of the plurality of groups, values of a particular data point of the analysis data set for a particular feature subset for a particular group being based on values of the particular data point in the analysis data set if the particular data point is a member of the particular group, applying the prediction model to the second transformation data set to generate predicted outcomes, and generating a report indicating one or more of the predicted outcomes.

In some embodiments, the method may further comprise comparing the predicted outcomes to known outcomes to assess the quality of the prediction model.

The network of the plurality of nodes and the plurality of edges may be a result of topological data analysis applied to the training data set. The network of the plurality of nodes and the plurality of edges are generated by receiving the training data set, generating a reference space, mapping the data points of the training data into the reference space using at least one filter, generating a cover based on a resolution, clustering data in the cover based on a metric and data points of the training data set, identifying nodes based on the clustered data, and identifying edges between nodes if nodes share member data points from the training data set. The method of generating the plurality of nodes and the plurality of edges may be performed, at least partially, on the same processor(s) that performs the grouping of data points, creation of the first transformation data set, and/or the application of the machine learning model.

In various embodiments, values of a particular data point for a particular feature subset for a particular group are zero if the particular data point of the training data set is not a member of the particular group. In some embodiments, the values of a particular data point for a particular feature subset for a particular group are null if the particular data point of the training data set is not a member of the particular group. The values of a particular data point for a particular feature subset for a particular group of which the particular data point may be a member are weighted. Weighting of the values for the particular data point may at least partially depend on how many the plurality of groups the particular data point is a member of.

The machine learning model may be selected from a group consisting of a linear regression machine learning model, a polynomial regression machine learning model, a logistic regression machine learning model, and a random forest machine learning model.

An example method comprises receiving a network of a plurality of nodes and a plurality of edges, each of the nodes of the plurality of nodes comprising members representative of at least one subset of training data points, each of the edges of the plurality of edges connecting nodes that share at least one data point of the training data points, the training data set including rows and columns, each row defining a data point of the training data set and each column defining a feature, the training data set including an initial number of columns, each column including values associated with a feature of a plurality of features, grouping the data points of the training data set into a plurality of groups, each group of the plurality of groups including a different subset of data points of the training data set, each data point of the training data set being a member of at least one group of the plurality of groups, creating a first transformation data set, the first transformation data set including the training data set as well as a plurality of feature subsets, each of the plurality of feature subsets being associated with at least one group of the plurality of groups, values of a particular data point for a particular feature subset for a particular group being based on values of the particular data point in the training data set if the particular data point is a member of the particular group, and applying a machine learning model to the first transformation data set to generate a prediction model.

An example system may comprise a processor and memory. The memory may store instructions that, when executed by the processor, cause the processor to receive a network of a plurality of nodes and a plurality of edges, each of the nodes of the plurality of nodes comprising members representative of at least one subset of training data points, each of the edges of the plurality of edges connecting nodes that share at least one data point of the training data points, the training data set including rows and columns, each row defining a data point of the training data set and each column defining a feature, the training data set including an initial number of columns, each column including values associated with a feature of a plurality of features, group the data points of the training data set into a plurality of groups, each group of the plurality of groups including a different subset of data points of the training data set, each data point of the training data set being a member of at least one group of the plurality of groups; create a first transformation data set, the first transformation data set including the training data set as well as a plurality of feature subsets, each of the plurality of feature subsets being associated with at least one group of the plurality of groups, values of a particular data point for a particular feature subset for a particular group being based on values of the particular data point in the training data set if the particular data point is a member of the particular group, and apply a machine learning model to the first transformation data set to generate a prediction model.

The instructions may further cause the processor to receive an analysis data set, group data points of the analysis data set into one or more groups of the plurality of groups, create a second transformation data set, the second transformation data set including the analysis data set as well as the plurality of feature subsets, each of the plurality of feature subsets being associated with the at least one group of the plurality of groups, values of a particular data point of the analysis data set for a particular feature subset for a particular group being based on values of the particular data point in the analysis data set if the particular data point is a member of the particular group, apply the prediction model to the second transformation data set to generate predicted outcomes, and generate a report indicating one or more of the predicted outcomes.

BRIEF DESCRIPTION OF THE DRAWINGS

FIG. 13 is an example data structure including biological data for a number of patients that may be used to generate the cancer map visualization in some embodiments.

FIG. 24 is an example report of an autogrouped graph of data points that depicts the grouped data in some embodiments.

FIG. 34 depicts an example of structure of financial data.

FIG. 37 depicts groupings of financial data based on similar dates in this example.

DETAILED DESCRIPTION OF THE DRAWINGS

Some embodiments described herein may be a part of the subject of Topological Data Analysis (TDA). TDA is an area of research which has produced methods for studying point cloud data sets from a geometric point of view. Other data analysis techniques use "approximation by models" of various types. For example, regression methods model the data as the graph of a function in one or more variables. Unfortunately, certain qualitative properties (which one can readily observe when the data is two-dimensional) may be of a great deal of importance for understanding, and these features may not be readily represented within such models.

Figure 1A:
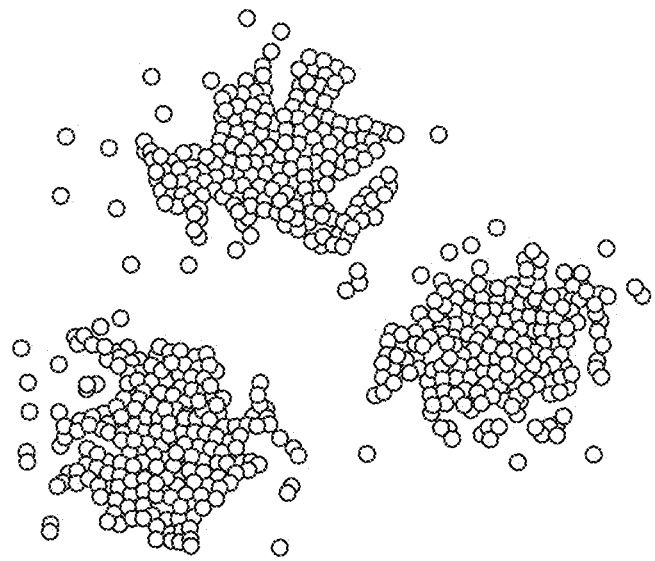
FIG. 1a is an example graph representing data that appears to be divided into three disconnected groups.

FIG. 1a is an example graph representing data that appears to be divided into three disconnected groups. In this example, the data for this graph may be associated with various physical characteristics related to different population groups or biomedical data related to different forms of a disease. Seeing that the data breaks into groups in this fashion can give insight into the data, once one understands what characterizes the groups.

Figure 1B:
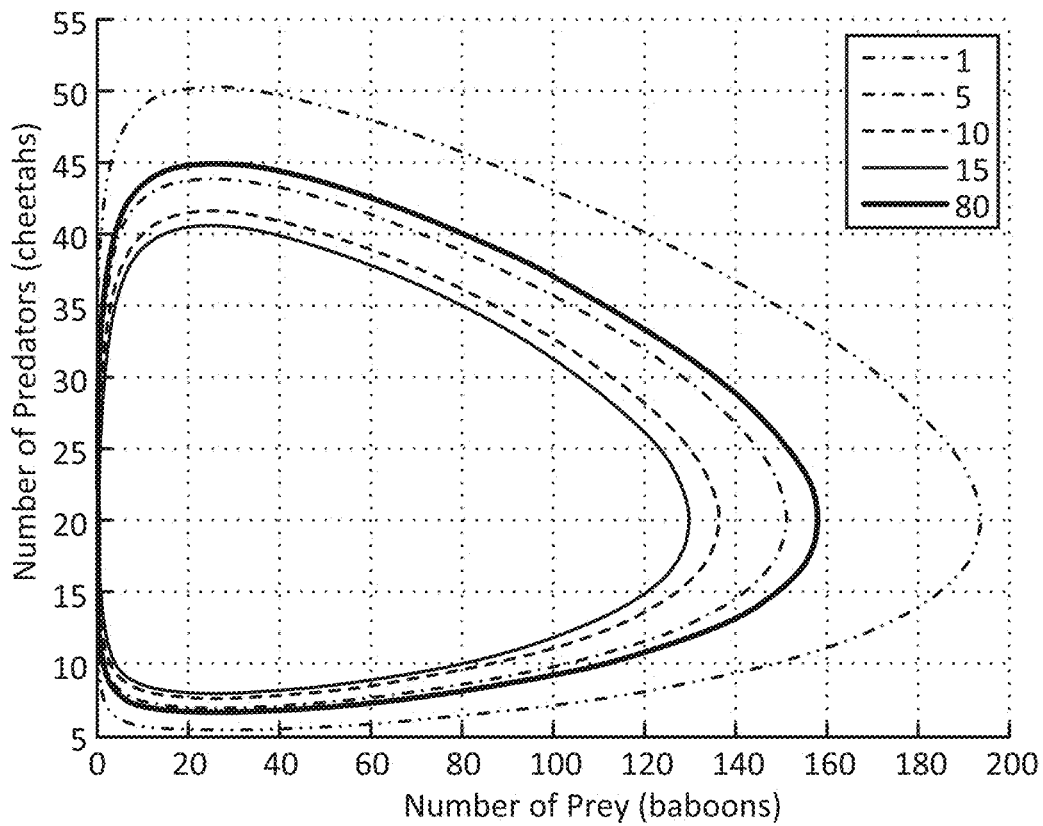
FIG. 1b is an example graph representing data set obtained from a Lotka-Volterra equation modeling the populations of predators and prey over time.

FIG. 1b is an example graph representing data set obtained from a Lotka-Volterra equation modeling the populations of predators and prey over time. From FIG. 1b, one observation about this data is that it is arranged in a loop. The loop is not exactly circular, but it is topologically a circle. The exact form of the equations, while interesting, may not be of as much importance as this qualitative observation which reflects the fact that the underlying phenomenon is recurrent or periodic. When looking for periodic or recurrent phenomena, methods may be developed which can detect the presence of loops without defining explicit models. For example, periodicity may be detectable without having to first develop a fully accurate model of the dynamics.

Figure 1C:
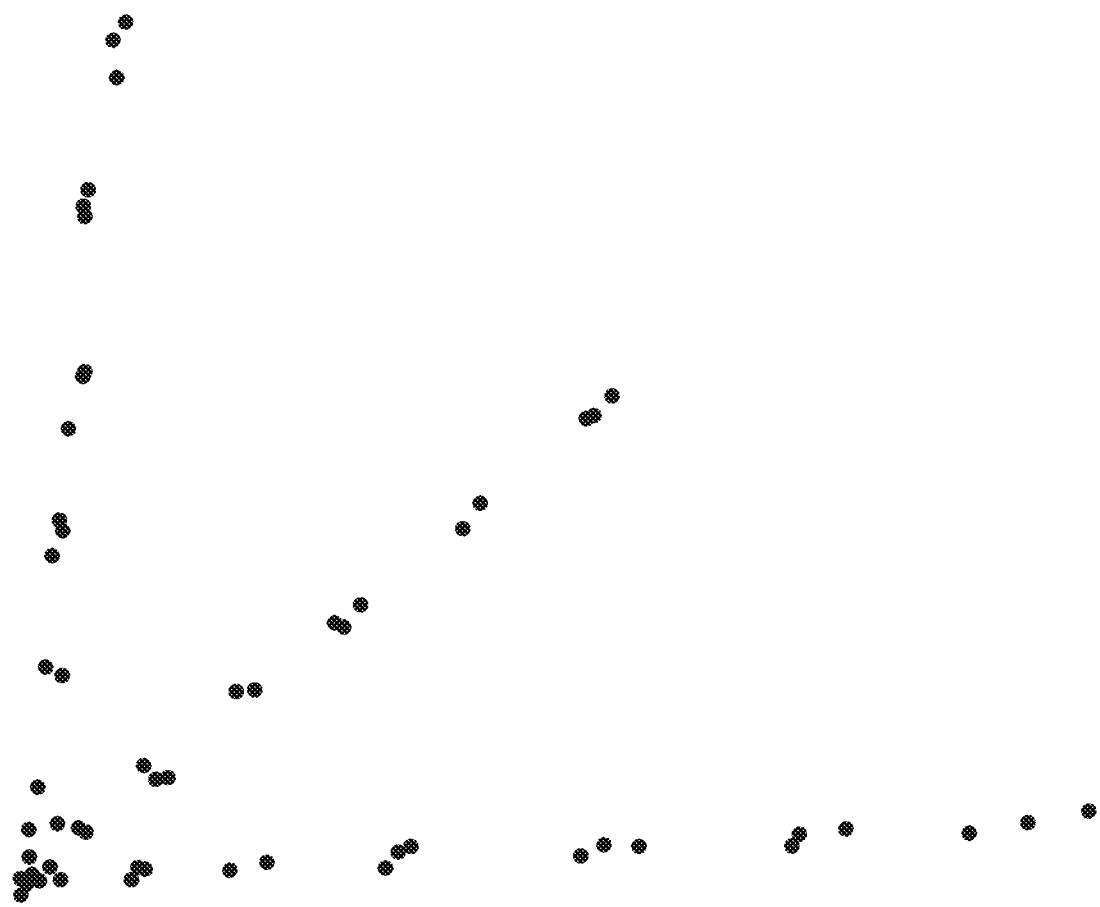
FIG. 1c is an example graph of data sets whereby the data does not break up into disconnected groups, but instead has a structure in which there are lines (or flares) emanating from a central group.

FIG. 1c is an example graph of data sets whereby the data does not break up into disconnected groups, but instead has a structure in which there are lines (or flares) emanating from a central group. In this case, the data also suggests the presence of three distinct groups, but the connectedness of the data does not reflect this. This particular data that is the basis for the example graph in FIG. 1c arises from a study of single nucleotide polymorphisms (SNPs).

In each of the examples above, aspects of the shape of the data are relevant in reflecting information about the data. Connectedness (the simplest property of shape) reflects the presence of a discrete classification of the data into disparate groups. The presence of loops, another simple aspect of shape, often reflect periodic or recurrent behavior. Finally, in the third example, the shape containing flares suggests a classification of the data descriptive of ways in which phenomena can deviate from the norm, which would typically be represented by the central core. These examples support the idea that the shape of data (suitably defined) is an important aspect of its structure, and that it is therefore important to develop methods for analyzing and understanding its shape. The part of mathematics which concerns itself with the study of shape is called topology, and topological data analysis attempts to adapt methods for studying shape which have been developed in pure mathematics to the study of the shape of data, suitably defined.

One question is how notions of geometry or shape are translated into information about point clouds, which are, after all, finite sets? What we mean by shape or geometry can come from a dissimilarity function or metric (e.g., a non-negative, symmetric, real-valued function don the set of pairs of points in the data set which may also satisfy the triangle inequality, and $d(x; y)=0$ if and only if $x=y$). Such functions exist in profusion for many data sets. For example, when the data comes in the form of a numerical matrix, where the rows correspond to the data points and the columns are the fields describing the data, the n-dimensional Euclidean distance function is natural when there are n fields. Similarly, in this example, there are Pearson correlation distances, cosine distances, and other choices.

When the data is not Euclidean, for example if one is considering genomic sequences, various notions of distance may be defined using measures of similarity based on Basic Local Alignment Search Tool (BLAST) type similarity scores. Further, a measure of similarity can come in non-numeric forms, such as social networks of friends or similarities of hobbies, buying patterns, tweeting, and/or professional interests. In any of these ways the notion of shape may be formulated via the establishment of a useful notion of similarity of data points.

One of the advantages of TDA is that it may depend on nothing more than such a notion, which is a very primitive or low-level model. It may rely on many fewer assumptions than standard linear or algebraic models, for example. Further, the methodology may provide new ways of visualizing and compressing data sets, which facilitate understanding and monitoring data. The methodology may enable study of interrelationships among disparate data sets and/or multiscale/multiresolution study of data sets. Moreover, the methodology may enable interactivity in the analysis of data, using point and click methods.

TDA may be a very useful complement to more traditional methods, such as Principal Component Analysis (PCA), multidimensional scaling, and hierarchical clustering. These existing methods are often quite useful, but suffer from significant limitations. PCA, for example, is an essentially linear procedure and there are therefore limits to its utility in highly non-linear situations. Multidimensional scaling is a method which is not intrinsically linear, but can in many situations wash out detail, since it may overweight large distances. In addition, when metrics do not satisfy an intrinsic flatness condition, it may have difficulty in faithfully representing the data. Hierarchical clustering does exhibit multiscale behavior, but represents data only as disjoint clusters, rather than retaining any of the geometry of the data set. In all four cases, these limitations matter for many varied kinds of data.

We now summarize example properties of an example construction, in some embodiments, which may be used for representing the shape of data sets in a useful, understandable fashion as a finite graph:

- The input may be a collection of data points equipped in some way with a distance or dissimilarity function, or other description. This can be given implicitly when the data is in the form of a matrix, or explicitly as a matrix of distances or even the generating edges of a mathematical network.
- One construction may also use one or more lens functions (i.e. real valued functions on the data). Lens function(s) may depend directly on the metric. For example, lens function(s) might be the result of a density estimator or a measure of centrality or data depth. Lens function(s) may, in some embodiments, depend on a particular representation of the data, as when one uses the first one or two coordinates of a principal component or multidimensional scaling analysis. In some embodiments, the lens function(s) may be columns which expert knowledge identifies as being intrinsically interesting, as in cholesterol levels and BMI in a study of heart disease.
- In some embodiments, the construction may depend on a choice of two or more processing parameters, resolution, and gain. Increase in resolution typically results in more nodes and an increase in the gain increases the number of edges in a visualization and/or graph in a reference space as further described herein.
- The output may be, for example, a visualization (e.g., a display of connected nodes or "network") or simplicial complex. One specific combinatorial formulation in one embodiment may be that the vertices form a finite set, and then the additional structure may be a collection of edges (unordered pairs of vertices) which are pictured as connections in this network.

In various embodiments, a system for handling, analyzing, and visualizing data using drag and drop methods as opposed to text based methods is described herein. Philosophically, data analytic tools are not necessarily regarded as "solvers," but rather as tools for interacting with data. For example, data analysis may consist of several iterations of a process in which computational tools point to regions of interest in a data set. The data set may then be examined by people with domain expertise concerning the data, and the data set may then be subjected to further computational analysis. In some embodiments, methods described herein provide for going back and forth between mathematical constructs, including interactive visualizations (e.g., graphs), on the one hand and data on the other.

In one example of data analysis in some embodiments described herein, an example clustering tool is discussed which may be more powerful than existing technology, in that one can find structure within clusters and study how clusters change over a period of time or over a change of scale or resolution.

An example interactive visualization tool (e.g., a visualization module which is further described herein) may produce combinatorial output in the form of a graph which can be readily visualized. In some embodiments, the example interactive visualization tool may be less sensitive to changes in notions of distance than current methods, such as multidimensional scaling.

Some embodiments described herein permit manipulation of the data from a visualization. For example, portions of the data which are deemed to be interesting from the visualization can be selected and converted into database objects, which can then be further analyzed. Some embodiments described herein permit the location of data points of interest within the visualization, so that the connection between a given visualization and the information the visualization represents may be readily understood.

Figure 2:
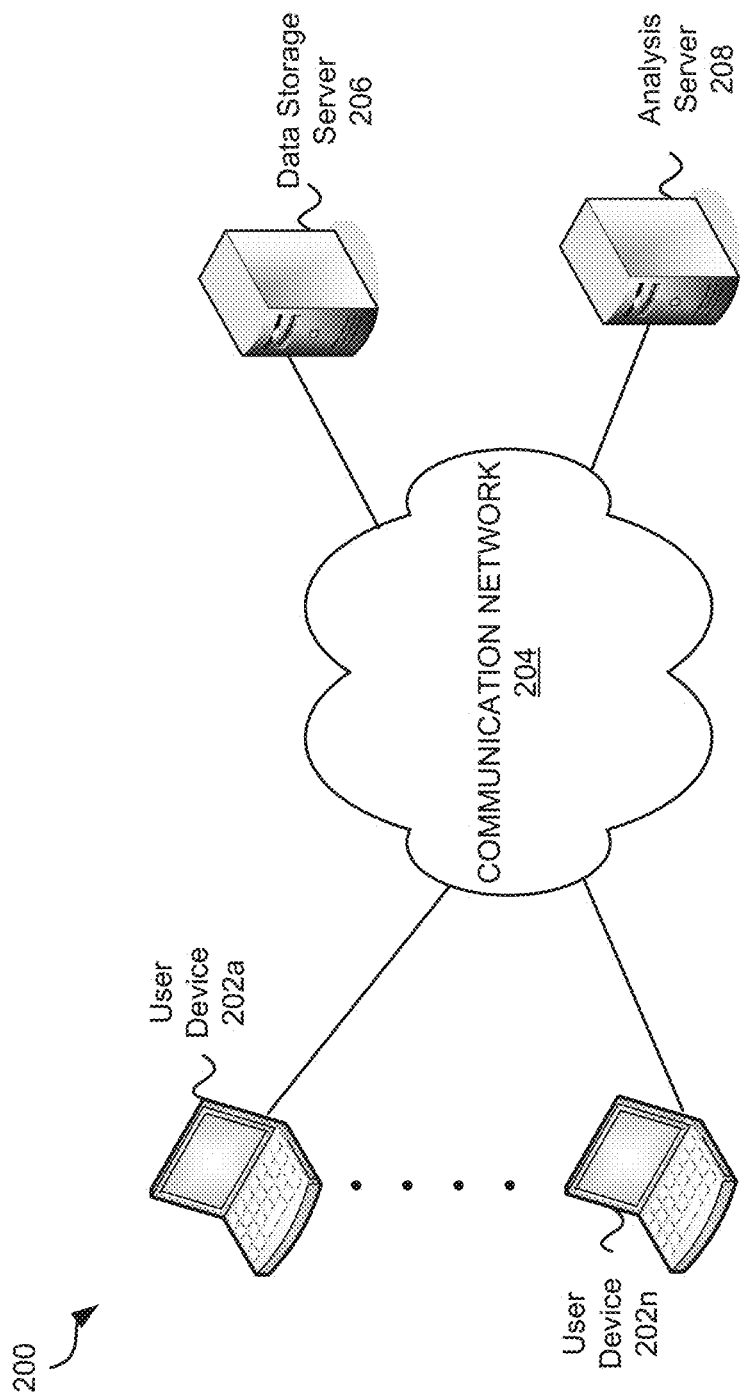
FIG. 2 is an example environment in which embodiments may be practiced.

FIG. 2 is an example environment 200 in which embodiments may be practiced. In various embodiments, data analysis and interactive visualization may be performed locally (e.g., with software and/or hardware on a local digital device), across a network (e.g., via cloud computing), or a combination of both. In many of these embodiments, a data structure is accessed to obtain the data for the analysis, the analysis is performed based on properties and parameters selected by a user, and an interactive visualization is generated and displayed. There are many advantages between performing all or some activities locally and many advantages of performing all or some activities over a network.

Environment 200 comprises user devices 202a-202n, a communication network 204, data storage server 206, and analysis server 208. Environment 200 depicts an embodiment wherein functions are performed across a network. In this example, the user(s) may take advantage of cloud computing by storing data in a data storage server 206 over a communication network 204. The analysis server 208 may perform analysis and generation of an interactive visualization.

User devices 202a-202n may be any digital devices. A digital device is any device that comprises memory and a processor. Digital devices are further described in FIG. 2. The user devices 202a-202n may be any kind of digital device that may be used to access, analyze and/or view data including, but not limited to a desktop computer, laptop, notebook, or other computing device.

In various embodiments, a user, such as a data analyst, may generate a database or other data structure with the user device 202a to be saved to the data storage server 206. The user device 202a may communicate with the analysis server 208 via the communication network 204 to perform analysis, examination, and visualization of data within the database.

The user device 202a may comprise a client program for interacting with one or more applications on the analysis server 208. In other embodiments, the user device 202a may communicate with the analysis server 208 using a browser or other standard program. In various embodiments, the user device 202a communicates with the analysis server 208 via a virtual private network. It will be appreciated that that communication between the user device 202a, the data storage server 206, and/or the analysis server 208 may be encrypted or otherwise secured.

The communication network 204 may be any network that allows digital devices to communicate. The communication network 204 may be the Internet and/or include LAN and WANs. The communication network 204 may support wireless and/or wired communication.

The data storage server 206 is a digital device that is configured to store data. In various embodiments, the data storage server 206 stores databases and/or other data structures. The data storage server 206 may be a single server or a combination of servers. In one example the data storage server 206 may be a secure server wherein a user may store data over a secured connection (e.g., via https). The data may be encrypted and backed-up. In some embodiments, the data storage server 206 is operated by a third-party such as Amazon's S3 service.

The database or other data structure may comprise large high-dimensional datasets. These datasets are traditionally very difficult to analyze and, as a result, relationships within the data may not be identifiable using previous methods. Further, previous methods may be computationally inefficient.

The analysis server 208 is a digital device that may be configured to analyze data. In various embodiments, the analysis server may perform many functions to interpret, examine, analyze, and display data and/or relationships within data. In some embodiments, the analysis server 208 performs, at least in part, topological analysis of large datasets applying metrics, filters, and resolution parameters chosen by the user. The analysis is further discussed in FIG. 8 herein.

The analysis server 208 may generate an interactive visualization of the output of the analysis. The interactive visualization allows the user to observe and explore relationships in the data. In various embodiments, the interactive visualization allows the user to select nodes comprising data that has been clustered. The user may then access the underlying data, perform further analysis (e.g., statistical analysis) on the underlying data, and manually reorient the graph(s) (e.g., structures of nodes and edges described herein) within the interactive visualization. The analysis server 208 may also allow for the user to interact with the data, see the graphic result. The interactive visualization is further discussed in FIGS. 9-11.

In some embodiments, the analysis server 208 interacts with the user device(s) 202*a*-202*n* over a private and/or secure communication network. The user device 202*a* may comprise a client program that allows the user to interact with the data storage server 206, the analysis server 208, another user device (e.g., user device 202*n*), a database, and/or an analysis application executed on the analysis server 208.

Those skilled in the art will appreciate that all or part of the data analysis may occur at the user device 202*a*. Further, all or part of the interaction with the visualization (e.g., graphic) may be performed on the user device 202*a*.

Although two user devices 202*a* and 202*n* are depicted, those skilled in the art will appreciate that there may be any number of user devices in any location (e.g., remote from each other). Similarly, there may be any number of communication networks, data storage servers, and analysis servers.

Cloud computing may allow for greater access to large datasets (e.g., via a commercial storage service) over a faster connection. Further, it will be appreciated that services and computing resources offered to the user(s) may be scalable.

Figure 3:
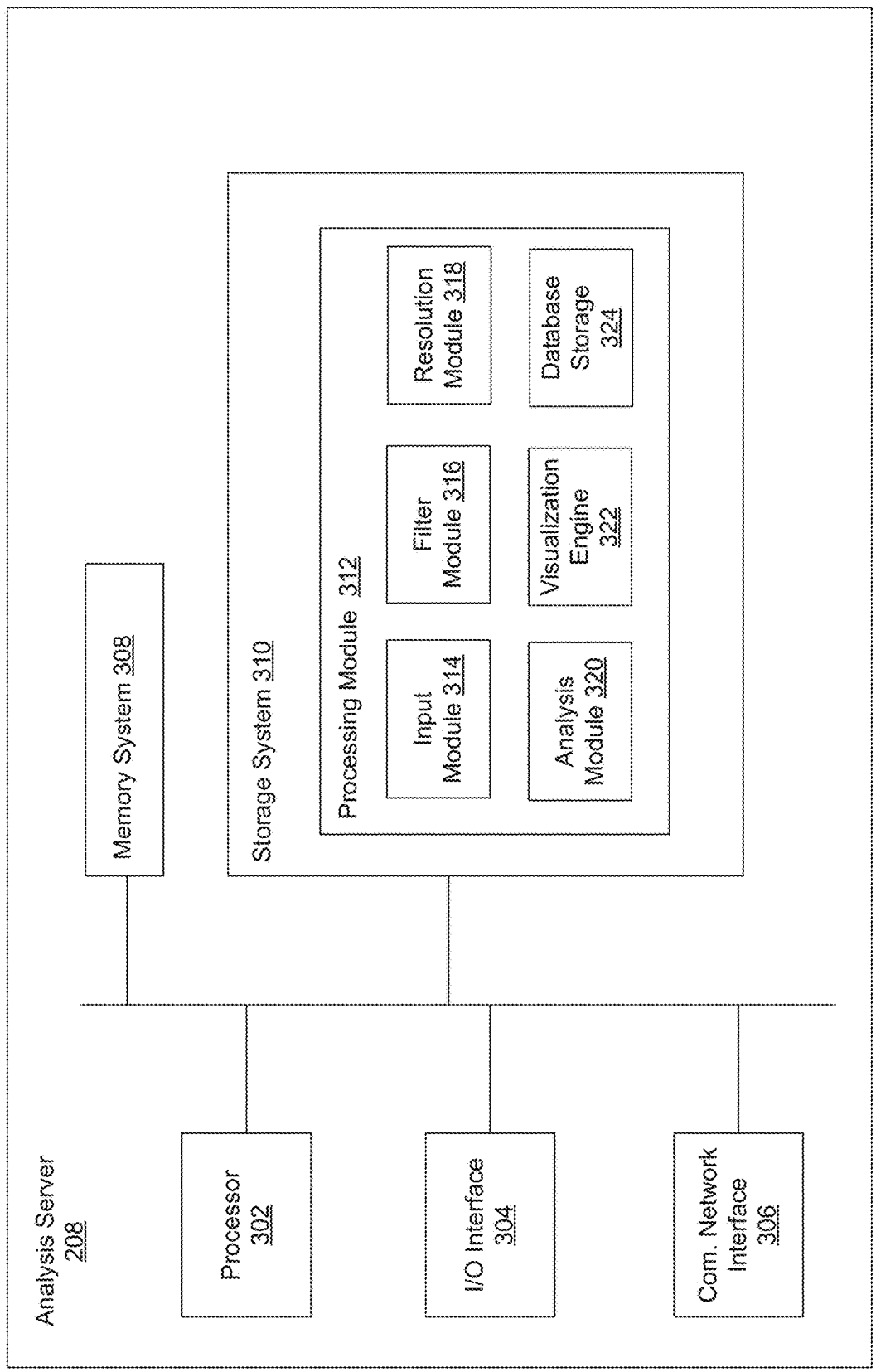
FIG. 3 is a block diagram of an example analysis server.

FIG. 3 is a block diagram of an example analysis server 208. In example embodiments, the analysis server 208 comprises a processor 302, input/output (I/O) interface 304, a communication network interface 306, a memory system 308, a storage system 310, and a processing module 312. The processor 302 may comprise any processor or combination of processors with one or more cores.

The input/output (I/O) interface 304 may comprise interfaces for various I/O devices such as, for example, a keyboard, mouse, and display device. The example communication network interface 306 is configured to allow the analysis server 208 to communication with the communication network 204 (see FIG. 2). The communication network interface 306 may support communication over an Ethernet connection, a serial connection, a parallel connection, and/or an ATA connection. The communication network interface 306 may also support wireless communication (e.g., 802.11 a/b/g/n, WiMax, LTE, WiFi). It will be apparent to those skilled in the art that the communication network interface 306 can support many wired and wireless standards.

The memory system 308 may be any kind of memory including RAM, ROM, or flash, cache, virtual memory, etc. In various embodiments, working data is stored within the memory system 308. The data within the memory system 308 may be cleared or ultimately transferred to the storage system 310.

The storage system 310 includes any storage configured to retrieve and store data. Some examples of the storage system 310 include flash drives, hard drives, optical drives, and/or magnetic tape. Each of the memory system 308 and the storage system 310 comprises a computer-readable medium, which stores instructions (e.g., software programs) executable by processor 302.

The storage system 310 comprises a plurality of modules utilized by embodiments of discussed herein. A module may be hardware, software (e.g., including instructions executable by a processor), or a combination of both. In one embodiment, the storage system 310 comprises a processing module 312 which comprises an input module 314, a filter module 316, a resolution module 318, an analysis module 320, a visualization engine 322, and database storage 324. Alternative embodiments of the analysis server 208 and/or the storage system 310 may comprise more, less, or functionally equivalent components and modules.

The input module 314 may be configured to receive commands and preferences from the user device 202*a*. In various examples, the input module 314 receives selections from the user which will be used to perform the analysis. The output of the analysis may be an interactive visualization.

The input module 314 may provide the user a variety of interface windows allowing the user to select and access a database, choose fields associated with the database, choose a metric, choose one or more filters, and identify resolution parameters for the analysis. In one example, the input module 314 receives a database identifier and accesses a large multi-dimensional database. The input module 314 may scan the database and provide the user with an interface window allowing the user to identify an ID field. An ID field is an identifier for each data point. In one example, the identifier is unique. The same column name may be present in the table from which filters are selected. After the ID field is selected, the input module 314 may then provide the user with another interface window to allow the user to choose one or more data fields from a table of the database.

Although interactive windows may be described herein, it will be appreciated that any window, graphical user interface, and/or command line may be used to receive or prompt a user or user device 202*a* for information.

The filter module 316 may subsequently provide the user with an interface window to allow the user to select a metric to be used in analysis of the data within the chosen data fields. The filter module 316 may also allow the user to select and/or define one or more filters.

The resolution module 218 may allow the user to select a resolution, including filter parameters. In one example, the user enters a number of intervals and a percentage overlap for a filter.

The analysis module 320 may perform data analysis based on the database and the information provided by the user. In various embodiments, the analysis module 320 performs an algebraic topological analysis to identify structures and relationships within data and clusters of data. It will be appreciated that the analysis module 320 may use parallel algorithms or use generalizations of various statistical techniques (e.g., generalizing the bootstrap to zig-zag methods) to increase the size of data sets that can be processed. The analysis is further discussed in FIG. 8. It will be appreciated that the analysis module 320 is not limited to algebraic topological analysis but may perform any analysis.

The visualization engine 322 generates an interactive visualization including the output from the analysis module 320. The interactive visualization allows the user to see all or part of the analysis graphically. The interactive visualization also allows the user to interact with the visualization. For example, the user may select portions of a graph from within the visualization to see and/or interact with the underlying data and/or underlying analysis. The user may then change the parameters of the analysis (e.g., change the metric, filter(s), or resolution(s)) which allows the user to visually identify relationships in the data that may be otherwise undetectable using prior means. The interactive visualization is further described in FIGS. 9-11.

The database storage 324 is configured to store all or part of the database that is being accessed. In some embodiments, the database storage 324 may store saved portions of the database. Further, the database storage 324 may be used to store user preferences, parameters, and analysis output thereby allowing the user to perform many different functions on the database without losing previous work.

It will be appreciated that that all or part of the processing module 312 may be at the user device 202*a* or the database storage server 206. In some embodiments, all or some of the functionality of the processing module 312 may be performed by the user device 202*a*.

In various embodiments, systems and methods discussed herein may be implemented with one or more digital devices. In some examples, some embodiments discussed herein may be implemented by a computer program (instructions) executed by a processor. The computer program may provide a graphical user interface. Although such a computer program is discussed, it will be appreciated that embodiments may be performed using any of the following, either alone or in combination, including, but not limited to, a computer program, multiple computer programs, firmware, and/or hardware.

A module and/or engine may include any processor or combination of processors. In some examples, a module and/or engine may include or be a part of a processor, digital signal processor (DSP), application specific integrated circuit (ASIC), an integrated circuit, and/or the like. In various embodiments, the module and/or engine may be software or firmware.

Figure 4:
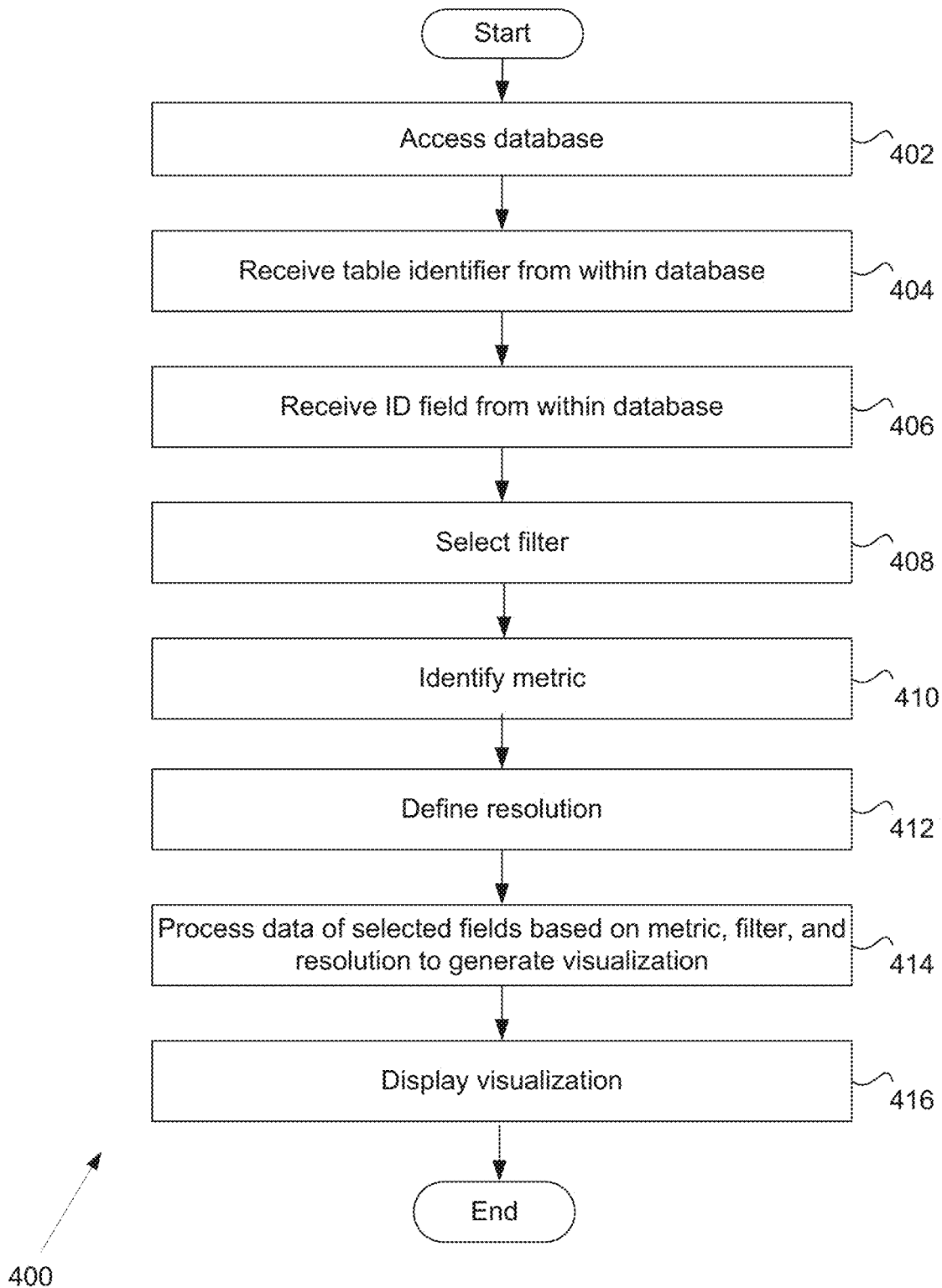
FIG. 4 is a flow chart depicting an example method of dataset analysis and visualization in some embodiments.

FIG. 4 is a flow chart 400 depicting an example method of dataset analysis and visualization in some embodiments. In step 402, the input module 314 accesses a database. The database may be any data structure containing data (e.g., a very large dataset of multidimensional data). In some embodiments, the database may be a relational database. In some examples, the relational database may be used with MySQL, Oracle, Microsoft SQL Server, Aster nCluster, Teradata, and/or Vertica. It will be appreciated that the database may not be a relational database.

In some embodiments, the input module 314 receives a database identifier and a location of the database (e.g., the data storage server 206) from the user device 202*a* (see FIG. 2). The input module 314 may then access the identified database. In various embodiments, the input module 314 may read data from many different sources, including, but not limited to MS Excel files, text files (e.g., delimited or CSV), Matlab .mat format, or any other file.

In some embodiments, the input module 314 receives an IP address or hostname of a server hosting the database, a username, password, and the database identifier. This information (herein referred to as "connection information") may be cached for later use. It will be appreciated that the database may be locally accessed and that all, some, or none of the connection information may be required. In one example, the user device 202*a* may have full access to the database stored locally on the user device 202*a* so the IP address is unnecessary. In another example, the user device 202*a* may already have loaded the database and the input module 314 merely begins by accessing the loaded database.

In various embodiments, the identified database stores data within tables. A table may have a "column specification" which stores the names of the columns and their data types. A "row" in a table, may be a tuple with one entry for each column of the correct type. In one example, a table to store employee records might have a column specification such as:

employee_id primary key int (this may store the employee's ID as an integer, and uniquely identifies a row)

age int gender char(1) (gender of the employee may be a single character either M or F)

salary double (salary of an employee may be a floating point number)

name varchar (name of the employee may be a variable-length string)

In this example, each employee corresponds to a row in this table. Further, the tables in this example relational database are organized into logical units called databases. An analogy to file systems is that databases can be thought of as folders and files as tables. Access to databases may be controlled by the database administrator by assigning a username/password pair to authenticate users.

Once the database is accessed, the input module 314 may allow the user to access a previously stored analysis or to begin a new analysis. If the user begins a new analysis, the input module 314 may provide the user device 202*a* with an interface window allowing the user to identify a table from within the database. In one example, the input module 314 provides a list of available tables from the identified database.

In step 404, the input module 314 receives a table identifier identifying a table from within the database. The input module 314 may then provide the user with a list of available ID fields from the table identifier. In step 406, the input module 314 receives the ID field identifier from the user and/or user device 202*a*. The ID field is, in some embodiments, the primary key.

Having selected the primary key, the input module 314 may generate a new interface window to allow the user to select data fields for analysis. In step 408, the input module 314 receives data field identifiers from the user device 202*a*. The data within the data fields may be later analyzed by the analysis module 320.

In step 410, the filter module 316 identifies a metric. In some embodiments, the filter module 316 and/or the input module 314 generates an interface window allowing the user of the user device 202*a* options for a variety of different metrics and filter preferences. The interface window may be a drop down menu identifying a variety of distance metrics to be used in the analysis. Metric options may include, but are not limited to, Euclidean, DB Metric, variance normalized Euclidean, and total normalized Euclidean. The metric and the analysis are further described herein.

In step 412, the filter module 316 selects one or more filters. In some embodiments, the user selects and provides filter identifier(s) to the filter module 316. The role of the filters in the analysis is also further described herein. The filters, for example, may be user defined, geometric, or based on data which has been pre-processed. In some embodiments, the data based filters are numerical arrays which can assign a set of real numbers to each row in the table or each point in the data generally.

A variety of geometric filters may be available for the user to choose. Geometric filters may include, but are not limited to:

Density
L1Eccentricity
L-infinity Eccentricity
Witness based Density
Witness based Eccentricity
Eccentricity as distance from a fixed point
Approximate Kurtosis of the Eccentricity In step 414, the resolution module 218 defines the resolution to be used with a filter in the analysis. The resolution may comprise a number of intervals and an overlap parameter. In various embodiments, the resolution module 218 allows the user to adjust the number of intervals and overlap parameter (e.g., percentage overlap) for one or more filters.

In step 416, the analysis module 320 processes data of selected fields based on the metric, filter(s), and resolution(s) to generate the visualization. This process is discussed in FIG. 8.

In step 418, the visualization module 322 displays the interactive visualization. In various embodiments, the visualization may be rendered in two or three dimensional space. The visualization module 322 may use an optimization algorithm for an objective function which is correlated with good visualization (e.g., the energy of the embedding). The visualization may show a collection of nodes corresponding to each of the partial clusters in the analysis output and edges connecting them as specified by the output. The interactive visualization is further discussed in FIGS. 9-11.

Although many examples discuss the input module 314 as providing interface windows, it will be appreciated that all or some of the interface may be provided by a client on the user device 202a. Further, in some embodiments, the user device 202a may be running all or some of the processing module 212.

Figure 5:
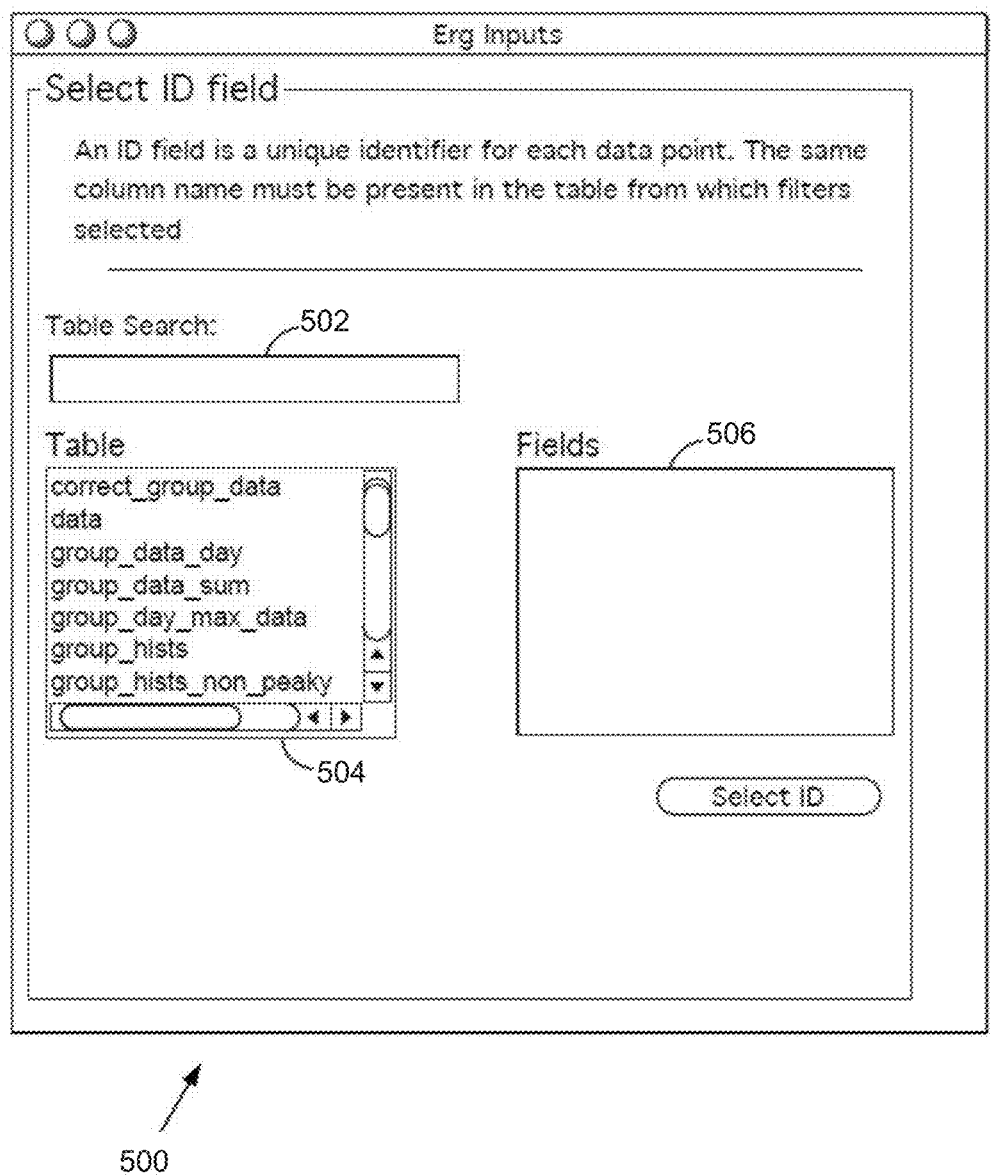
FIG. 5 is an example ID field selection interface window in some embodiments.
Figure 6A:
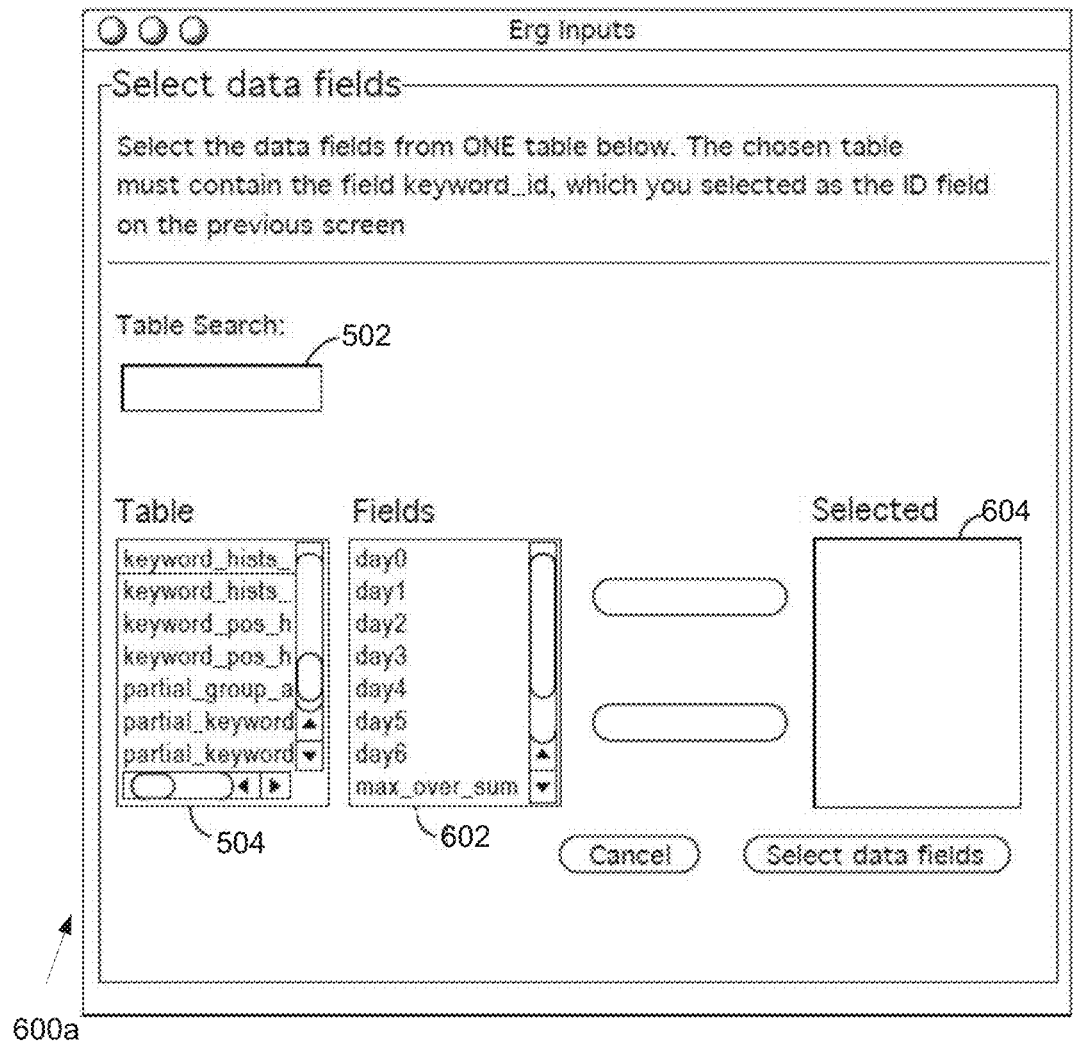
FIG. 6a is an example data field selection interface window in some embodiments.
Figure 6B:
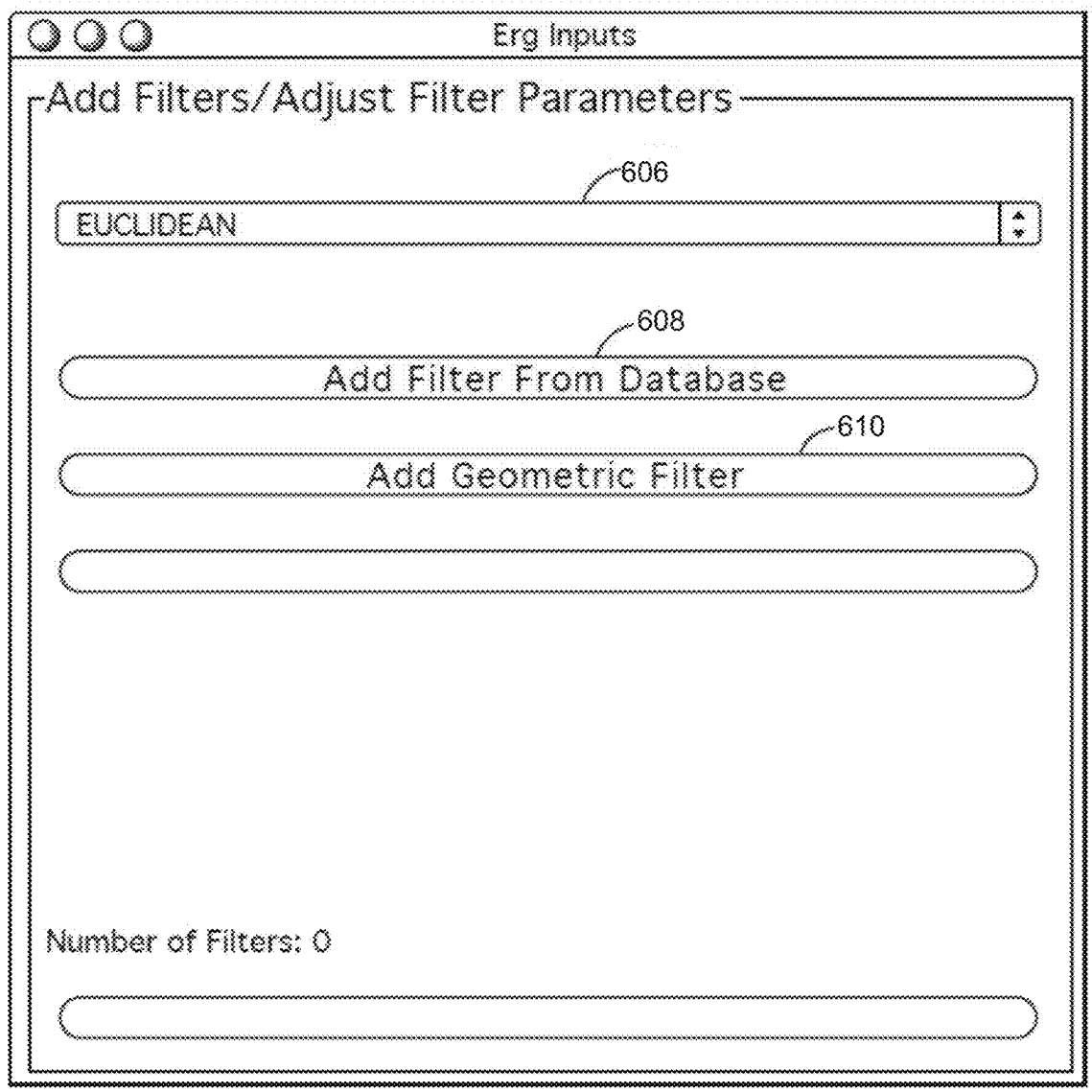
FIG. 6b is an example metric and filter selection interface window in some embodiments.
Figure 7:
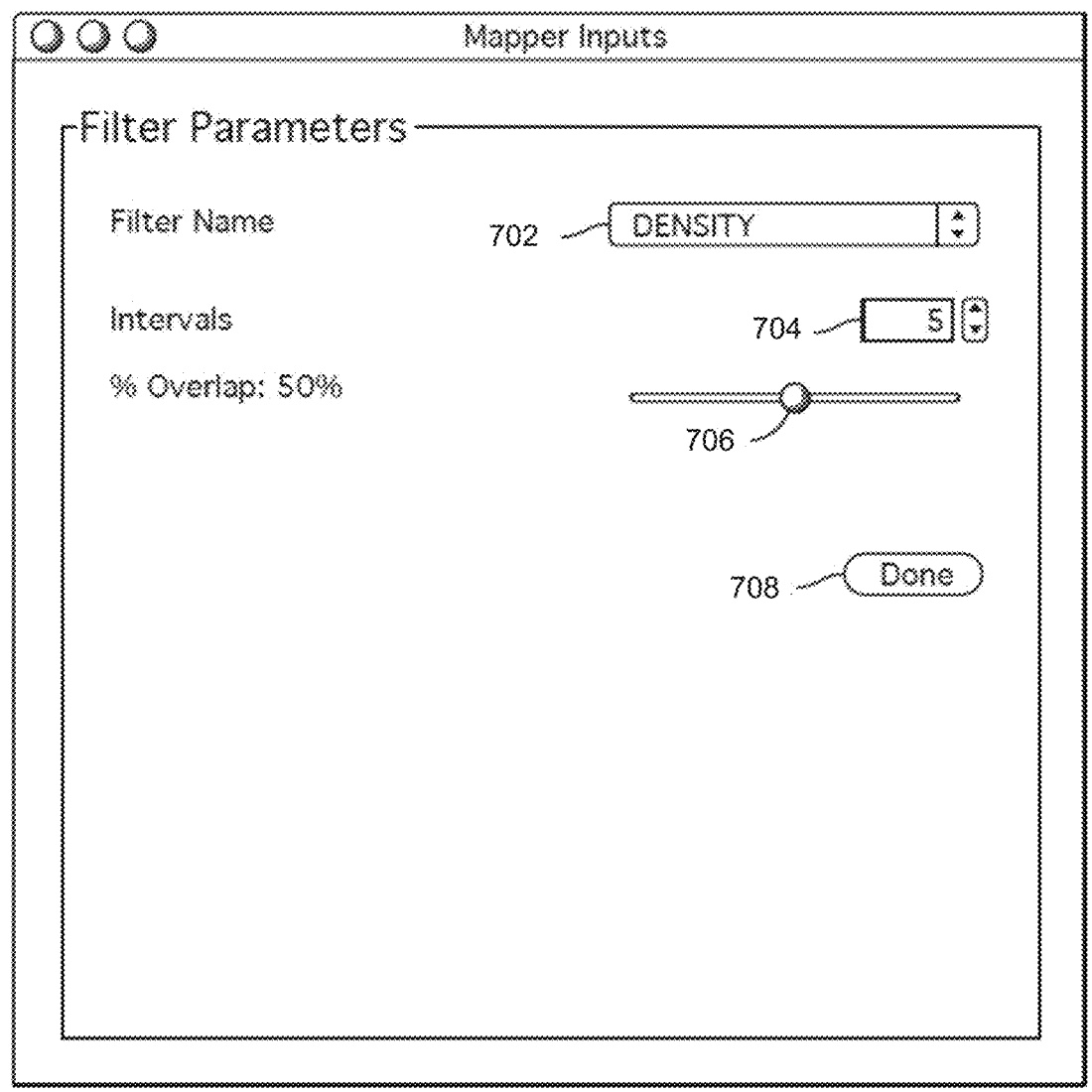
FIG. 7 is an example filter parameter interface window in some embodiments.

FIGS. 5-7 depict various interface windows to allow the user to make selections, enter information (e.g., fields, metrics, and filters), provide parameters (e.g., resolution), and provide data (e.g., identify the database) to be used with analysis. It will be appreciated that any graphical user interface or command line may be used to make selections, enter information, provide parameters, and provide data.

FIG. 5 is an example ID field selection interface window 500 in some embodiments. The ID field selection interface window 500 allows the user to identify an ID field. The ID field selection interface window 500 comprises a table search field 502, a table list 504, and a fields selection window 506.

In various embodiments, the input module 314 identifies and accesses a database from the database storage 324, user device 202a, or the data storage server 206. The input module 314 may then generate the ID field selection interface window 500 and provide a list of available tables of the selected database in the table list 504. The user may click on a table or search for a table by entering a search query (e.g., a keyword) in the table search field 502. Once a table is identified (e.g., clicked on by the user), the fields selection window 506 may provide a list of available fields in the selected table. The user may then choose a field from the fields selection window 506 to be the ID field. In some embodiments, any number of fields may be chosen to be the ID field(s).

FIG. 6a is an example data field selection interface window 600a in some embodiments. The data field selection interface window 600a allows the user to identify data fields. The data field selection interface window 600a comprises a table search field 502, a table list 504, a fields selection window 602, and a selected window 604.

In various embodiments, after selection of the ID field, the input module 314 provides a list of available tables of the selected database in the table list 504. The user may click on a table or search for a table by entering a search query (e.g., a keyword) in the table search field 502. Once a table is identified (e.g., clicked on by the user), the fields selection window 506 may provide a list of available fields in the selected table. The user may then choose any number of fields from the fields selection window 602 to be data fields. The selected data fields may appear in the selected window 604. The user may also deselect fields that appear in the selected window 604.

It will be appreciated that the table selected by the user in the table list 504 may be the same table selected with regard to FIG. 5. In some embodiments, however, the user may select a different table. Further, the user may, in various embodiments, select fields from a variety of different tables.

FIG. 6b is an example metric and filter selection interface window 600b in some embodiments. The metric and filter selection interface window 600b allows the user to identify a metric, add filter(s), and adjust filter parameters. The metric and filter selection interface window 600b comprises a metric pull down menu 606, an add filter from database button 608, and an add geometric filter button 610.

In various embodiments, the user may click on the metric pull down menu 606 to view a variety of metric options. Various metric options are described herein. In some embodiments, the user may define a metric. The user defined metric may then be used with the analysis.

In one example, finite metric space data may be constructed from a data repository (i.e., database, spreadsheet, or Matlab file). This may mean selecting a collection of fields whose entries will specify the metric using the standard Euclidean metric for these fields, when they are floating point or integer variables. Other notions of distance, such as graph distance between collections of points, may be supported.

The analysis module 320 may perform analysis using the metric as a part of a distance function. The distance function can be expressed by a formula, a distance matrix, or other routine which computes it. The user may add a filter from a database by clicking on the add filter from database button 608. The metric space may arise from a relational database, a Matlab file, an Excel spreadsheet, or other methods for storing and manipulating data. The metric and filter selection interface window 600b may allow the user to browse for other filters to use in the analysis. The analysis and metric function are further described in FIG. 8.

The user may also add a geometric filter 610 by clicking on the add geometric filter button 610. In various embodiments, the metric and filter selection interface window 600b may provide a list of geometric filters from which the user may choose.

FIG. 7 is an example filter parameter interface window 700 in some embodiments. The filter parameter interface window 700 allows the user to determine a resolution for one or more selected filters (e.g., filters selected in the metric and filter selection interface window 600). The filter parameter interface window 700 comprises a filter name menu 702, an interval field 704, an overlap bar 706, and a done button 708.

The filter parameter interface window 700 allows the user to select a filter from the filter name menu 702. In some embodiments, the filter name menu 702 is a drop down box indicating all filters selected by the user in the metric and filter selection interface window 600. Once a filter is chosen, the name of the filter may appear in the filter name menu 702. The user may then change the intervals and overlap for one, some, or all selected filters.

The interval field 704 allows the user to define a number of intervals for the filter identified in the filter name menu 702. The user may enter a number of intervals or scroll up or down to get to a desired number of intervals. Any number of intervals may be selected by the user. The function of the intervals is further discussed in FIG. 8.

The overlap bar 706 allows the user to define the degree of overlap of the intervals for the filter identified in the filter name menu 702. In one example, the overlap bar 706 includes a slider that allows the user to define the percentage overlap for the interval to be used with the identified filter. Any percentage overlap may be set by the user.

Once the intervals and overlap are defined for the desired filters, the user may click the done button. The user may then go back to the metric and filter selection interface window 600 and see a new option to run the analysis. In some embodiments, the option to run the analysis may be available in the filter parameter interface window 700. Once the analysis is complete, the result may appear in an interactive visualization which is further described in FIGS. 9-11.

It will be appreciated that that interface windows in FIGS. 4-7 are example. The example interface windows are not limited to the functional objects (e.g., buttons, pull down menus, scroll fields, and search fields) shown. Any number of different functional objects may be used. Further, as described herein, any other interface, command line, or graphical user interface may be used.

Figure 8:
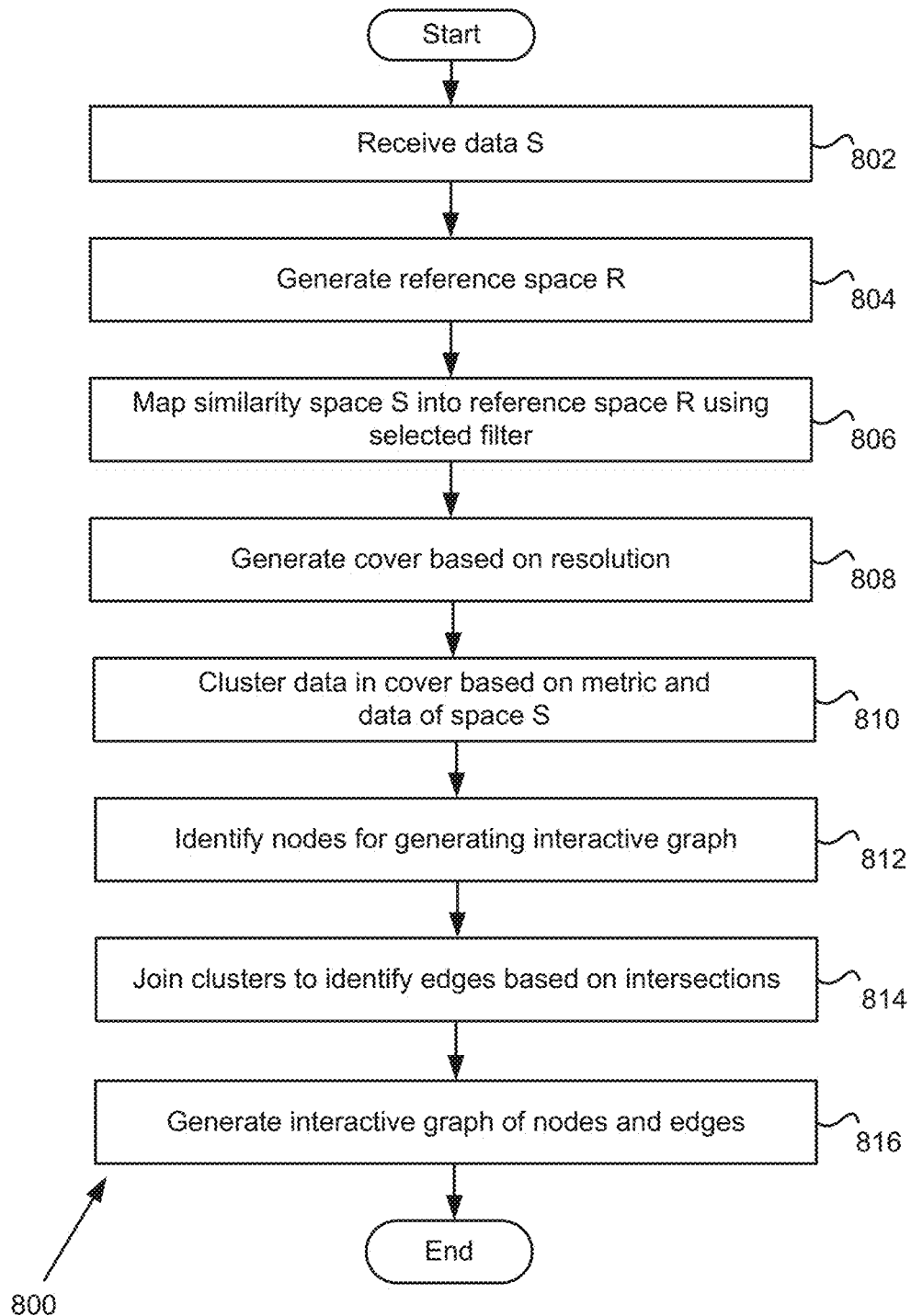
FIG. 8 is a flowchart for data analysis and generating a visualization in some embodiments.

FIG. 8 is a flowchart 800 for data analysis and generating an interactive visualization in some embodiments. In various embodiments, the processing on data and user-specified options is motivated by techniques from topology and, in some embodiments, algebraic topology. These techniques may be robust and general. In one example, these techniques apply to almost any kind of data for which some qualitative idea of "closeness" or "similarity" exists. The techniques discussed herein may be robust because the results may be relatively insensitive to noise in the data, user options, and even to errors in the specific details of the qualitative measure of similarity, which, in some embodiments, may be generally refer to as "the distance function" or "metric." It will be appreciated that while the description of the algorithms below may seem general, the implementation of techniques described herein may apply to any level of generality.

In step 802, the input module 314 receives data S. In one example, a user identifies a data structure and then identifies ID and data fields. Data S may be based on the information within the ID and data fields. In various embodiments, data S is treated as being processed as a finite "similarity space," where data S has a real-valued function d defined on pairs of points s and t in S, such that:

$$d(s,s)=0$$

$$d(s,t)=d(t,s)$$

$$d(s,t)>=0$$

These conditions may be similar to requirements for a finite metric space, but the conditions may be weaker. In various examples, the function is a metric.

It will be appreciated that data S may be a finite metric space, or a generalization thereof, such as a graph or weighted graph. In some embodiments, data S be specified by a formula, an algorithm, or by a distance matrix which specifies explicitly every pairwise distance.

In step 804, the input module 314 generates reference space R. In one example, reference space R may be a well-known metric space (e.g., such as the real line). The reference space R may be defined by the user. In step 806, the analysis module 320 generates a map ref( ) from S into R. The map ref( ) from S into R may be called the "reference map."

In one example, a reference of map from S is to a reference metric space R. R may be Euclidean space of some dimension, but it may also be the circle, torus, a tree, or other metric space. The map can be described by one or more filters (i.e., real valued functions on S). These filters can be defined by geometric invariants, such as the output of a density estimator, a notion of data depth, or functions specified by the origin of S as arising from a data set.

In step 808, the resolution module 218 generates a cover of R based on the resolution received from the user (e.g., filter(s), intervals, and overlap—see FIG. 7). The cover of R may be a finite collection of open sets (in the metric of R) such that every point in R lies in at least one of these sets. In various examples, R is k-dimensional Euclidean space, where k is the number of filter functions. More precisely in this example, R is a box in k-dimensional Euclidean space given by the product of the intervals [min_k, max_k], where min_k is the minimum value of the k-th filter function on S, and max_k is the maximum value.

For example, suppose there are 2 filter functions, F1 and F2, and that F1's values range from −1 to +1, and F2's values range from 0 to 5. Then the reference space is the rectangle in the x/y plane with corners (−1, 0), (1, 0), (−1, 5), (1, 5), as every point s of S will give rise to a pair (F1(s), F2(s)) that lies within that rectangle.

In various embodiments, the cover of R is given by taking products of intervals of the covers of [min_k, max_k] for each of the k filters. In one example, if the user requests 2 intervals and a 50% overlap for F1, the cover of the interval [−1, +1] will be the two intervals (−1.5, 0.5), (−0.5, 1.5). If the user requests 5 intervals and a 30% overlap for F2, then that cover of [0, 5] will be (−0.3, 1.3), (0.7, 2.3), (1.7, 3.3), (2.7, 4.3), (3.7, 5.3). These intervals may give rise to a cover of the 2-dimensional box by taking all possible pairs of intervals where the first of the pair is chosen from the cover for F1 and the second from the cover for F2. This may give rise to 2*5, or 10, open boxes that covered the 2-dimensional reference space. However, it will be appreciated that the intervals may not be uniform, or that the covers of a k-dimensional box may not be constructed by products of intervals. In some embodiments, there are many other choices of intervals. Further, in various embodiments, a wide range of covers and/or more general reference spaces may be used.

In one example, given a cover, $C_1, \ldots C_m$, of R, the reference map is used to assign a set of indices to each point in S, which are the indices of the $C_j$ such that ref(s) belongs to $C_j$. This function may be called ref_tags(s). In a language such as Java, ref_tags would be a method that returned an int[ ]. Since the C's cover R in this example, ref(s) must lie in at least one of them, but the elements of the cover usually overlap one another, which means that points that "land near the edges" may well reside in multiple cover sets. In considering the two filter example, if F1(s) is −0.99, and F2(s) is 0.001, then ref(s) is (−0.99, 0.001), and this lies in the cover element (−1.5, 0.5)×(−0.3, 1.3). Supposing that was labeled $C_1$, the reference map may assign s to the set {1}. On the other hand, if t is mapped by F1, F2 to (0.1, 2.1), then ref(t) will be in (−1.5, 0.5)×(0.7, 2.3), (−0.5, 1.5)×(0.7, 2.3), (−1.5, 0.5)×(1.7, 3.3), and (−0.5, 1.5)×(1.7, 3.3), so the set of indices would have four elements for t.

Having computed, for each point, which "cover tags" it is assigned to, for each cover element, $C_d$, the points may be constructed, whose tags include d, as set S(d). This may mean that every point s is in S(d) for some d, but some points may belong to more than one such set. In some embodiments, there is, however, no requirement that each S(d) is non-empty, and it is frequently the case that some of these sets are empty. In the non-parallelized version of some embodiments, each point x is processed in turn, and x is inserted into a hash-bucket for each j in ref_tags(t) (that is, this may be how S(d) sets are computed).

It will be appreciated that the cover of the reference space R may be controlled by the number of intervals and the overlap identified in the resolution (e.g., see FIG. 7). For example, the more intervals, the finer the resolution in S—that is, the fewer points in each S(d), but the more similar (with respect to the filters) these points may be. The greater the overlap, the more times that clusters in S(d) may intersect clusters in S(e)—this means that more "relationships" between points may appear, but, in some embodiments, the greater the overlap, the more likely that accidental relationships may appear.

In step 810, the analysis module 320 clusters each S(d) based on the metric, filter, and the space S. In some embodiments, a dynamic single-linkage clustering algorithm may be used to partition S(d). It will be appreciated that any number of clustering algorithms may be used with embodiments discussed herein. For example, the clustering scheme may be k-means clustering for some k, single linkage clustering, average linkage clustering, or any method specified by the user.

The significance of the user-specified inputs may now be seen. In some embodiments, a filter may amount to a "forced stretching" in a certain direction. In some embodiments, the analysis module 320 may not cluster two points unless ALL of the filter values are sufficiently "related" (recall that while normally related may mean "close," the cover may impose a much more general relationship on the filter values, such as relating two points s and t if ref(s) and ref(t) are sufficiently close to the same circle in the plane). In various embodiments, the ability of a user to impose one or more "critical measures" makes this technique more powerful than regular clustering, and the fact that these filters can be anything, is what makes it so general.

The output may be a simplicial complex, from which one can extract its 1-skeleton. The nodes of the complex may be partial clusters, (i.e., clusters constructed from subsets of S specified as the preimages of sets in the given covering of the reference space R).

In step 812, the visualization engine 322 identifies nodes which are associated with a subset of the partition elements of all of the S(d) for generating an interactive visualization. For example, suppose that S={1, 2, 3, 4}, and the cover is $C_1$, $C_2$, $C_3$. Then if ref_tags(1)={1, 2, 3} and ref_tags(2)={2, 3}, and ref_tags(3)={3}, and finally ref_tags(4)={1, 3}, then S(1) in this example is {1, 4}, S(2)={1, 2}, and S(3)={1, 2, 3, 4}. If 1 and 2 are close enough to be clustered, and 3 and 4 are, but nothing else, then the clustering for S(1) may be {1} {3}, and for S(2) it may be {1, 2}, and for S(3) it may be {1, 2}, {3, 4}. So the generated graph has, in this example, at most four nodes, given by the sets {1}, {4}, {1, 2}, and {3, 4} (note that {1, 2} appears in two different clusterings). Of the sets of points that are used, two nodes intersect provided that the associated node sets have a non-empty intersection (although this could easily be modified to allow users to require that the intersection is "large enough" either in absolute or relative terms).

Nodes may be eliminated for any number of reasons. For example, a node may be eliminated as having too few points and/or not being connected to anything else. In some embodiments, the criteria for the elimination of nodes (if any) may be under user control or have application-specific requirements imposed on it. For example, if the points are consumers, for instance, clusters with too few people in area codes served by a company could be eliminated. If a cluster was found with "enough" customers, however, this might indicate that expansion into area codes of the other consumers in the cluster could be warranted.

In step 814, the visualization engine 322 joins clusters to identify edges (e.g., connecting lines between nodes). Once the nodes are constructed, the intersections (e.g., edges) may be computed "all at once," by computing, for each point, the set of node sets (not ref_tags, this time). That is, for each s in S, node_id_set(s) may be computed, which is an int[ ]. In some embodiments, if the cover is well behaved, then this operation is linear in the size of the set S, and we then iterate over each pair in node_id_set(s). There may be an edge between two node_id's if they both belong to the same node_id_set( ) value, and the number of points in the intersection is precisely the number of different node_id sets in which that pair is seen. This means that, except for the clustering step (which is often quadratic in the size of the sets S(d), but whose size may be controlled by the choice of cover), all of the other steps in the graph construction algorithm may be linear in the size of S, and may be computed quite efficiently.

Figure 10:
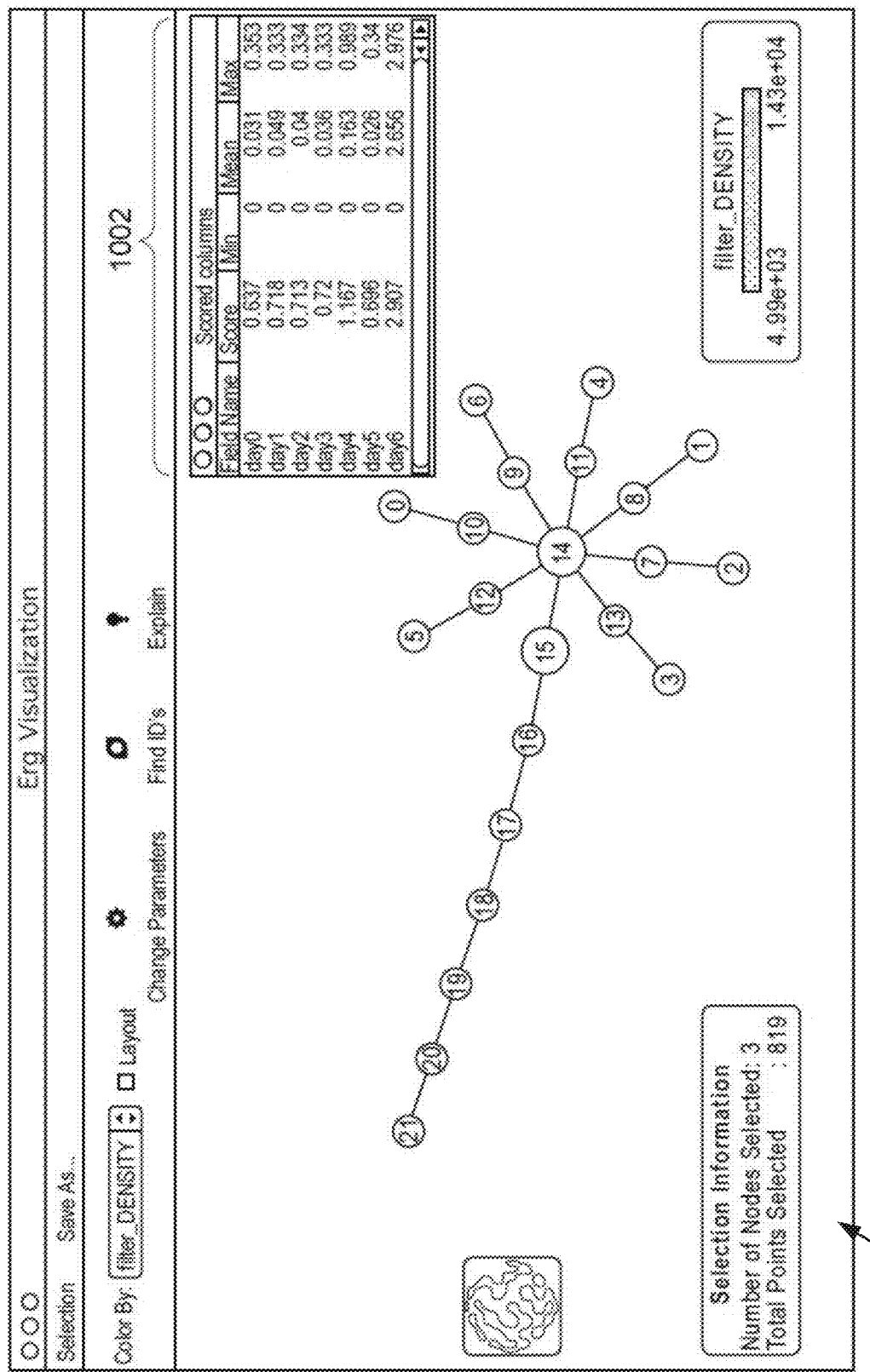
FIG. 10 is an example interactive visualization displaying an explain information window in some embodiments.
Figure 11:
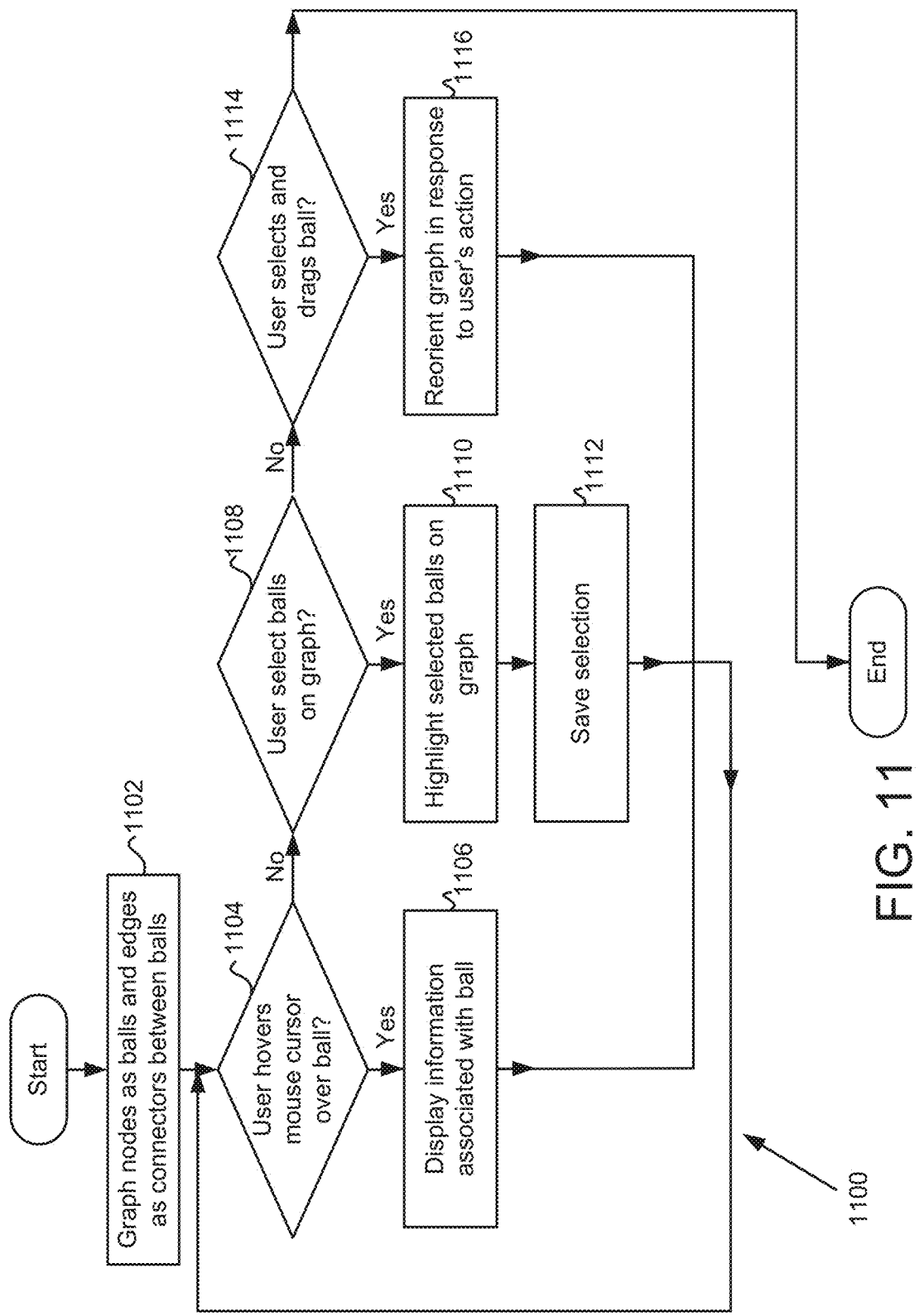
FIG. 11 is a flowchart of functionality of the interactive visualization in some embodiments.

In step 816, the visualization engine 322 generates the interactive visualization of interconnected nodes (e.g., nodes and edges displayed in FIGS. 10 and 11).

It will be appreciated that it is possible, in some embodiments, to make sense in a fairly deep way of connections between various ref( ) maps and/or choices of clustering. Further, in addition to computing edges (pairs of nodes), the embodiments described herein may be extended to compute triples of nodes, etc. For example, the analysis module 320 may compute simplicial complexes of any dimension (by a variety of rules) on nodes, and apply techniques from homology theory to the graphs to help users understand a structure in an automatic (or semi-automatic) way.

Further, it will be appreciated that uniform intervals in the covering may not always be a good choice. For example, if the points are exponentially distributed with respect to a given filter, uniform intervals can fail—in such case adaptive interval sizing may yield uniformly-sized S(d) sets, for instance.

Further, in various embodiments, an interface may be used to encode techniques for incorporating third-party extensions to data access and display techniques. Further, an interface may be used to for third-party extensions to underlying infrastructure to allow for new methods for generating coverings, and defining new reference spaces.

Figure 9:
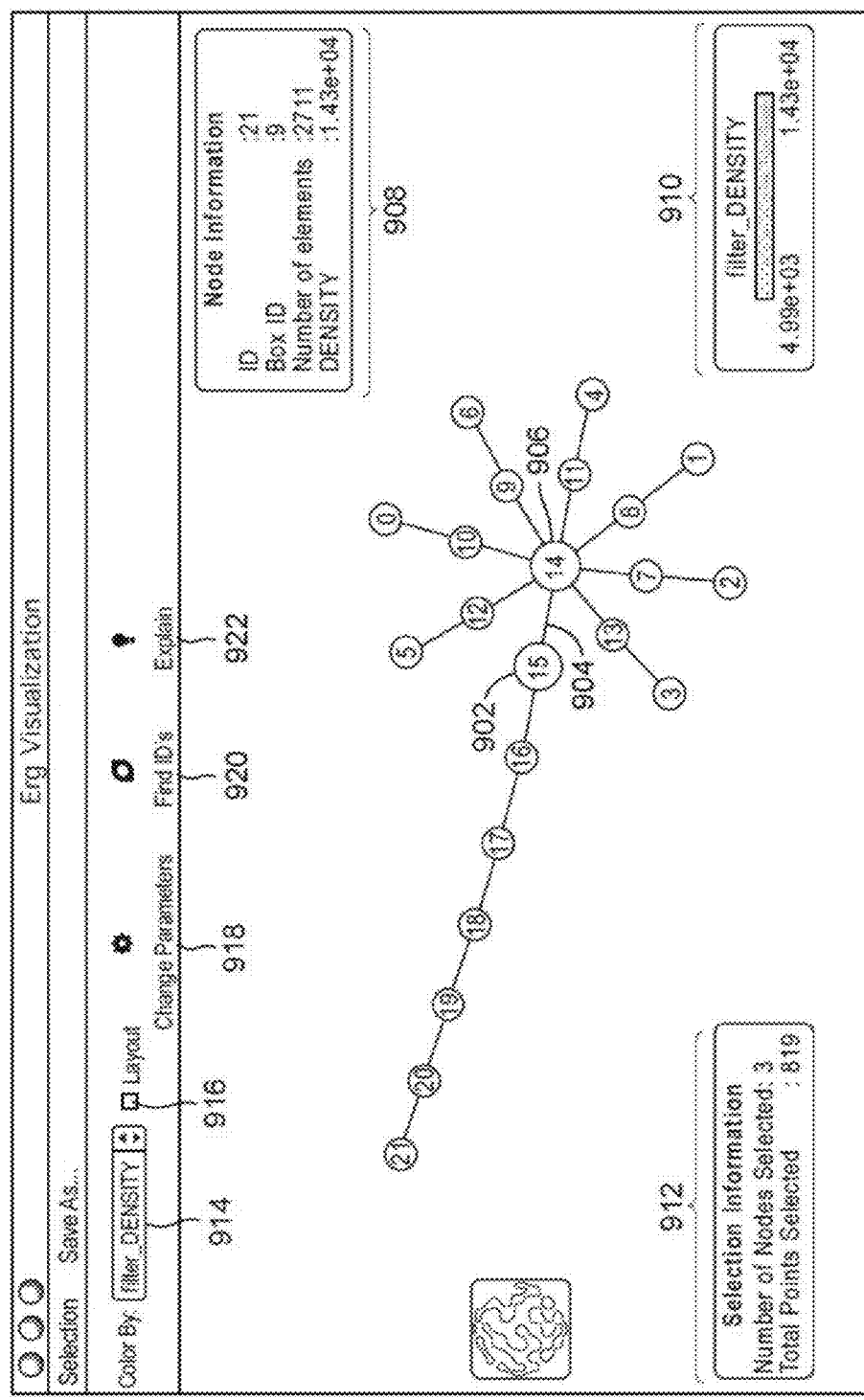
FIG. 9 is an example interactive visualization in some embodiments.

FIG. 9 is an example interactive visualization 900 in some embodiments. The display of the interactive visualization may be considered a "graph" in the mathematical sense. The interactive visualization comprises of two types of objects: nodes (e.g., nodes 902 and 906) (the colored balls) and the edges (e.g., edge 904) (the black lines). The edges connect pairs of nodes (e.g., edge 904 connects node 902 with node 906). As discussed herein, each node may represent a collection of data points (rows in the database identified by the user). In one example, connected nodes tend to include data points which are "similar to" (e.g., clustered with) each other. The collection of data points may be referred to as being "in the node." The interactive visualization may be two-dimensional, three-dimensional, or a combination of both.

In various embodiments, connected nodes and edges may form a graph or structure. There may be multiple graphs in the interactive visualization. In one example, the interactive visualization may display two or more unconnected structures of nodes and edges.

The visual properties of the nodes and edges (such as, but not limited to, color, stroke color, text, texture, shape, coordinates of the nodes on the screen) can encode any data based property of the data points within each node. For example, coloring of the nodes and/or the edges may indicate (but is not limited to) the following:

Values of fields or filters
Any general functions of the data in the nodes (e.g., if the data were unemployment rates by state, then GDP of the states may be identifiable by color the nodes)
Number of data points in the node The interactive visualization 900 may contain a "color bar" 910 which may comprise a legend indicating the coloring of the nodes (e.g., balls) and may also identify what the colors indicate. For example, in FIG. 9, color bar 910 indicates that color is based on the density filter with blue (on the far left of the color bar 910) indicating "4.99e+03" and red (on the far right of the color bar 910) indicating "1.43e+04." In general this might be expanded to show any other legend by which nodes and/or edges are colored. It will be appreciated that the, In some embodiments, the user may control the color as well as what the color (and/or stroke color, text, texture, shape, coordinates of the nodes on the screen) indicates.

The user may also drag and drop objects of the interactive visualization 900. In various embodiments, the user may reorient structures of nodes and edges by dragging one or more nodes to another portion of the interactive visualization (e.g., a window). In one example, the user may select node 902, hold node 902, and drag the node across the window. The node 902 will follow the user's cursor, dragging the structure of edges and/or nodes either directly or indirectly connected to the node 902. In some embodiments, the interactive visualization 900 may depict multiple unconnected structures. Each structure may include nodes, however, none of the nodes of either structure are connected to each other. If the user selects and drags a node of the first structure, only the first structure will be reoriented with respect to the user action. The other structure will remain unchanged. The user may wish to reorient the structure in order to view nodes, select nodes, and/or better understand the relationships of the underlying data.

In one example, a user may drag a node to reorient the interactive visualization (e.g., reorient the structure of nodes and edges). While the user selects and/or drags the node, the nodes of the structure associated with the selected node may move apart from each other in order to provide greater visibility. Once the user lets go (e.g., deselects or drops the node that was dragged), the nodes of the structure may continue to move apart from each other.

In various embodiments, once the visualization module 322 generates the interactive display, the depicted structures may move by spreading out the nodes from each other. In one example, the nodes spread from each other slowly allowing the user to view nodes distinguish from each other as well as the edges. In some embodiments, the visualization module 322 optimizes the spread of the nodes for the user's view. In one example, the structure(s) stop moving once an optimal view has been reached.

It will be appreciated that the interactive visualization 900 may respond to gestures (e.g., multitouch), stylus, or other interactions allowing the user to reorient nodes and edges and/or interacting with the underlying data.

The interactive visualization 900 may also respond to user actions such as when the user drags, clicks, or hovers a mouse cursor over a node. In some embodiments, when the user selects a node or edge, node information or edge information may be displayed. In one example, when a node is selected (e.g., clicked on by a user with a mouse or a mouse cursor hovers over the node), a node information box 908 may appear that indicates information regarding the selected node. In this example, the node information box 908 indicates an ID, box ID, number of elements (e.g., data points associated with the node), and density of the data associated with the node.

The user may also select multiple nodes and/or edges by clicking separate on each object, or drawing a shape (such as a box) around the desired objects. Once the objects are selected, a selection information box 912 may display some information regarding the selection. For example, selection information box 912 indicates the number of nodes selected and the total points (e.g., data points or elements) of the selected nodes.

The interactive visualization 900 may also allow a user to further interact with the display. Color option 914 allows the user to display different information based on color of the objects. Color option 914 in FIG. 9 is set to filter_Density, however, other filters may be chosen and the objects re-colored based on the selection. It will be appreciated that the objects may be colored based on any filter, property of data, or characterization. When a new option is chosen in the color option 914, the information and/or colors depicted in the color bar 910 may be updated to reflect the change.

Layout checkbox 914 may allow the user to anchor the interactive visualization 900. In one example, the layout checkbox 914 is checked indicating that the interactive visualization 900 is anchored. As a result, the user will not be able to select and drag the node and/or related structure. Although other functions may still be available, the layout checkbox 914 may help the user keep from accidentally moving and/or reorienting nodes, edges, and/or related structures. It will be appreciated that the layout checkbox 914 may indicate that the interactive visualization 900 is anchored when the layout checkbox 914 is unchecked and that when the layout checkbox 914 is checked the interactive visualization 900 is no longer anchored.

The change parameters button 918 may allow a user to change the parameters (e.g., add/remove filters and/or change the resolution of one or more filters). In one example, when the change parameters button 918 is activated, the user may be directed back to the metric and filter selection interface window 600 (see FIG. 6) which allows the user to add or remove filters (or change the metric). The user may then view the filter parameter interface 700 (see FIG. 7) and change parameters (e.g., intervals and overlap) for one or more filters. The analysis module 320 may then re-analyze the data based on the changes and display a new interactive visualization 900 without again having to specify the data sets, filters, etc.

The find ID's button 920 may allow a user to search for data within the interactive visualization 900. In one example, the user may click the find ID's button 920 and receive a window allowing the user to identify data or identify a range of data. Data may be identified by ID or searching for the data based on properties of data and/or metadata. If data is found and selected, the interactive visualization 900 may highlight the nodes associated with the selected data. For example, selecting a single row or collection of rows of a database or spreadsheet may produce a highlighting of nodes whose corresponding partial cluster contains any element of that selection.

In various embodiments, the user may select one or more objects and click on the explain button 922 to receive in-depth information regarding the selection. In some embodiments, when the user selects the explain button 922, the information about the data from which the selection is based may be displayed. The function of the explain button 922 is further discussed with regard to FIG. 10.

In various embodiments, the interactive visualization 900 may allow the user to specify and identify subsets of interest, such as output filtering, to remove clusters or connections which are too small or otherwise uninteresting. Further, the interactive visualization 900 may provide more general coloring and display techniques, including, for example, allowing a user to highlight nodes based on a user-specified predicate, and coloring the nodes based on the intensity of user-specified weighting functions.

The interactive visualization 900 may comprise any number of menu items. The "Selection" menu may allow the following functions:

Select singletons (select nodes which are not connected to other nodes)
Select all (selects all the nodes and edges)
Select all nodes (selects all nodes)
Select all edges
Clear selection (no selection)
Invert Selection (selects the complementary set of nodes or edges)
Select "small" nodes (allows the user to threshold nodes based on how many points they have)
Select leaves (selects all nodes which are connected to long "chains" in the graph)
Remove selected nodes
Show in a table (shows the selected nodes and their associated data in a table)
Save selected nodes (saves the selected data to whatever format the user chooses. This may allow the user to subset the data and create new datasources which may be used for further analysis.)

In one example of the "show in a table" option, information from a selection of nodes may be displayed. The information may be specific to the origin of the data. In various embodiments, elements of a database table may be listed, however, other methods specified by the user may also be included. For example, in the case of microarray data from gene expression data, heat maps may be used to view the results of the selections.

The interactive visualization 900 may comprise any number of menu items. The "Save" menu may allow may allow the user to save the whole output in a variety of different formats such as (but not limited to):

Image files (PNG/JPG/PDF/SVG etc.)
Binary output (The interactive output is saved in the binary format. The user may reopen this file at any time to get this interactive window again)

In some embodiments, graphs may be saved in a format such that the graphs may be used for presentations. This may include simply saving the image as a pdf or png file, but it may also mean saving an executable .xml file, which may permit other users to use the search and save capability to the database on the file without having to recreate the analysis.

In various embodiments, a relationship between a first and a second analysis output/interactive visualization for differing values of the interval length and overlap percentage may be displayed. The formal relationship between the first and second analysis output/interactive visualization may be that when one cover refines the next, there is a map of simplicial complexes from the output of the first to the output of the second. This can be displayed by applying a restricted form of a three-dimensional graph embedding algorithm, in which a graph is the union of the graphs for the various parameter values and in which the connections are the connections in the individual graphs as well as connections from one node to its image in the following graph. The constituent graphs may be placed in its own plane in 3D space. In some embodiments, there is a restriction that each constituent graph remain within its associated plane. Each constituent graph may be displayed individually, but a small change of parameter value may result in the visualization of the adjacent constituent graph. In some embodiments, nodes in the initial graph will move to nodes in the next graph, in a readily visualizable way.

FIG. 10 is an example interactive visualization 1000 displaying an explain information window 1002 in some embodiments. In various embodiments, the user may select a plurality of nodes and click on the explain button. When the explain button is clicked, the explain information window 1002 may be generated. The explain information window 1002 may identify the data associated with the selected object(s) as well as information (e.g., statistical information) associated with the data.

In some embodiments, the explain button allows the user to get a sense for which fields within the selected data fields are responsible for "similarity" of data in the selected nodes and the differentiating characteristics. There can be many ways of scoring the data fields. The explain information window 1002 (i.e., the scoring window in FIG. 10) is shown along with the selected nodes. The highest scoring fields may distinguish variables with respect to the rest of the data.

In one example, the explain information window 1002 indicates that data from fields day0-day6 has been selected. The minimum value of the data in all of the fields is 0. The explain information window 1002 also indicates the maximum values. For example, the maximum value of all of the data associated with the day0 field across all of the points of the selected nodes is 0.353. The average (i.e., mean) of all of the data associated with the day0 field across all of the points of the selected nodes is 0.031. The score may be a relative (e.g., normalized) value indicating the relative function of the filter; here, the score may indicate the relative density of the data associated with the day0 field across all of the points of the selected nodes. It will be appreciated that any information regarding the data and/or selected nodes may appear in the explain information window 1002.

It will be appreciated that the data and the interactive visualization 1000 may be interacted with in any number of ways. The user may interact with the data directly to see where the graph corresponds to the data, make changes to the analysis and view the changes in the graph, modify the graph and view changes to the data, or perform any kind of interaction.

FIG. 11 is a flowchart 1200 of functionality of the interactive visualization in some embodiments. In step 1202, the visualization engine 322 receives the analysis from the analysis module 320 and graphs nodes as balls and edges as connectors between balls 1202 to create interactive visualization 900 (see FIG. 9).

In step 1204, the visualization engine 322 determines if the user is hovering a mouse cursor (or has selected) a ball (i.e., a node). If the user is hovering a mouse cursor over a ball or selecting a ball, then information is displayed regarding the data associated with the ball. In one example, the visualization engine 322 displays a node information window 908.

If the visualization engine 322 does not determine that the user is hovering a mouse cursor (or has selected) a ball, then the visualization engine 322 determines if the user has selected balls on the graph (e.g., by clicking on a plurality of balls or drawing a box around a plurality of balls). If the user has selected balls on the graph, the visualization engine 322 may highlight the selected balls on the graph in step 1110. The visualization engine 322 may also display information regarding the selection (e.g., by displaying a selection information window 912). The user may also click on the explain button 922 to receive more information associated with the selection (e.g., the visualization engine 322 may display the explain information window 1002).

In step 1112, the user may save the selection. For example, the visualization engine 322 may save the underlying data, selected metric, filters, and/or resolution. The user may then access the saved information and create a new structure in another interactive visualization 900 thereby allowing the user to focus attention on a subset of the data.

If the visualization engine 322 does not determine that the user has selected balls on the graph, the visualization engine 322 may determine if the user selects and drags a ball on the graph in step 1114. If the user selects and drags a ball on the graph, the visualization engine 322 may reorient the selected balls and any connected edges and balls based on the user's action in step 1116. The user may reorient all or part of the structure at any level of granularity.

It will be appreciated that although FIG. 11 discussed the user hovering over, selecting, and/or dragging a ball, the user may interact with any object in the interactive visualization 900 (e.g., the user may hover over, select, and/or drag an edge). The user may also zoom in or zoom out using the interactive visualization 900 to focus on all or a part of the structure (e.g., one or more balls and/or edges).

Further, although balls are discussed and depicted in FIGS. 9-11, it will be appreciated that the nodes may be any shape and appear as any kind of object. Further, although some embodiments described herein discuss an interactive visualization being generated based on the output of algebraic topology, the interactive visualization may be generated based on any kind of analysis and is not limited.

For years, researchers have been collecting huge amounts of data on breast cancer, yet we are still battling the disease. Complexity, rather than quantity, is one of the fundamental issues in extracting knowledge from data. A topological data exploration and visualization platform may assist the analysis and assessment of complex data. In various embodiments, a predictive and visual cancer map generated by the topological data exploration and visualization platform may assist physicians to determine treatment options.

In one example, a breast cancer map visualization may be generated based on the large amount of available information already generated by many researchers. Physicians may send biopsy data directly to a cloud-based server which may localize a new patient's data within the breast cancer map visualization. The breast cancer map visualization may be annotated (e.g., labeled) such that the physician may view outcomes of patients with similar profiles as well as different kinds of statistical information such as survival probabilities. Each new data point from a patient may be incorporated into the breast cancer map visualization to improve accuracy of the breast cancer map visualization over time.

Although the following examples are largely focused on cancer map visualizations, it will be appreciated that at least some of the embodiments described herein may apply to any biological condition and not be limited to cancer and/or disease. For example, some embodiments, may apply to different industries.

Figure 12:
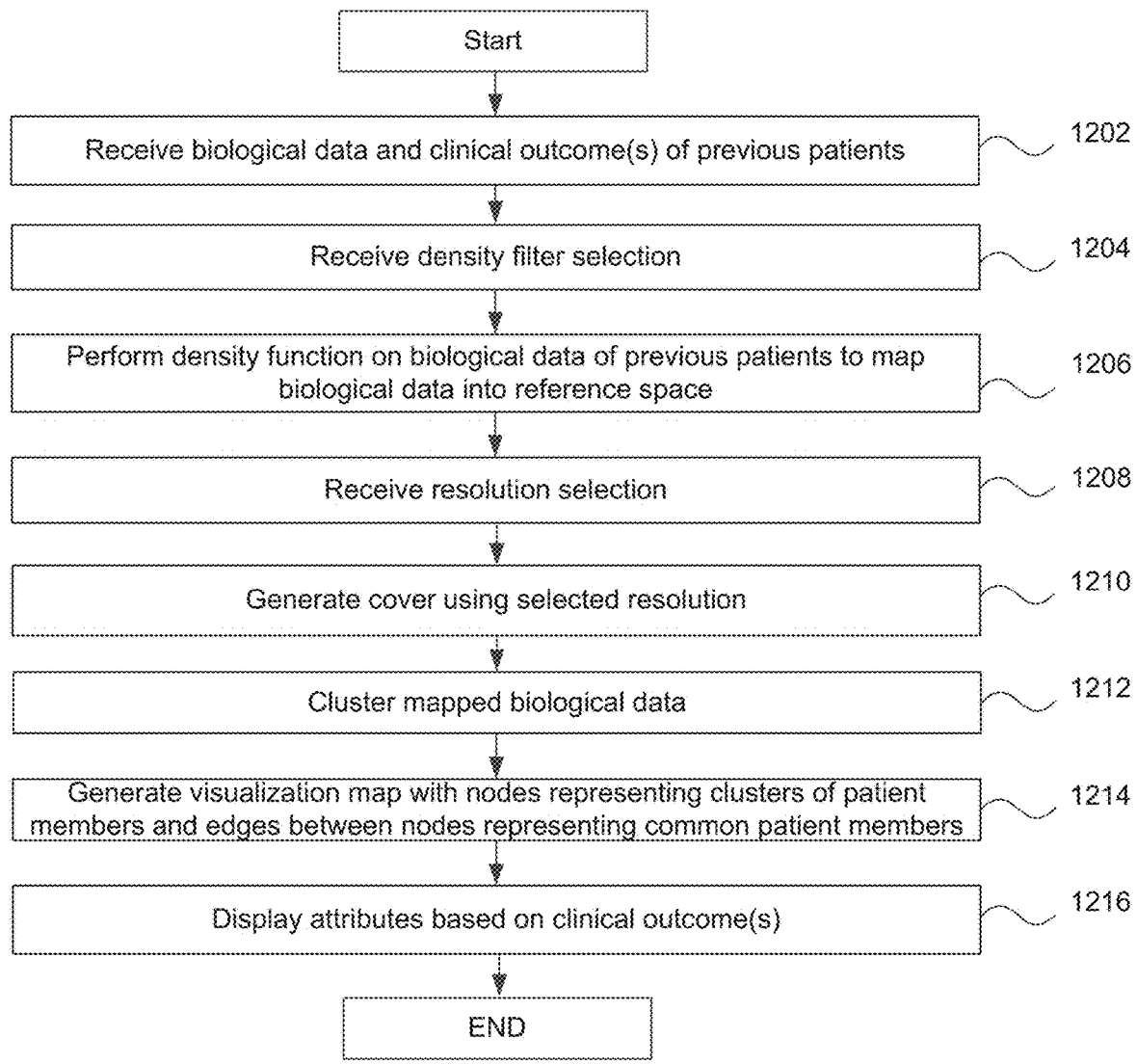
FIG. 12 is a flowchart of for generating a cancer map visualization utilizing biological data of a plurality of patients in some embodiments.

FIG. 12 is a flowchart for generating a cancer map visualization utilizing biological data of a plurality of patients in some embodiments. In various embodiments, the processing of data and user-specified options is motivated by techniques from topology and, in some embodiments, algebraic topology. As discussed herein, these techniques may be robust and general. In one example, these techniques apply to almost any kind of data for which some qualitative idea of "closeness" or "similarity" exists. It will be appreciated that the implementation of techniques described herein may apply to any level of generality.

In various embodiments, a cancer map visualization is generated using genomic data linked to clinical outcomes (i.e., medical characteristics) which may be used by physicians during diagnosis and/or treatment. Initially, publicly available data sets may be integrated to construct the topological map visualizations of patients (e.g., breast cancer patients). It will be appreciated that any private, public, or combination of private and public data sets may be integrated to construct the topological map visualizations. A map visualization may be based on biological data such as, but not limited to, gene expression, sequencing, and copy number variation. As such, the map visualization may comprise many patients with many different types of collected data. Unlike traditional methods of analysis where distinct studies of breast cancer appear as separate entities, the map visualization may fuse disparate data sets while utilizing many datasets and data types.

In various embodiments, a new patient may be localized on the map visualization. With the map visualization for subtypes of a particular disease and a new patient diagnosed with the disease, point(s) may be located among the data points used in computing the map visualization (e.g., nearest neighbor) which is closest to the new patient point. The new patient may be labeled with nodes in the map visualization containing the closest neighbor. These nodes may be highlighted to give a physician the location of the new patient among the patients in the reference data set. The highlighted nodes may also give the physician the location of the new patient relative to annotated disease subtypes.

The visualization map may be interactive and/or searchable in real-time thereby potentially enabling extended analysis and providing speedy insight into treatment.

In step 1202, biological data and clinical outcomes of previous patients may be received. The clinical outcomes may be medical characteristics. Biological data is any data that may represent a condition (e.g., a medical condition) of a person. Biological data may include any health related, medical, physical, physiological, pharmaceutical data associated with one or more patients. In one example, biological data may include measurements of gene expressions for any number of genes. In another example, biological data may include sequencing information (e.g., RNA sequencing).

In various embodiments, biological data for a plurality of patients may be publicly available. For example, various medical health facilities and/or public entities may provide gene expression data for a variety of patients. In addition to the biological data, information regarding any number of clinical outcomes, treatments, therapies, diagnoses and/or prognoses may also be provided. It will be appreciated that any kind of information may be provided in addition to the biological data.

The biological data, in one example, may be similar to data S as discussed with regard to step 802 of FIG. 8. The biological data may include ID fields that identify patients and data fields that are related to the biological information (e.g., gene expression measurements).

FIG. 13 is an example data structure 1302 including biological data 1304*a*-1304*y* for a number of patients 1308*a*-1308*n* that may be used to generate the cancer map visualization in some embodiments. Column 1302 represents different patient identifiers for different patients. The patient identifiers may be any identifier.

At least some biological data may be contained within gene expression measurements 1304*a*-1304*y*. In FIG. 13, "*y*" represents any number. For example, there may be 50,000 or more separate columns for different gene expressions related to a single patient or related to one or more samples from a patient. It will be appreciated that column 1304*a* may represent a gene expression measurement for each patient (if any for some patients) associated with the patient identifiers in column 1302. The column 1304*b* may represent a gene expression measurement of one or more genes that are different than that of column 1304*a*. As discussed, there may be any number of columns representing different gene expression measurements.

Column 1306 may include any number of clinical outcomes, prognoses, diagnoses, reactions, treatments, and/or any other information associated with each patient. All or some of the information contained in column 1306 may be displayed (e.g., by a label or an annotation that is displayed on the visualization or available to the user of the visualization via clicking) on or for the visualization.

Rows 1308*a*-1308*n* each contains biological data associated with the patient identifier of the row. For example, gene expressions in row 1308*a* are associated with patient identifier P1. As similarly discussed with regard to "*y*" herein, "*n*" represents any number. For example, there may be 100,000 or more separate rows for different patients.

It will be appreciated that there may be any number of data structures that contain any amount of biological data for any number of patients. The data structure(s) may be utilized to generate any number of map visualizations.

In step 1204, the analysis server may receive a filter selection. In some embodiments, the filter selection is a density estimation function. It will be appreciated that the filter selection may include a selection of one or more functions to generate a reference space.

In step 1206, the analysis server performs the selected filter(s) on the biological data of the previous patients to map the biological data into a reference space. In one example, a density estimation function, which is well known in the art, may be performed on the biological data (e.g., data associated with gene expression measurement data 1304*a*-1304*y*) to relate each patient identifier to one or more locations in the reference space (e.g., on a real line).

In step 1208, the analysis server may receive a resolution selection. The resolution may be utilized to identify overlapping portions of the reference space (e.g., a cover of the reference space R) in step 1210.

As discussed herein, the cover of R may be a finite collection of open sets (in the metric of R) such that every point in R lies in at least one of these sets. In various examples, R is k-dimensional Euclidean space, where k is the number of filter functions. It will be appreciated that the cover of the reference space R may be controlled by the number of intervals and the overlap identified in the resolution (e.g., see FIG. 7). For example, the more intervals, the finer the resolution in S (e.g., the similarity space of the received biological data)—that is, the fewer points in each S(d), but the more similar (with respect to the filters) these points may be. The greater the overlap, the more times that clusters in S(d) may intersect clusters in S(e)—this means that more "relationships" between points may appear, but, in some embodiments, the greater the overlap, the more likely that accidental relationships may appear.

In step 1212, the analysis server receives a metric to cluster the information of the cover in the reference space to partition S(d). In one example, the metric may be a Pearson Correlation. The clusters may form the groupings (e.g., nodes or balls). Various cluster means may be used including, but not limited to, a single linkage, average linkage, complete linkage, or k-means method.

As discussed herein, in some embodiments, the analysis module 320 may not cluster two points unless filter values are sufficiently "related" (recall that while normally related may mean "close," the cover may impose a much more general relationship on the filter values, such as relating two points s and t if ref(s) and ref(t) are sufficiently close to the same circle in the plane where ref( ) represents one or more filter functions). The output may be a simplicial complex, from which one can extract its 1-skeleton. The nodes of the complex may be partial clusters, (i.e., clusters constructed from subsets of S specified as the preimages of sets in the given covering of the reference space R).

In step 1214, the analysis server may generate the visualization map with nodes representing clusters of patient members and edges between nodes representing common patient members. In one example, the analysis server identifies nodes which are associated with a subset of the partition elements of all of the S(d) for generating an interactive visualization.

As discussed herein, for example, suppose that S={1, 2, 3, 4}, and the cover is $C_1$, $C_2$, $C_3$. Suppose cover $C_1$ contains {1, 4}, $C_2$ contains {1, 2}, and $C_3$ contains {1, 2, 3, 4}. If 1 and 2 are close enough to be clustered, and 3 and 4 are, but nothing else, then the clustering for S(1) may be {1}, {4}, and for S(2) it may be {1, 2}, and for S(3) it may be {1, 2}, {3, 4}. So the generated graph has, in this example, at most four nodes, given by the sets {1}, {4}, {1, 2}, and {3, 4} (note that {1, 2} appears in two different clusterings). Of the sets of points that are used, two nodes intersect provided that the associated node sets have a non-empty intersection (although this could easily be modified to allow users to require that the intersection is "large enough" either in absolute or relative terms).

As a result of clustering, member patients of a grouping may share biological similarities (e.g., similarities based on the biological data).

The analysis server may join clusters to identify edges (e.g., connecting lines between nodes). Clusters joined by edges (i.e., interconnections) share one or more member patients. In step 1216, a display may display a visualization map with attributes based on the clinical outcomes contained in the data structures (e.g., see FIG. 13 regarding clinical outcomes). Any labels or annotations may be utilized based on information contained in the data structures. For example, treatments, prognoses, therapies, diagnoses, and the like may be used to label the visualization. In some embodiments, the physician or other user of the map visualization accesses the annotations or labels by interacting with the map visualization.

The resulting cancer map visualization may reveal interactions and relationships that were obscured, untested, and/or previously not recognized.

Figure 14:
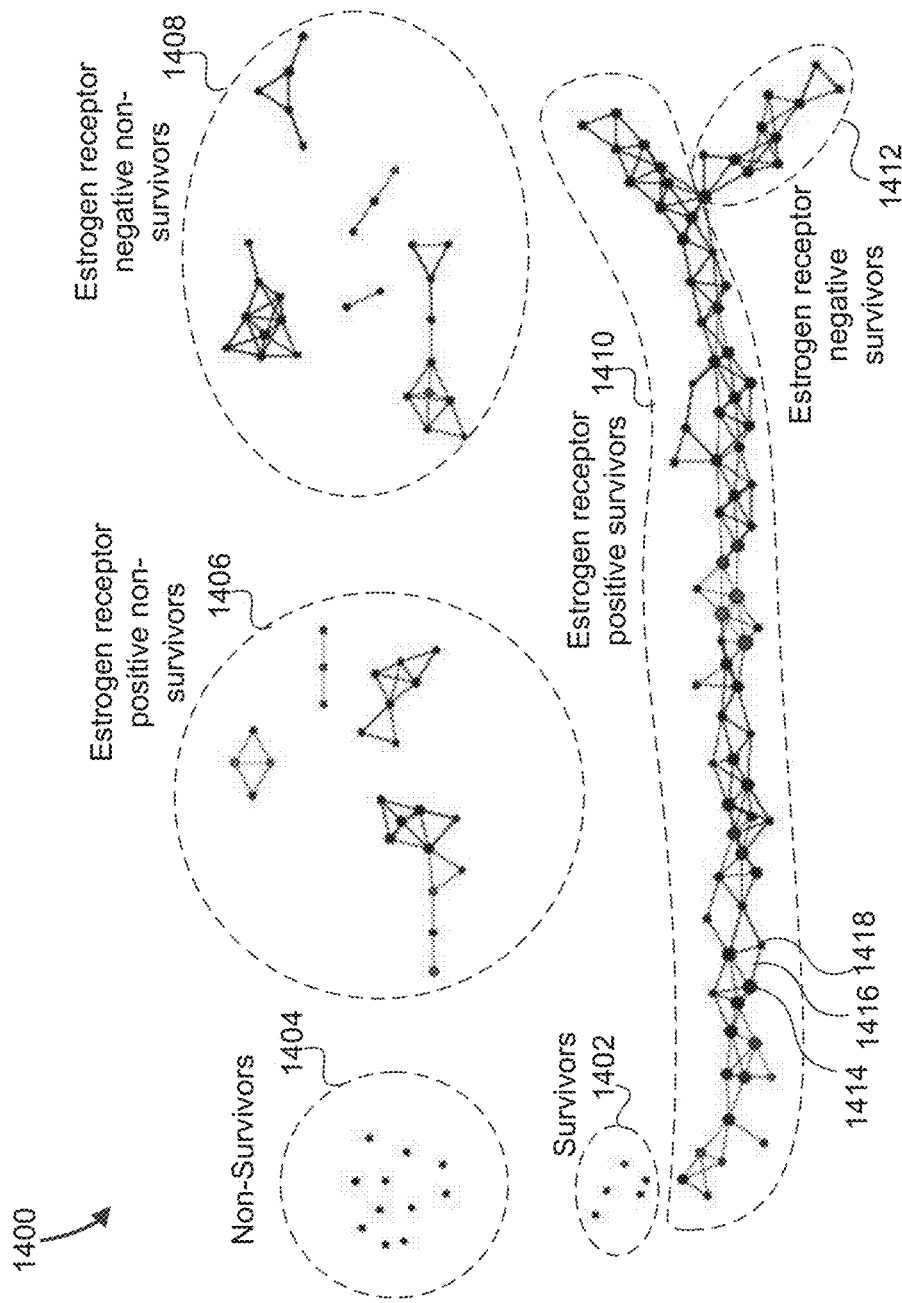
FIG. 14 is an example visualization displaying the cancer map in some embodiments.

FIG. 14 is an example visualization displaying the cancer map visualization 1400 in some embodiments. The cancer map visualization 1400 represents a topological network of cancer patients. The cancer map visualization 1400 may be based on publicly and/or privately available data.

In various embodiments, the cancer map visualization 1400 is created using gene expression profiles of excised tumors. Each node (i.e., ball or grouping displayed in the map visualization 1400) contains a subset of patients with similar genetic profiles.

As discussed herein, one or more patients (i.e., patient members of each node or grouping) may occur in multiple nodes. A patient may share a similar genetic profile with multiple nodes or multiple groupings. In one example, of 50,000 different gene expressions of the biological data, multiple patients may share a different genetic profiles (e.g., based on different gene expression combinations) with different groupings. When a patient shares a similar genetic profile with different groupings or nodes, the patient may be included within the groupings or nodes.

The cancer map visualization 1400 comprises groupings and interconnections that are associated with different clinical outcomes. All or some of the clinical outcomes may be associated with the biological data that generated the cancer map visualization 1400. The cancer map visualization 1400 includes groupings associated with survivors 1402 and groupings associated with non-survivors 1404. The cancer map visualization 1400 also includes different groupings associated with estrogen receptor positive non-survivors 1406, estrogen receptor negative non-survivors 1408, estrogen receptor positive survivors 1410, and estrogen receptor negative survivors 1412.

In various embodiments, when one or more patients are members of two or more different nodes, the nodes are interconnected by an edge (e.g., a line or interconnection). If there is not an edge between the two nodes, then there are no common member patients between the two nodes. For example, grouping 1414 shares at least one common member patient with grouping 1418. The intersection of the two groupings is represented by edge 1416. As discussed herein, the number of shared member patients of the two groupings may be represented in any number of ways including color of the interconnection, color of the groupings, size of the interconnection, size of the groupings, animations of the interconnection, animations of the groupings, brightness, or the like. In some embodiments, the number and/or identifiers of shared member patients of the two groupings may be available if the user interacts with the groupings 1414 and/or 1418 (e.g., draws a box around the two groupings and the interconnection utilizing an input device such as a mouse).

In various embodiments, a physician, on obtaining some data on a breast tumor, direct the data to an analysis server (e.g., analysis server 208 over a network such as the Internet) which may localize the patient relative to one or more groupings on the cancer map visualization 1400. The context of the cancer map visualization 1400 may enable the physician to assess various possible outcomes (e.g., proximity of representation of new patient to the different associations of clinical outcomes).

Figure 15:
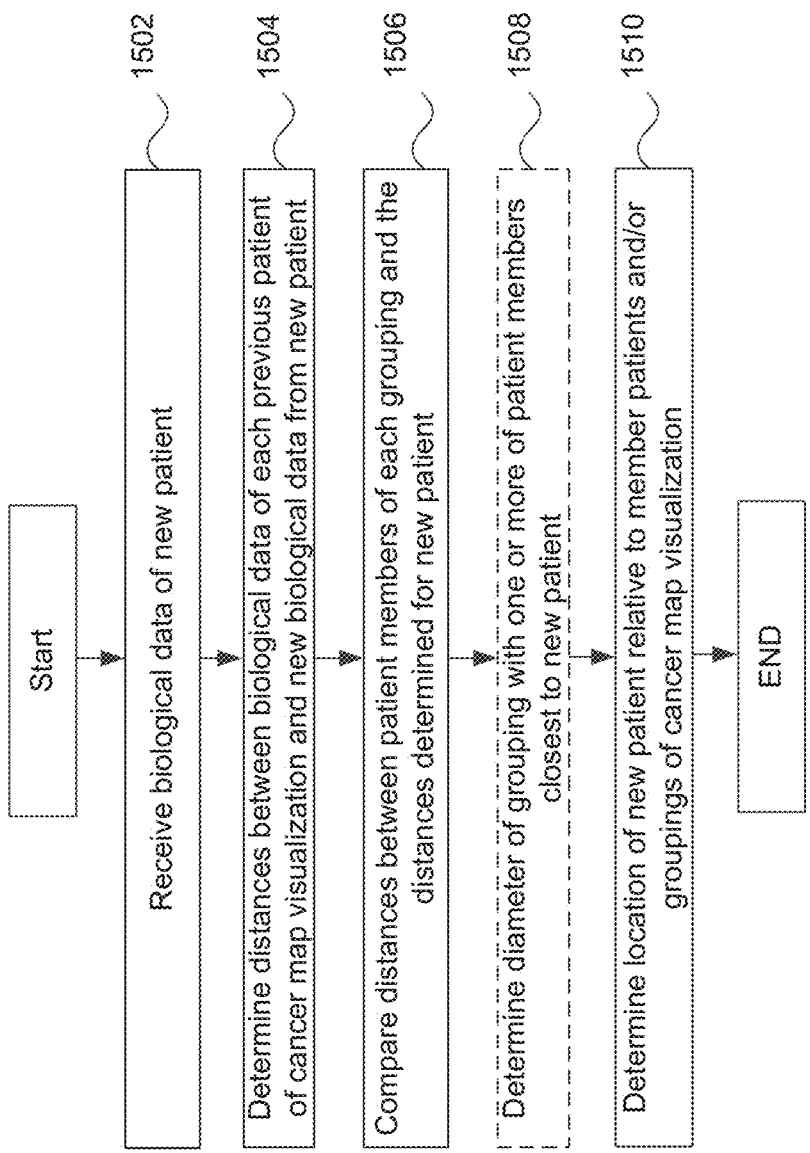
FIG. 15 is a flowchart of for positioning new patient data relative to the cancer map visualization in some embodiments.

FIG. 15 is a flowchart of for positioning new patient data relative to a cancer map visualization in some embodiments. In step 1502, new biological data of a new patient is received. In various embodiments, an input module 314 of an analysis server (e.g., analysis server 208 of FIGS. 1 and 2) may receive biological data of a new patient from a physician or medical facility that performed analysis of one or more samples to generate the biological data. The biological data may be any data that represents a biological data of the new patient including, for example, gene expressions, sequencing information, or the like.

In some embodiments, the analysis server 208 may comprise a new patient distance module and a location engine. In step 1504, the new patient distance module determines distances between the biological data of each patient of the cancer map visualization 1600 and the new biological data from the new patient. For example, the previous biological data that was utilized in the generation of the cancer map visualization 1600 may be stored in mapped data structures. Distances may be determined between the new biological data of the new patient and each of the previous patient's biological data in the mapped data structure.

In some embodiments, the analysis server 208 may comprise a new patient distance module and a location engine. In step 1504, the new patient distance module determines distances between the biological data of each patient of the cancer map visualization 1600 and the new biological data from the new patient. For example, the previous biological data that was utilized in the generation of the cancer map visualization 1600 may be stored in mapped data structures. Distances may be determined between the new biological data of the new patient and each of the previous patient's biological data in the mapped data structure.

It will be appreciated that distances may be determined in any number of ways using any number of different metrics or functions. Distances may be determined between the biological data of the previous patients and the new patients. For example, a distance may be determined between a first gene expression measurement of the new patient and each (or a subset) of the first gene expression measurements of the previous patients (e.g., the distance between G1 of the new patient and G1 of each previous patient may be calculated). Distances may be determined between all (or a subset of) other gene expression measurements of the new patient to the gene expression measurements of the previous patients.

In various embodiments, a location of the new patient on the cancer map visualization 1600 may be determined relative to the other member patients utilizing the determined distances.

In step 1506, the new patient distance module may compare distances between the patient members of each grouping to the distances determined for the new patient. The new patient may be located in the grouping of patient members that are closest in distance to the new patient. In some embodiments, the new patient location may be determined to be within a grouping that contains the one or more patient members that are closest to the new patient (even if other members of the grouping have longer distances with the new patient). In some embodiments, this step is optional.

In various embodiments, a representative patient member may be determined for each grouping. For example, some or all of the patient members of a grouping may be averaged or otherwise combined to generate a representative patient member of the grouping (e.g., the distances and/or biological data of the patient members may be averaged or aggregated). Distances may be determined between the new patient biological data and the averaged or combined biological data of one or more representative patient members of one or more groupings. The location engine may determine the location of the new patient based on the distances. In some embodiments, once the closest distance between the new patient and the representative patient member is found, distances may be determined between the new patient and the individual patient members of the grouping associated with the closest representative patient member.

In optional step 1508, a diameter of the grouping with the one or more of the patient members that are closest to the new patient (based on the determined distances) may be determined. In one example, the diameters of the groupings of patient members closest to the new patient are calculated. The diameter of the grouping may be a distance between two patient members who are the farthest from each other when compared to the distances between all patient members of the grouping. If the distance between the new patient and the closest patient member of the grouping is less than the diameter of the grouping, the new patient may be located within the grouping. If the distance between the new patient and the closest patient member of the grouping is greater than the diameter of the grouping, the new patient may be outside the grouping (e.g., a new grouping may be displayed on the cancer map visualization with the new patient as the single patient member of the grouping). If the distance between the new patient and the closest patient member of the grouping is equal to the diameter of the grouping, the new patient may be placed within or outside the grouping.

It will be appreciated that the determination of the diameter of the grouping is not required in determining whether the new patient location is within or outside of a grouping. In various embodiments, a distribution of distances between member patients and between member patients and the new patient is determined. The decision to locate the new patient within or outside of the grouping may be based on the distribution. For example, if there is a gap in the distribution of distances, the new patient may be separated from the grouping (e.g., as a new grouping). In some embodiments, if the gap is greater than a preexisting threshold (e.g., established by the physician, other user, or previously programmed), the new patient may be placed in a new grouping that is placed relative to the grouping of the closest member patients. The process of calculating the distribution of distances of candidate member patients to determine whether there may be two or more groupings may be utilized in generation of the cancer map visualization (e.g., in the process as described with regard to FIG. 12). It will be appreciated that there may be any number of ways to determine whether a new patient should be included within a grouping of other patient members.

In step 1510, the location engine determines the location of the new patient relative to the member patients and/or groupings of the cancer map visualization. The new location may be relative to the determined distances between the new patient and the previous patients. The location of the new patient may be part of a previously existing grouping or may form a new grouping.

In some embodiments, the location of the new patient with regard to the cancer map visualization may be performed locally to the physician. For example, the cancer map visualization 1400 may be provided to the physician (e.g., via digital device). The physician may load the new patient's biological data locally and the distances may be determined locally or via a cloud-based server. The location(s) associated with the new patient may be overlaid on the previously existing cancer map visualization either locally or remotely.

Those skilled in the art will appreciate that, in some embodiments, the previous state of the cancer map visualization (e.g., cancer map visualization 1400) may be retained or otherwise stored and a new cancer map visualization generated utilizing the new patient biological data (e.g., in a method similar to that discussed with regard to FIG. 12). The newly generated map may be compared to the previous state and the differences may be highlighted thereby, in some embodiments, highlighting the location(s) associated with the new patient. In this way, distances may be not be calculated as described with regard to FIG. 15, but rather, the process may be similar to that as previously discussed.

Figure 16:
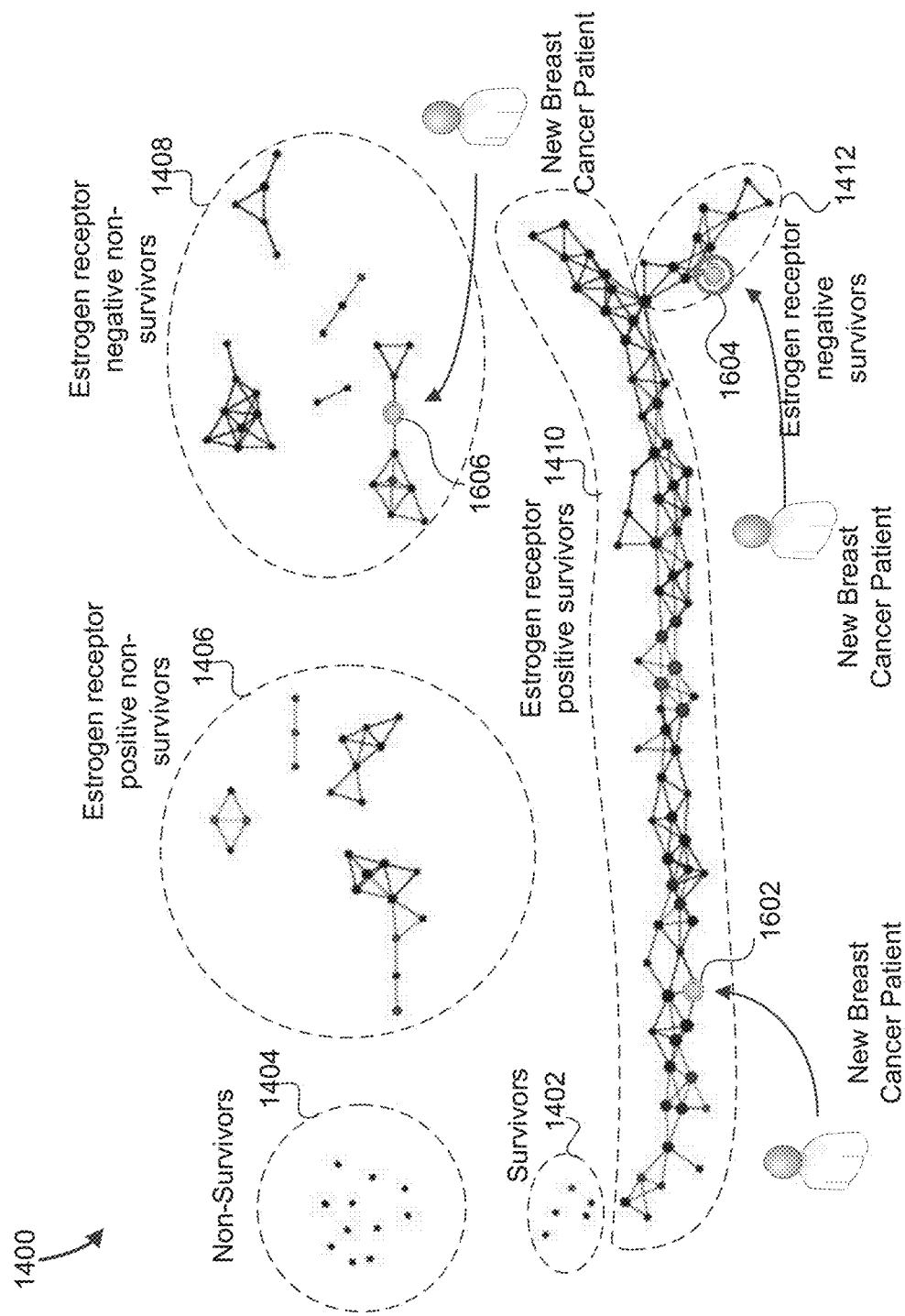
FIG. 16 is an example visualization displaying the cancer map including positions for three new cancer patients in some embodiments.

FIG. 16 is an example visualization displaying the cancer map including positions for three new cancer patients in some embodiments. The cancer map visualization 1400 comprises groupings and interconnections that are associated with different clinical outcomes as discussed with regard to FIG. 14. All or some of the clinical outcomes may be associated with the biological data that generated the cancer map visualization 1400. The cancer map visualization 1400 includes different groupings associated with survivors 1402, groupings associated with non-survivors 1404, estrogen receptor positive non-survivors 1406, estrogen receptor negative non-survivors 1408, estrogen receptor positive survivors 1410, and estrogen receptor negative survivors 1412.

The cancer map visualization 1400 includes three locations for three new breast cancer patients. The breast cancer patient location 1602 is associated with the clinical outcome of estrogen receptor positive survivors. The breast cancer patient location 1604 is associated with the clinical outcome of estrogen receptor negative survivors. Unfortunately, breast cancer patient location 1606 is associated with estrogen receptor negative non-survivors. Based on the locations, a physician may consider different diagnoses, prognoses, treatments, and therapies to maintain or attempt to move the breast cancer patient to a different location utilizing the cancer map visualization 1400.

In some embodiments, the physician may assess the underlying biological data associated with any number of member patients of any number of groupings to better understand the genetic similarities and/or dissimilarities. The physician may utilize the information to make better informed decisions.

The patient location 1604 is highlighted on the cancer map visualization 1400 as active (e.g., selected by the physician). It will be appreciated that the different locations may be of any color, size, brightness, and/or animated to highlight the desired location(s) for the physician. Further, although only one location is identified for three different breast cancer patients, any of the breast cancer patients may have multiple locations indicating different genetic similarities.

It will be appreciated that the cancer map visualization 1400 may be updated with new information at any time. As such, as new patients are added to the cancer map visualization 1400, the new data updates the visualization such that as future patients are placed in the map, the map may already include the updated information. As new information and/or new patient data is added to the cancer map visualization 1400, the cancer map visualization 1400 may improve as a tool to better inform physicians or other medical professionals.

In various embodiments, the cancer map visualization 1400 may track changes in patients over time. For example, updates to a new patient may be visually tracked as changes in are measured in the new patient's biological data. In some embodiments, previous patient data is similarly tracked which may be used to determine similarities of changes based on condition, treatment, and/or therapies, for example. In various embodiments, velocity of change and/or acceleration of change of any number of patients may be tracked over time using or as depicted on the cancer map visualization 1400. Such depictions may assist the treating physician or other personnel related to the treating physician to better understand changes in the patient and provide improved, current, and/or updated diagnoses, prognoses, treatments, and/or therapies.

Figure 17:
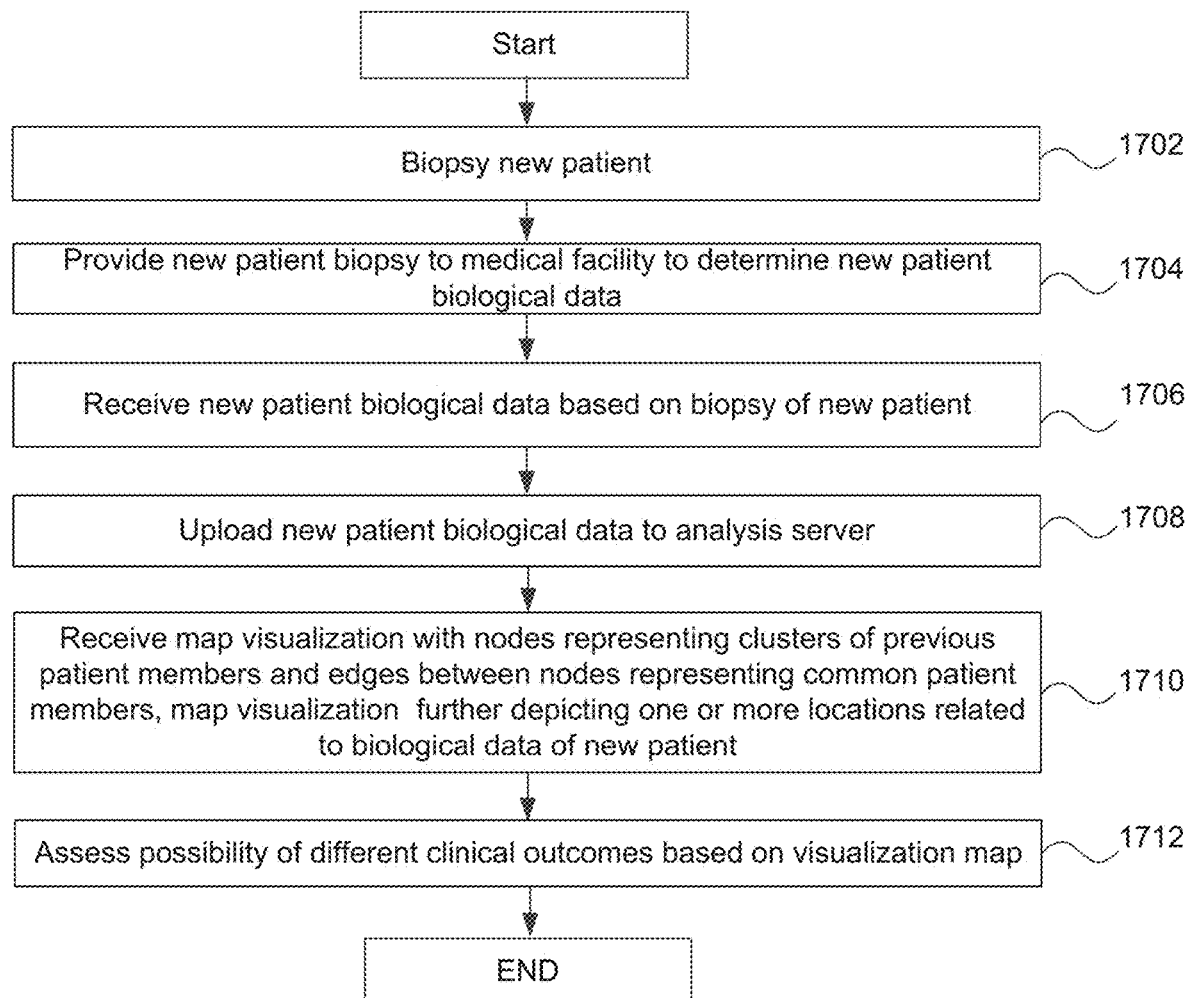
FIG. 17 is a flowchart of utilization the visualization and positioning of new patient data in some embodiments

FIG. 17 is a flowchart of utilization the visualization and positioning of new patient data in some embodiments. In various embodiments, a physician may collect amounts of genomic information from tumors removed from a new patient, input the data (e.g., upload the data to an analysis server), and receive a map visualization with a location of the new patient. The new patient's location within the map may offer the physician new information about the similarities to other patients. In some embodiments, the map visualization may be annotated so that the physician may check the outcomes of previous patients in a given region of the map visualization are distributed and then use the information to assist in decision-making for diagnosis, treatment, prognosis, and/or therapy.

In step 1702, a medical professional or other personnel may remove a sample from a patient. The sample may be of a tumor, blood, or any other biological material. In one example, a medical professional performs a tumor excision. Any number of samples may be taken from a patient.

In step 1704, the sample(s) may be provided to a medical facility to determine new patient biological data. In one example, the medical facility measures genomic data such as gene expression of a number of genes or protein levels.

In step 1706, the medical professional or other entity associated with the medical professional may receive the new patient biological data based on the sample(s) from the new patient. In one example, a physician may receive the new patient biological data. The physician may provide all or some of the new patient biological data to an analysis server over the Internet (e.g., the analysis server may be a cloud-based server). In some embodiments, the analysis server is the analysis server 208 of FIG. 1. In some embodiments, the medical facility that determines the new patient biological data provides the biological data in an electronic format which may be uploaded to the analysis server. In some embodiments, the medical facility that determines the new patient biological data (e.g., the medical facility that measures the genomic data) provide the biological data to the analysis server at the request of the physician or others associated with the physician. It will be appreciated that the biological data may be provided to the analysis server in any number of ways.

The analysis server may be any digital device and may not be limited to a digital device on a network. In some embodiments, the physician may have access to the digital device. For example, the analysis server may be a table, personal computer, local server, or any other digital device.

Once the analysis server receives the biological data of the new patient, the new patient may be localized in the map visualization and the information may be sent back to the physician in step 1708. The visualization may be a map with nodes representing clusters of previous patient members and edges between nodes representing common patient members. The visualization may further depict one or more locations related to the biological data of the new patient.

The map visualization may be provided to the physician or other associated with the physician in real-time. For example, once the biological data associated with the new patient is provided to the analysis server, the analysis server may provide the map visualization back to the physician or other associated with the physician within a reasonably short time (e.g., within seconds or minutes). In some embodiments, the physician may receive the map visualization over any time.

The map visualization may be provided to the physician in any number of ways. For example, the physician may receive the map visualization over any digital device such as, but not limited to, an office computer, Ipad, tablet device, media device, smartphone, e-reader, or laptop.

In step 1710, the physician may assess possible different clinical outcomes based on the map visualization. In one example, the map-aided physician may make decisions on therapy and treatments depending on where the patient lands on the visualization (e.g., survivor or non-survivor). The map visualization may include annotations or labels that identify one or more sets of groupings and interconnections as being associated with one or more clinical outcomes. The physician may assess possible clinical outcomes based on the position(s) on the map associated with the new patient.

As described above, interesting continuous functions on a metric space (e.g., a similarity space) allow the application of systems and methods described herein. In various embodiments, functions may be performed on data within the metric space to project data into the reference space. Having the function(s) to project the data from the metric space to the similarity space (i.e., a lens function) dependent on a small number of coordinates (e.g., counting a number of uses of a small collection of words) is a fairly simple way to achieve continuity in most metrics, and the resulting lenses may be suitable for interpolation. However, such lenses may be of limited use on high-dimensional data, and if the interesting features of the space were captured in those few dimensions, there may be no point keeping the rest of the coordinates.

In practice, lenses which incorporate intrinsic properties of the metric (e.g., the function on the data to generate the metric space), such as density or centrality, are more likely to capture features of the space, absent special knowledge of the particular data set, than functions which depend on a few coordinates. One example method of dimensionality reduction (which is a way to think of a small collection of lenses applied jointly) are variants of "Stochastic Neighbor Embedding" (aka SNE). The underlying intuition in stochastic neighbor embedding is to map the high dimensional space to points in a low-dimensional Euclidean space, typically two or three dimensions, define a potential function on the points which penalizes them for being either closer or farther apart in the embedding than they are in the high-dimensional space, and move points around to minimize the potential. This may be effectively like a graph-layout problem, where a (potentially) high-dimensional space, an arbitrary combinatorial graph, is to be faithfully represented by a two-dimensional picture.

Some example methods amount to computing a global potential and then optimizing the placement by the same optimization techniques used in applications of artificial neural network. These methods produce very nice pictures and the lenses can be remarkably effective with TDA, but they may be computationally expensive. Some embodiments described herein allow for the use of less computationally expensive layout mechanisms and methods.

Figure 18:
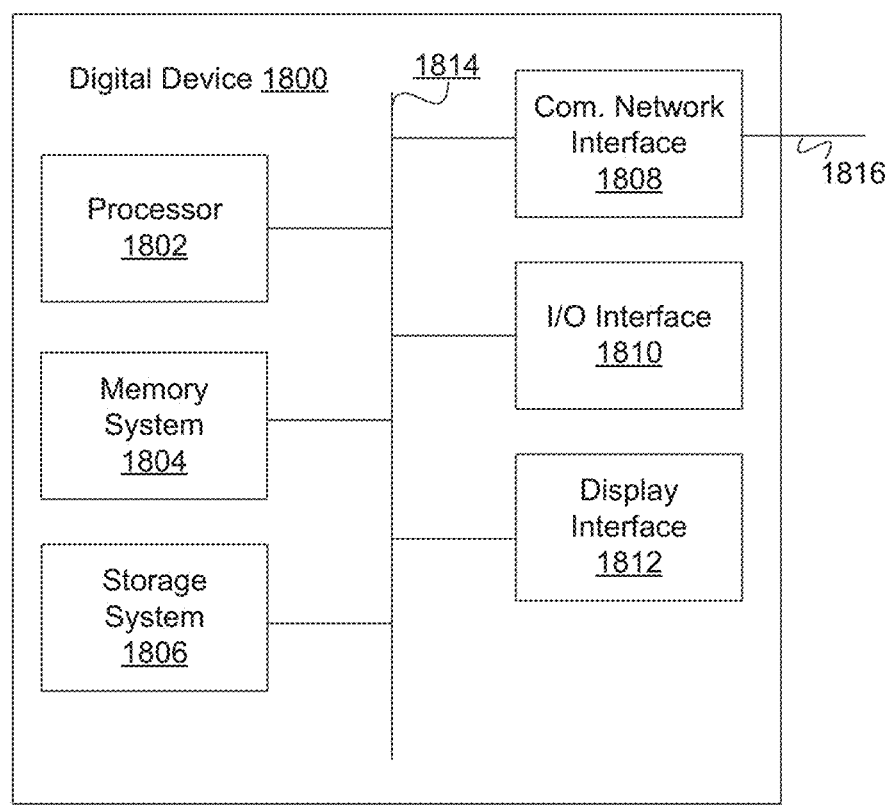
FIG. 18 is an example digital device in some embodiments.

FIG. 18 is a block diagram of an example digital device 1800. The digital device 1800 comprises a processor 1802, a memory system 1804, a storage system 1806, a communication network interface 1808, an I/O interface 1810, and a display interface 1812 communicatively coupled to a bus 1814. The processor 1802 may be configured to execute executable instructions (e.g., programs). In some embodiments, the processor 1802 comprises circuitry or any processor capable of processing the executable instructions.

The memory system 1804 is any memory configured to store data. Some examples of the memory system 1804 are storage devices, such as RAM or ROM. The memory system 1804 can comprise the ram cache. In various embodiments, data is stored within the memory system 1804. The data within the memory system 1804 may be cleared or ultimately transferred to the storage system 1806.

The storage system 1806 is any storage configured to retrieve and store data. Some examples of the storage system 1806 are flash drives, hard drives, optical drives, and/or magnetic tape. In some embodiments, the digital device 1800 includes a memory system 1804 in the form of RAM and a storage system 1806 in the form of flash data. Both the memory system 1804 and the storage system 1806 comprise computer readable media which may store instructions or programs that are executable by a computer processor including the processor 1802.

The communication network interface (com. network interface) 1808 can be coupled to a communication network (e.g., communication network 204) via the link 1816. The communication network interface 1808 may support communication over an Ethernet connection, a serial connection, a parallel connection, or an ATA connection, for example. The communication network interface 1808 may also support wireless communication (e.g., 1802.11 a/b/g/n, WiMax). It will be apparent to those skilled in the art that the communication network interface 1808 can support many wired and wireless standards.

The optional input/output (I/O) interface 1810 is any device that receives input from the user and output data. The optional display interface 1812 is any device that may be configured to output graphics and data to a display. In one example, the display interface 1812 is a graphics adapter.

It will be appreciated by those skilled in the art that the hardware elements of the digital device 1800 are not limited to those depicted in FIG. 18. A digital device 1800 may comprise more or less hardware elements than those depicted. Further, hardware elements may share functionality and still be within various embodiments described herein. In one example, encoding and/or decoding may be performed by the processor 1802 and/or a co-processor located on a GPU.

In various embodiments, data points of a data set or nodes in a graph are automatically grouped (i.e., "autogrouped"). The groupings may be approximations of a possible maxima (e.g., a best maxima) of a given scoring function that scores possible partitions of the original object (i.e., a collection of data points or a collection of nodes of a graph).

Autogrouping may be utilized to automatically find a collection of subsets of some set Y that share one or more given properties. In one example, autogrouping may be utilized to find a collection of subsets that is a partition of Y where Y is a subset of a finite metric space X or nodes in a graph. However, it will be appreciated, in some embodiments, that the methodology described herein has no such requirement.

In various embodiments, a selection of possible partitions of a data set (e.g., original data set or nodes in a visualization) may be identified and scored. A partition is a collection of disjoint subsets of a given set. The union of the subsets of each partition equal the entire original set. A hierarchical clustering method may be utilized on the original object Y to create a family of partitions of Y.

A first scoring function may score the subsets (i.e., to generate a Q_Subset score), a second scoring function may score the partitions (i.e., to generate a Q_Partition score), and a third scoring function may score the roots of trees coming from the hierarchical clustering method (i.e., to generate a Q_Max score). The highest scoring partition based on any one or a combination of these scoring functions may be found for the family. The first and/or second scoring functions may be any function or combination of functions that may be able to be scored. Example scoring functions are further discussed herein.

In some embodiments, autogrouping is the process in which a highest scoring partition is identified. The highest scoring partition may be the maximum of the given scoring function(s) of any number of subsets from any number of partitions.

In some embodiments, a limited number of partitions of all possible partitions may be generated. In fact, in some cases, the result may be better if the scorer is imperfect, as at least some hierarchical clustering algorithms generally avoid partitions with large numbers of miscellaneous singletons or other ugly sets which might actually be the global extreme for such a scoring function. It will be appreciated that the hierarchical clustering process may serve to condition data to only present 'good alternatives,' and so can improve the effectiveness of some scorers.

Since the number of partitions for a data set is high (e.g., $(N/\log(N))^N$), it may be impractical to generate every possible partition. Unfortunately, most local improvement methods can easily get stuck. Some techniques to generate a subset of partitions involve attempting to maximize a modularity score over graph partitions by making an initial partition and then making local changes (e.g., moving nodes from one partition to another). Modularity is the fraction of edges that fall within given groups minus the expected such fraction if edges were distributed at random. Unfortunately, the modularity measure Q score may exhibit extreme degeneracies because it admits an exponential number of distinct high-scoring solutions and typically lacks a clear global maximum. Another approach to maximizing functions on partitions by local methods is to use probabilistic techniques such as simulated annealing. At least some embodiments described herein offer a deterministic alternative that is applicable to a wide range of scoring functions.

Subsets in one or more different partitions of those generated may be selected based, at least in part, on Q scores, further described herein. A new partition including the selected subsets may be generated or, if all of the selected subsets are already part of a generated partition, then the preexisting partition may be selected.

FIGS. 19a-d depict an example of determining a partition based on scoring for autogrouping in some embodiments. In an example, there is a fixed space, S, of finite size. The nature of the space may be relevant only in so far as there is a way of clustering the space and scoring subsets. Referring to a graph G on S indicates a graph whose nodes are a collection of subsets where a node is connected to another node if and only if the two nodes have points in common. A partition includes one or more subsets. Each of the one or more subsets include all of the element(s) of S. For example, partition 1902 is a partition that includes subsets of all elements of S. Subsets 1904*a-e* include all elements of S. A union of all of the subsets 1904*a-e* is the partition 1902.

Figure 19A:
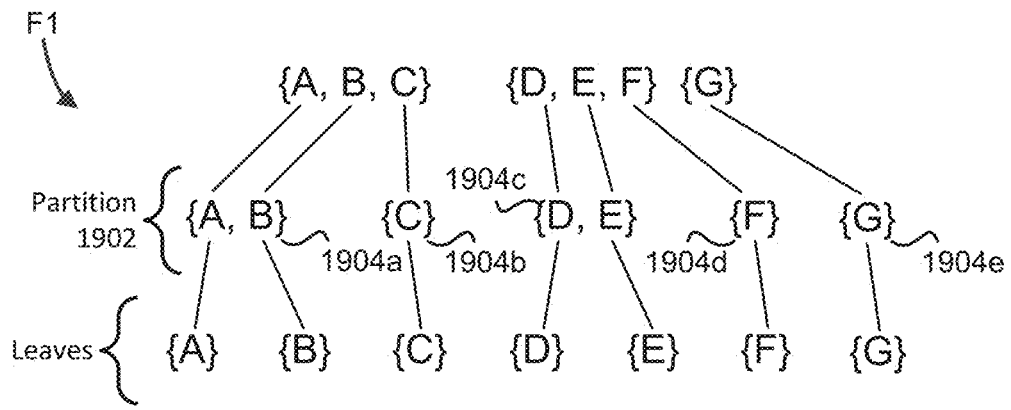
FIGS. 19a-d depict an example of determining a partition based on scoring for autogrouping in some embodiments.
Figure 19B:
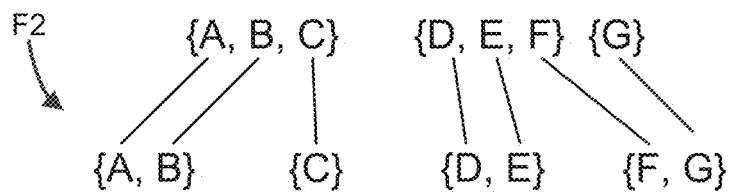
Figure 19C:
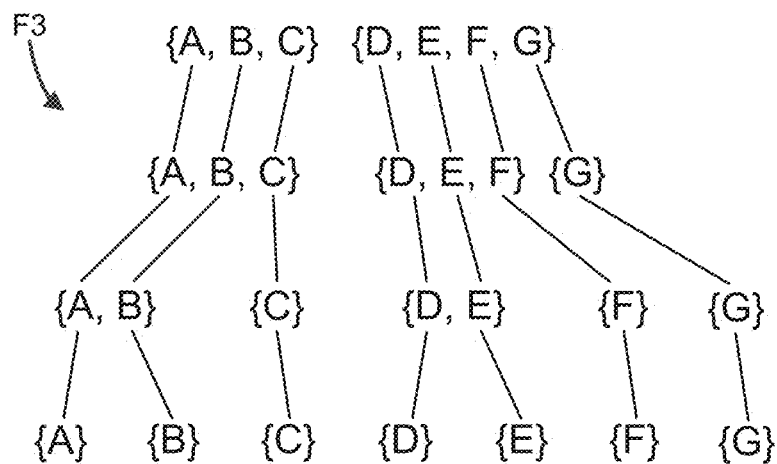

A forest F on S is a graph on S. A forest F is 'atomic' if every leaf in F is a singleton (e.g., a set with one member). FIG. 19*a* (i.e., F1) is an atomic forest because every leaf in F1 as depicted in FIG. 19*a* is a singleton. It will be appreciated that FIG. 19*b* (i.e., F2) is not an atomic forest since every leaf in F2 as depicted in FIG. 19*b* is not a singleton. For example, F2 includes leaves {A,B}, {D,E}, and {F,G}.

There is a partition R of S (in F1, {a, b, c}, {d, e, f}, {g}), called the roots, such that every set in F is reachable by a unique path from a root. N in F is either a leaf (e.g., a singleton in an atomic forest) or it is connected to nodes which form a partition (e.g., {a, b, c}→{a,b} and {c} in F1) of N. For a non-leaf node N we denote by C(N) the children of N. Notice the children of a leaf, namely C(leaf) is empty. We say that F' extends F if F and F' have the same leaves and every node in F is a node in F'. If the two forests are not equal, then F' contains a node which is the union of one or more roots in F. Example F3 (FIG. 19*c*) extends F1 (FIG. 19*a*).

Figure 19D:
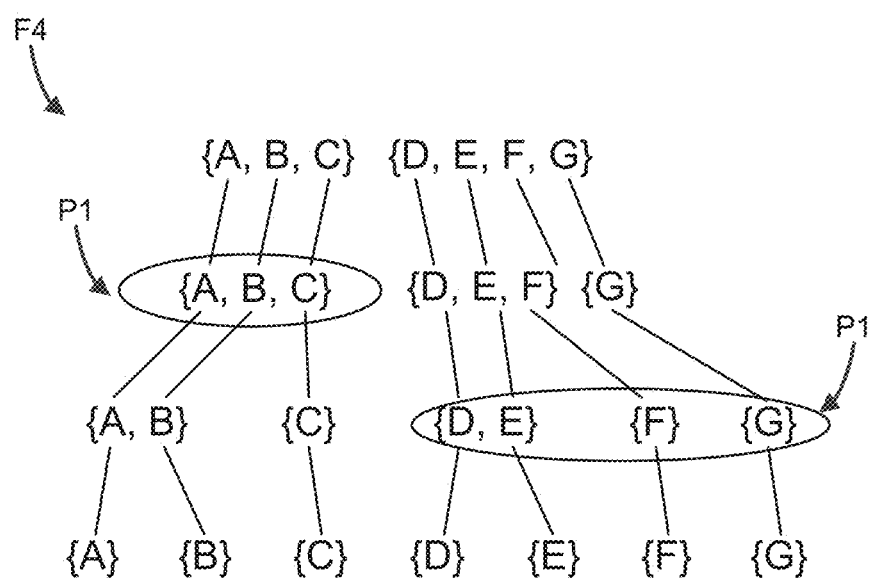

Partition P on S is subordinate to F1 if and only if every element of P is in F1. The circled partition P1 of F4 depicted in FIG. 19*d*, is an example of a subordinate partition {e.g., {a, b, c}, {d,e}, {f}, and {g}} to F1.

Singletons(S) are denoted as the partition formed by taking {{x}|x in S}. That is, in the example in FIG. 19*d*, Singletons({a, b, c, d, e, f, g})={{a}, {b}, {c}, {d}, {e}, {f}, {g}}. This is the same as the set of leaves of an atomic forest. Let U(P), where P is any collection of subsets of S, denote the union of all the elements of P. U(Singletons(S))==S.

Partition P' on S is coarser than another partition P on S if and only if every element x' in P' is the union of elements x in P. In various embodiments, every partition on S is coarser than Singletons(S), and {S} is coarser than every partition on S. For instance, {{a, b, c}, {d, e, f}, {g}} is a coarser partition than {{a,b}, {c}, {d,e}, {f}, {g}}.

Figure 20:
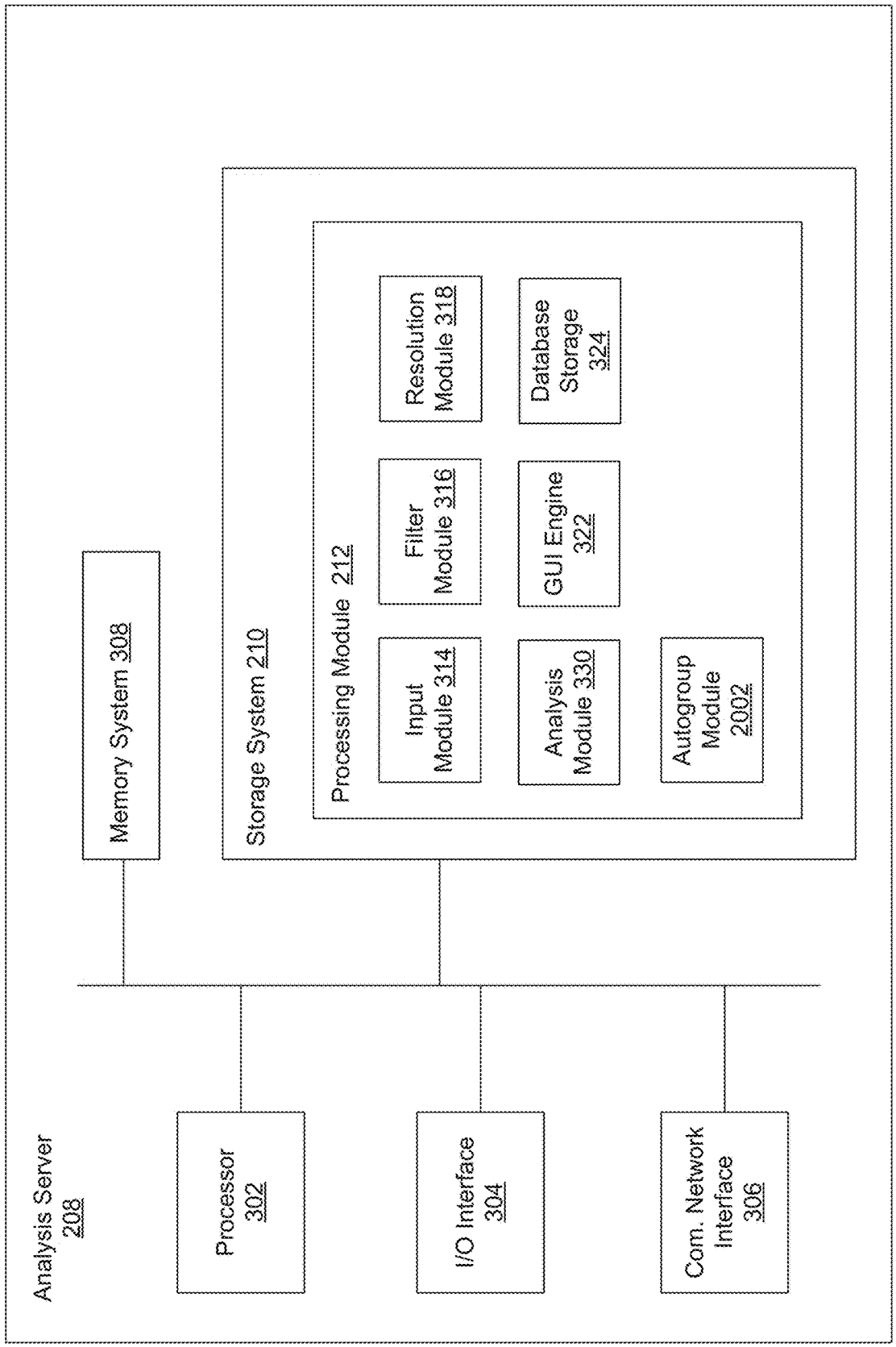
FIG. 20 is a block diagram of an example analysis server.

FIG. 20 is a block diagram of an example analysis server 208 including an autogroup module 2002. The example analysis server 208 depicted in FIG. 20 may be similar to the example analysis server 208 depicted in FIG. 2. In example embodiments, the analysis server 208 comprises a processor 302, input/output (I/O) interface 304, a communication network interface 306, a memory system 308, and a storage system 310.

The storage system 310 comprises a plurality of modules utilized by embodiments of the present invention. A module may be hardware (e.g., an ASIC), software (e.g., including instructions executable by a processor), or a combination of both. In one embodiment, the storage system 310 comprises a processing module 312 which comprises an input module 314, a filter module 316, a resolution module 318, an analysis module 320, a visualization engine 322, a database storage 324, and an autogroup module 2002. Alternative embodiments of the analysis server 208 and/or the storage system 310 may comprise more, less, or functionally equivalent components and modules.

The input module 314 may be configured to receive commands and preferences from the user device 202*a*. In various examples, the input module 314 receives selections from the user which will be used to perform the analysis. The output of the analysis may be an interactive visualization.

The input module 314 may provide the user a variety of interface windows allowing the user to select and access a database, choose fields associated with the database, choose a metric, choose one or more filters, and identify resolution parameters for the analysis. In one example, the input module 314 receives a database identifier and accesses a large multi-dimensional database. The input module 314 may scan the database and provide the user with an interface window allowing the user to identify an ID field. An ID field is an identifier for each data point. In one example, the identifier is unique. The same column name may be present in the table from which filters are selected. After the ID field is selected, the input module 314 may then provide the user with another interface window to allow the user to choose one or more data fields from a table of the database.

Although interactive windows may be described herein, it will be appreciated that any window, graphical user interface, and/or command line may be used to receive or prompt a user or user device 202*a* for information.

The filter module 316 may subsequently provide the user with an interface window to allow the user to select a metric to be used in analysis of the data within the chosen data fields. The filter module 316 may also allow the user to select and/or define one or more filters.

The resolution module 318 may allow the user to select a resolution, including filter parameters. In one example, the user enters a number of intervals and a percentage overlap for a filter.

The analysis module 320 may perform data analysis based on the database and the information provided by the user. In various embodiments, the analysis module 320 performs an algebraic topological analysis to identify structures and relationships within data and clusters of data. It will be appreciated that the analysis module 320 may use parallel algorithms or use generalizations of various statistical techniques (e.g., generalizing the bootstrap to zig-zag methods) to increase the size of data sets that can be processed. The analysis is further discussed in FIG. 8. It will be appreciated that the analysis module 320 is not limited to algebraic topological analysis but may perform any analysis.

The visualization engine 322 generates an interactive visualization including the output from the analysis module 320. The interactive visualization allows the user to see all or part of the analysis graphically. The interactive visualization also allows the user to interact with the visualization. For example, the user may select portions of a graph from within the visualization to see and/or interact with the underlying data and/or underlying analysis. The user may then change the parameters of the analysis (e.g., change the metric, filter(s), or resolution(s)) which allows the user to visually identify relationships in the data that may be otherwise undetectable using prior means. The interactive visualization is further described in FIGS. 9-11.

The database storage 324 is configured to store all or part of the database that is being accessed. In some embodiments, the database storage 324 may store saved portions of the database. Further, the database storage 324 may be used to store user preferences, parameters, and analysis output thereby allowing the user to perform many different functions on the database without losing previous work.

The autogroup module 2002 is configured to autogroup data points of a data set or nodes in a graph. As discussed herein, the groupings may be approximations of possible maxima of a given scoring function that scores possible partitions of the original data object (e.g., a collection of data points or a collection of nodes of a graph). The autogroup module 2002 may, in some embodiments, perform autogrouping of nodes of a graph (whether a visualization is generated or not). In various embodiments, the autogroup module 2002 may perform autogrouping for reference space open cover generation. The autogroup module 2002 may autogroup any number of data points, sets of data points, representations, and/or the like. The autogroup module 2002 is further discussed in FIG. 21.

It will be appreciated that that all or part of the processing module 212 may be at the user device 202a or the database storage server 206. In some embodiments, all or some of the functionality of the processing module 312 may be performed by the user device 202a.

Figure 21:
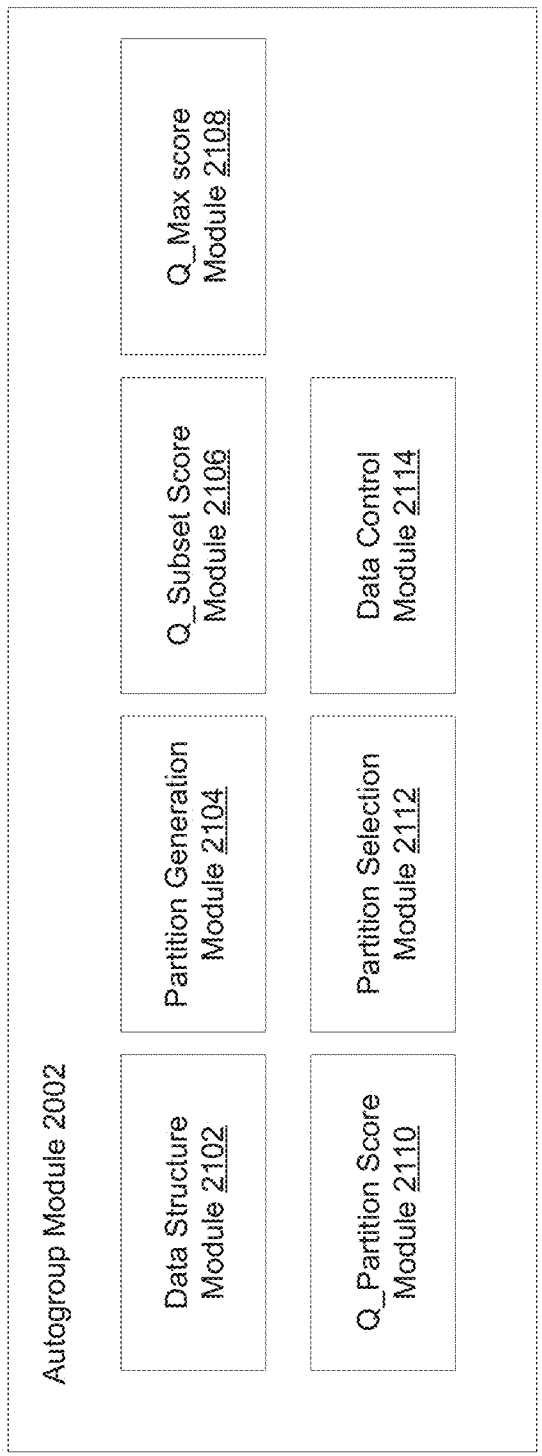
FIG. 21 depicts an example autogroup module in some embodiments.

FIG. 21 depicts an example autogroup module 2002 in some embodiments. An autogroup module 2002 may comprise a data structure module 2102, a partition generation module 2104, scoring function modules (e.g., a Q_subset score module 2106, a Q_max score module 2108, a Q_partition score module 2110), a partition selection module 2112, and a data control module 2114. Although the scoring function modules are discussed as including three modules, each performing a different scoring function, it will be appreciated that there may be any number of scoring function modules performing any number of scoring functions (e.g., one module performing a single scoring function capable of generating any number or type of scores). For example, the scoring functions may generate and/or maximize metric values of any number of metric functions.

In various embodiments, the data structure module 2102 receives data including a plurality of sets of data. The data may be received from any number of digital devices.

The partition generation module 2104 (e.g., a "dumper") forms a forest F utilizing the plurality of sets of data received by the data structure module 2102. For example, the partition generation module 2104 may generate a first partition of a forest F using the data received by the data structure module 2102. In some embodiments, the first partition may include leaves that are singletons of all elements from the data. In various embodiments, the first partition may include any number of sets of data. The first partition may include leaves for the forest, singletons, roots, sets of plurality of elements, and/or the like.

The partition generation module 2104 may generate the second partition of the forest F using the first partition. For example, the second partition may include at least one union of at least two sets of the first partition. Subsequent partitions may be generated in a similar fashion (e.g., based, at least in part, on including at least one union of at least two sets from the previous partition).

The partition generation module 2104 may generate an entire forest F before scoring partitions (or sets of partitions). For example, the partition generation module 2104 may generate the entire forest F before any or all of the scoring function modules score all or parts of partitions of the forest F.

In some embodiments, the partition generation module 2104 may generate the entire forest F while scoring is performed or in series with partition scoring (e.g., scoring of sets of partitions). For example, the partition generation module 2104 may generate the entire forest F while any or all of the scoring function modules score all or parts of partitions of the forest F. In another example, the partition generation module 2104 may generate one or more partitions of the forest F and then any number of the scoring function modules may score the generated partitions before the partition generation module 2104 generates one or more additional partitions of the forest F.

In various embodiments, the partition generation module 2104 may generate a partition of a forest F based on, at least in part, scores by any number of scoring function modules of previously generated partition(s) (or sets of partition(s)) of the forest F.

It will be appreciated that the partition generation module 2104 may not generate the entire forest F but may rather terminate generating partitions of the forest F before the forest F is completed. The partition generation module 2104 may determine whether to build a new partition of the forest F based on any number of the previously generated partition(s) of the forest F and/or scoring associated with all or parts of previously generated partition(s).

As discussed herein, the partition generation module 2104 may not generate all possible sets of data and/or all possible partitions of the forest F.

It will be appreciated that the partition generation module 2104 may utilize any number of hierarchical clustering techniques with techniques described herein. In one example, data and/or nodes are joined by epsilon (if 2 data subsets or nodes are within distance epsilon of each other then they are joined together). While this example standard technique has traditional limitations ("fixed epsilon") whereby a single epsilon may be unable to break up a space in a preferable manner, by scoring each subset of a partition, we can select subsets across a forest to identify and/or generate a selected partition (e.g., by autogrouping subsets of a plurality of partitions).

One example of a hierarchical clustering technique, KNN on a finite metric space X is to compute the K nearest neighbors for each point of a network graph (e.g., a visualized or non-visualized graph that includes nodes that may be coupled to one or more other nodes of the graph) with, for example, K=50. The partition generation module 2104 may start with INITIAL( ) being Singletons(X). Then at each step for 1<=k<=50, the partition generation module 2104 may connect x to y provided x and y are in the symmetric k nearest neighbors of one another. Note that if KNN(P, k) returns P for k<50, the partition generation module 2104 may bump k and try again instead of concluding that P is stable.

Another hierarchical clustering technique embodiment is defined on a weighted graph G (with positive weights) on a point set S. This hierarchical clustering technique is parameterized by a pre-determined real number delta where 1>delta>0. The partition generation module 2104 starts with delta=0 so INITIAL( ) being Singletons(S). For each partition P, we define wt(p, q), for p!=q in P, to be the sum of edge weights between the nodes in the graph which are a part of the subset p and those in the subset q in G, divided by |p|*|q|. The partition generation module 2104 is configured to take a partition P and make a new partition P' by joining all pairs of subsets (a, b) (where a, b are subsets in the partition P) when wt(a, b)>=delta*max(wt(p, q)) where the max is over all pairs of subsets p and q in the partition P.

There are any number of techniques for hierarchical clustering and any of them can be combined with a scoring function that satisfies example constraints on the scoring functions discussed herein.

The autogroup module 2002 includes the Q_Subset score module 2106, the Q_Max score module 2108, and the Q_Partition score module 2110 which may utilize three scoring functions, respectively. The Q_Subset score module 2106 calculates a Q_Subset score for subsets of one or more partitions. The Q_Max score module 2108 calculates a Q_Max score based on the Q_Subset score (e.g., calculates a maximum score for a partition based on the Q_Subset score) for the subsets. The Q_Partition score module 2110 calculates a Q_Partition score for two or more partitions of the forest utilizing at least the Q_Subset Score for the subsets.

In various embodiments, the Q_Subset score module 2106 calculates Q_Subset scores (e.g., one for each subset of a partition). A function Q is defined on subsets of the space S and scores the properties which are to be grouped together in the autogrouping process. For instance, in some embodiments, the Q_Subset score is a modularity score on a graph (so S are the nodes in the graph). The partition selection module 2112 may examine the data structure for a partition of the graph S with maximum modularity score(s).

Modularity is one measure of the structure of networks or graphs that is appreciated by those skilled in the art. The modularity score may be used to measure strength of division of a network of nodes (e.g., modules, groups, clusters, or communities). Modularity may be used in optimization methods for detecting community structure in networks. In one example, modularity is the fraction of edges of nodes in a graph that fall within a given group minus the expected such fraction if edges were distributed at random. It will be appreciated that there are many different methods for calculating modularity.

In one example, randomization of edges preserves a degree of each vertex. Assume a graph with n nodes and m links (edges) such that the graph can be partitioned into two communities using a membership variable s. If a node v belongs to community 1, $S_v=1$, or if v belongs to community 2, $S_v=-1$. An adjacency matrix for an undirected network may be represented by A, where $A_{vw}=0$ indicates there are no edges (no interaction) between nodes v and w. $A_{vw}=1$ indicates there are $A_{vw}=1$ indicates there is an edge between the two.

Modularity Q may be defined as the fraction of edges that fall within group 1 or 2, minus the expected number of edges within groups 1 and 2 for a random graph with the same node degree distribution as the network.

In this example, an expected number of edges is determined using configuration models. The configuration model is a randomized realization of a particular network. Given a network with n nodes, where each node v has a node degree $k_v$, the configuration model cuts each edge into two halves, and then each half edge is rewired randomly with any other half edge in the network.

For this example, assume that the total number of half edges is $1_n$ $$l_n = \sum_v k_v = 2m$$

Two randomly nodes v and w with node degrees $k_v$ and $k_w$ respectively are selected and half edges rewired then the expectation of full edges between v and w is equal to (Full edges between v and w)/(total number of rewiring possibilities). The expected [Number of full edges between v and w]=$(k_v*k_w)/1_n=(k_v k_w)/2m$.

As a result, the actual number of edges between v and w minus expected number of edges between them is $A_{vw}-(k_v k_w)/2m$.

$$Q = \frac{1}{2m}\sum_{vw}\left[A_{vw} - \frac{k_v x k_w}{2m}\right]\frac{s_v s_w + 1}{2} = 2m$$

The equation above holds for partitioning into two communities only. Hierarchical partitioning (i.e. partitioning into two communities, then the two sub-communities further partitioned into two smaller sub communities only to maximize Q) is a possible approach to identify multiple communities in a network. The above equation can be generalized for partitioning a network into c communities.

$$Q = \sum_{vw}\left[\frac{A_{vw}}{2m} - \frac{k_v x k_w}{(2m)(2m)}\right]\delta(c_v, c_w) = \sum_{i=1}^{c}(e_{ij} - \alpha_i^2)$$

$e_{ij}$ is the fraction of edges with one end vertices in community i and the other in community j:

$$e_{ij} = \sum_{vw}\frac{A_{vw}}{2m}1_{vec_i}1_{vec_j}$$

$a_i$ is the fraction of ends of edges that are attached to vertices in community i:

$$\alpha_i = \frac{k_i}{2m} = \sum_j e_{ij}$$

The second scoring function, the Q_Partition score, may be an extension of the first scoring function Q to be defined on partitions of the space S. If the scoring function Q is defined on subsets of S, it can be extended to a partition function Q_Partition in various ways. One of the simplest ways to extend function Q to partitions is by defining Q_Partition (P) as the sum over p in P of Q(p) (e.g., for a partition P, Q_Partition (P)=sum_{subsets p in P} Q(p)).

In some embodiments, Q_Partition must have the following property: Let P be an arbitrary partition of a subset of S, let p belong to P, and let q be a partition of p. P(q) is defined to be the partition of obtained by replacing p in P with the elements of q. Then, in this example, Q_Partition must have the following property for all P, p, q as described above:

$$QP(P(q))>=QP(P) \text{ if and only if } QP(q)>=Q(\{p\}) \quad (1)$$

In some embodiments, function Q does not need to come from a set function in this case. Functions Q_Partition which satisfy property (1) are, by definition, stable partition functions. A class of such functions is described as follows.

Let Q be any real-valued function defined on the set of non-empty subsets of S. Let A(p, q) be any function defined on pairs of non-empty subsets such that p is a subset of q. If:

$$A(p,p)==1 \text{ and } A(p,q)*A(q,r)=A(p,r), \text{ for all legal } p,q,r \quad (2)$$

then we may extend the set function Q( ) to all partitions P by:

$$QP(P)=\text{sum } A(p,U(P))Q(p) \quad (3)$$

p in P

Note that all real numbers k, $A(p, q)==(|p|/|q|)^k$ satisfies this property. Moreover, k==0 implies A(p, q)==1.

(1) holds for Q defined in (3). If QP and QP' are stable partition functions, then so is x*QP+y*QP' for x, y>=0. We also refer to stable partition functions on S as "partition scoring functions" for F.

For any scoring function of the form (3), a monotonically increasing function f may be chosen from the real numbers to itself and replace Q by Q'( )=f(Q( )). In particular, if f( ) is 'sufficiently invertible' (e.g., A( ) and Q( ) are >=0 and f( ) is invertible on the non-negative reals). QP(P) may be defined by:

$$(3') \quad QP'(P) = f\text{-inverse}(\text{sum } A(p,U(P))f(Q(p)))  \quad (3')$$

p in P

Since f(QP(P)) satisfies (1) and f( ) is monotonically increasing, the QP' in (3') also satisfies (1) and extends Q( ) on subsets of S. Concretely, if A==1 and Q( )>=0 on sets, QP(P) may be defined to be the Euclidean norm of Q( ) on the individual elements of P, and still get a scoring function. Also can use the exponential function for f( ) without requiring Q to be non-negative.

In various embodiments, there may be extreme values under comparisons, using either <= or >=, for a function Q defined on partitions of subsets of S. Since Q may be replaced by −Q if the comparison is <=, it may be assumed without loss of generality that maximal values for Q (i.e., >=) are of interest. Specifically, a method for finding the F-subordinate partition on which Q is maximal, provided Q satisfies a simple property, is disclosed herein.

Given a scoring function Q_Partition on F, we can define a scoring function Q_max ( ) to be Q(p) if p is a leaf, and max(Q(p), Qmax(C(p))) if not. One consequence of this definition and requirement (1) on Q_Partition is that the maximal partition of a subset p (that is, the partition V of p for which Qmax(V) is maximal) is either p or the union of the maximal partitions of each element of C(p) (ties may be broken by taking the subset p instead the children).

In various embodiments, the autogrouping method uses a hierarchical clustering process on S to compute F (i.e., to construct the forest F) and if Q_Partition is a scoring function on the roots R of F, we can find the Q_Max maximal partition of S subordinate to F. Joining a scoring function Q( ) with hierarchical clustering may provide a principled method for choosing among the partitions for the "Q-maximal partition."

The partition generation module 2104 may begin with the original space S and may form a forest F described above. In some embodiments, the generation module 2104 takes a partition P and returns a new partition P' which is coarser than P. Note that Clumper({S})={S}. Any partition P such that generation module 2104 Clumper(P)=P is called dumper-terminal, and repeated applications must eventually reach a dumper-terminal partition. The sequence Singletons(S), Clumper(Singletons(S)), Clumper(Clumper (Singletons(S))), etc., may terminate in a finite number of steps, and the union of all these partitions forms an atomic forest F whose roots are the elements in a C-terminal partition R, which are the roots of F.

One example process utilizing the scoring functions and generating partitions is as follows in the following pseudo-code:

```
P = INITIAL(S) // some initial partition - often Singletons( ), but it can
                 be any partition
F = Tree(P) // node for every subset, remember connections, and have
                 max slot
             // to hold partition of the node's set which has maximal
                 score
for (x in S) { {x}.max = {x} }
BEGIN
    P' = clumper(P)
    if P==P'
        then
            quit
        else
            UPDATE_Qmax(P',P)
END
UPDATE_Qmax(P',P)
    for (p in P') {
        if (!(p in P)) {
            Subset pSubset = AddSubset(p,F);
            if (Q_Subset(p) >= QP(C(p)))
                pSubset.maxPartition = p
                pSubset.Qmax = Q(p)
            else
                pSubset.Qmax = QP(C(p))
                pSubset.maxPartition = MAX_UNION(C(p))
        }
    }
MAX_UNION({Ni})
    return the union of Ni.max
```

When this process terminates, the elements of the roots R of F may contain their maximal partitions, the union of which is the best partition in F of S.

The partition selection module 2112 may find a partition subordinate to the forest F that maximizes at least one scoring function. For example, the partition selection module 2112 may select a partition subordinate to the forest F that maximizes the scoring function QP.

In various embodiments, each subset of a partition (as discussed herein) may be associated with its own scores. For example, each subset of a partition may be associated with a different Q_Max score. The partition selection module 2112 may select subsets of unique elements from any number of different partitions of the forest F using the Q_Max score to generate and select a partition.

For example, looking to FIG. 19*d*, the partition selection module 2112 may select subset {A, B, C} from one partition and subsets {D,E}, {F}, AND {G} from another partition based on a scoring function. The selected subsets may then form (e.g., generate) a new selected partition P1 (e.g., a partition including subsets {A, B, C}, {D,E}, {F}, AND {G}). The selected partition P1 may be termed an output partition. In this example, the partition selection module 2112 may select the subset {A, B, C} from the first partition utilizing the Q_Max score. In a further example, each subset of all partitions that include any of elements A, B, or C, may be associated with a separate Q_Max score. The maximum Q_Max score of all the sets that include any of the elements of A, B, or C is the subset {A, B, C}. As a result, the partition selection module 2112 selects that subset {A, B, C} in this example.

Similarly, each subset of all partitions that include any of elements D, E, F, or G, may be associated with a separate Q_Max score. The maximum Q_Max scores of all the sets that include any of the elements of D, E, F, or G are the subsets {D,E}, {F}, and {G} (i.e., the Q_Max scores associated with subsets {D, E, F, G}, {D, E, F}, and {G} are not the maximum when compared to the Q_Max scores of subsets {D,E}, {F}, and {G}). As a result, the partition selection module 2112 selects subsets {D,E}, {F}, and {G} in this example.

One example of a scoring function mentioned herein includes a modularity score for weighted graphs on a node set S. In some embodiments, the modularity score of a subset of a graph proportion of edges within a subset, the e's, and the a's which are the proportion of edges which cross the boundaries of the subset. The final score may be: e−a^2. In various embodiments, the partition selection module 2112 selects and/or generates a partition by maximizing this score. The modularity partition scorer, QP, may be the sum of the modularity scores on the subsets within that partition.

Another example of a scoring function is a variant of entropy for a set S which has an associated classification: that is, a function cls: S→{1, 2, . . . , k} (i.e. you have a set and everything has some finite label.) For s subset of S, we define $p\_i(s)=|\{x \text{ in } s: cls(x)==i\}|/|s|$, provided $|s|!=0$. Then $Q(s)=sum\_\{classes\ i\}(p\_i(s)*log(p\_i(s)))$. The extension of the entropy scorer Q to a partition scorer, QP is given by the extension property (3) where $A(p, q)=|p|/|q|$. In other words, for a partition P, $QP(P)=sum\_\{p \text{ in } P\} (Q(p)*|p|/|U(P)|)$. Normally one wants to minimize the entropy and the subset scorer here is the negative of the traditional entropy score by maximizing the scoring function.

The data control module 2114 is configured to provide the selected and/or generated partition from the partition selection module 2112. In various embodiments, the data control module 2114 generates a report indicating the selected and/or generated partition from the partition selection module 2112. The report may include, for example, data sets, partitions, subsets, elements, data set identifiers, partition identifiers, subset identifiers, element identifiers, and/or the like. In some embodiments, the report may include a graph (e.g., see FIG. 19) with an indication of selected nodes whose member(s) include data of the selected and/or generated partition from the partition selection module 2112.

Figure 22:
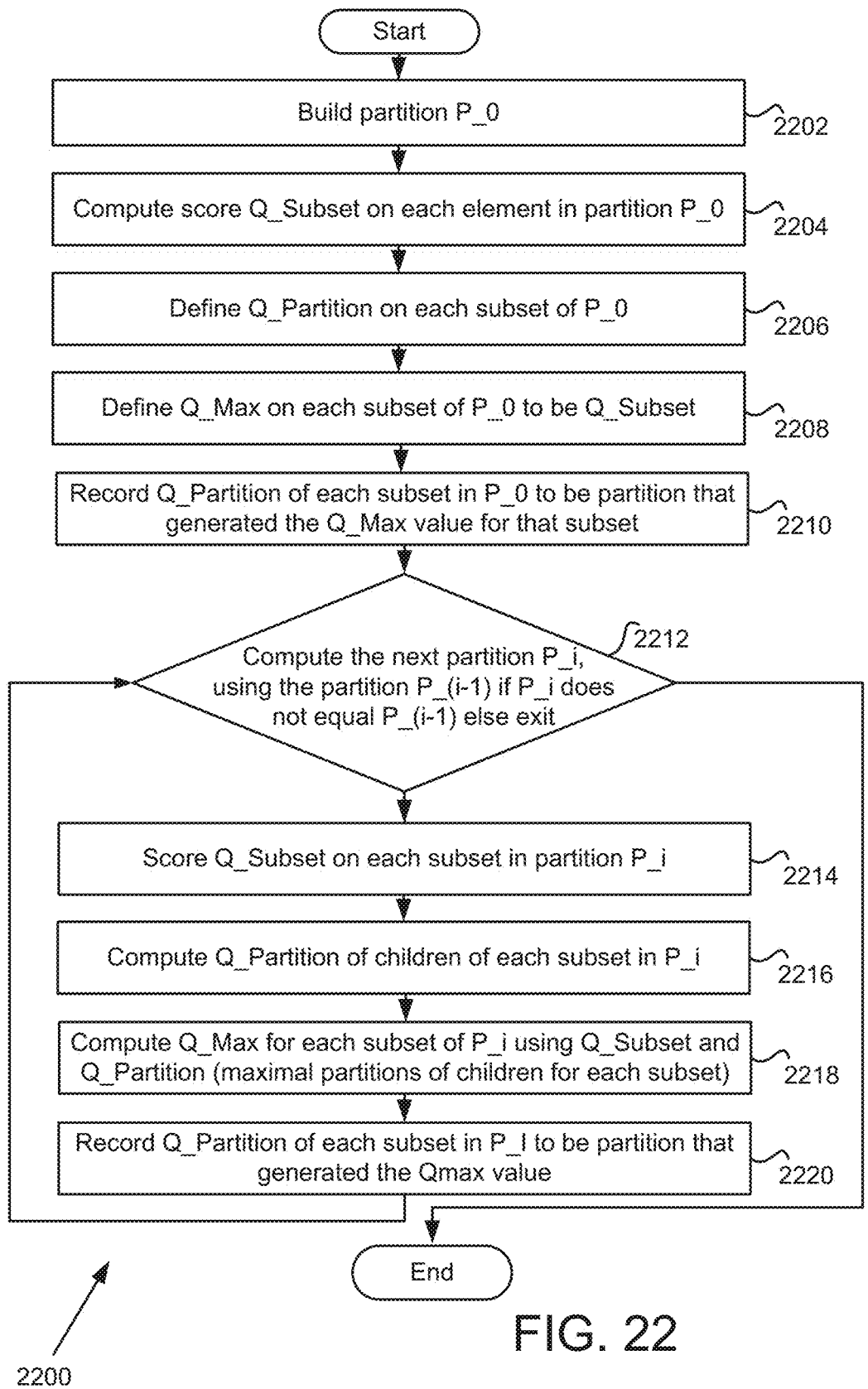
FIG. 22 is an example flowchart for autogrouping in some embodiments.

FIG. 22 is an example flowchart for autogrouping in some embodiments. In this example, the autogroup module 2002 receives a set S={A, B, C, D, E, F, G} and performs autogrouping to identify a selected partition of a forest based on S. Elements of set S may be, for example, nodes of a graph wherein the graph may be visualized (e.g., a visualization as discussed herein) or not visualized. The graph may be a topological data analysis graph of nodes and edges as described herein. In some embodiments, the graph may be any network graph that includes nodes, neighborhoods, groupings, communities, and/or data points.

Non-limiting examples describing at least some of the steps in FIG. 22 will be described using the graph depicted in FIG. 23. The embodiment of the Q_Partition in this example is simply the sum over the subsets of the partition P of the Q_Subset scores on each subset. For example, if P={{A, B, C}, {D}, {E, F}, {G}}, then Q_Partition(P)= Q_Subset({A, B, C})+Q_Subset({D})+Q_Subset({E, F})+ Q_Subset({G}).

In step 2202, the data structure module 2102 receives the set S and the partition generation module 2104 generates an initial partition which are the singletons of the set S={A, B, C, D, E, F, G}, namely, P_0={{A}, {B}, {C}, {D}, {E}, {F}, {G}}. This is illustrated in FIG. 23 as the bottom row (2302) of the depicted forest.

In step 2204, the Q_subset score module 2106 computes the Q_Subset score on each subset of the partition P_0. In this example, the Q_subset score module 2106 scores each singleton subset with a value of 0.5. This score is shown in FIG. 23 for each subset of partition 2302 as Q_Sub=0.5. The scoring function in this example, may be a modularity scoring function discussed herein.

In step 2206, the Q_partition score module 2110 computes the maximal partition of each subset a of P_0 from the children of the subset a in the constructed forest. Since the subsets a in P_0 have no children in the forest, the maximal partition of the children of the subset a is itself. Namely, for each subset a in P_0, MaximalPartitionChildren(a)=a.

In this example, the Q_partition score module 2110 computes the maximal partition of each subset as itself. This is shown in FIG. 23 for each subset of partition 2302 as MaxP={A} for subset {A}, MaxP={C} for subset {C}, MaxP={D} for subset {D}, MaxP={E} for subset {E}, MaxP={F} for subset {F}, and MaxP={G} for subset {G}.

In step 2208, the Q_max score module 2108 computes Q_Max on each subset of P_0. Recall that since the subsets in P_0 do not have any children, for each subset a in P_0, $$Q\_Max(a) = \max(Q\_Subset(a), Q\_Partition(MaximalPartitionChildren(a)))$$
$$= \max(Q\_Subset(a), Q\_Partition(a))$$
$$= \max(Q\_Subset(a), Q\_Subset(a))$$
$$= Q\_Subset(a)$$
$$= 0.5$$

In this example, the Q_max score module 2108 scores each subset with a value of 0.5. This Q_Max score is shown in FIG. 23 for each subset of partition 2302 as Q_Max=0.5.

In step 2210, we optionally record the maximal partition of each subset a in P_0 to be partition of the subset a that generated the Q_Max for that subset. Thus we record the MaximalPartition(a)=a in this initial partition.

Figure 23:
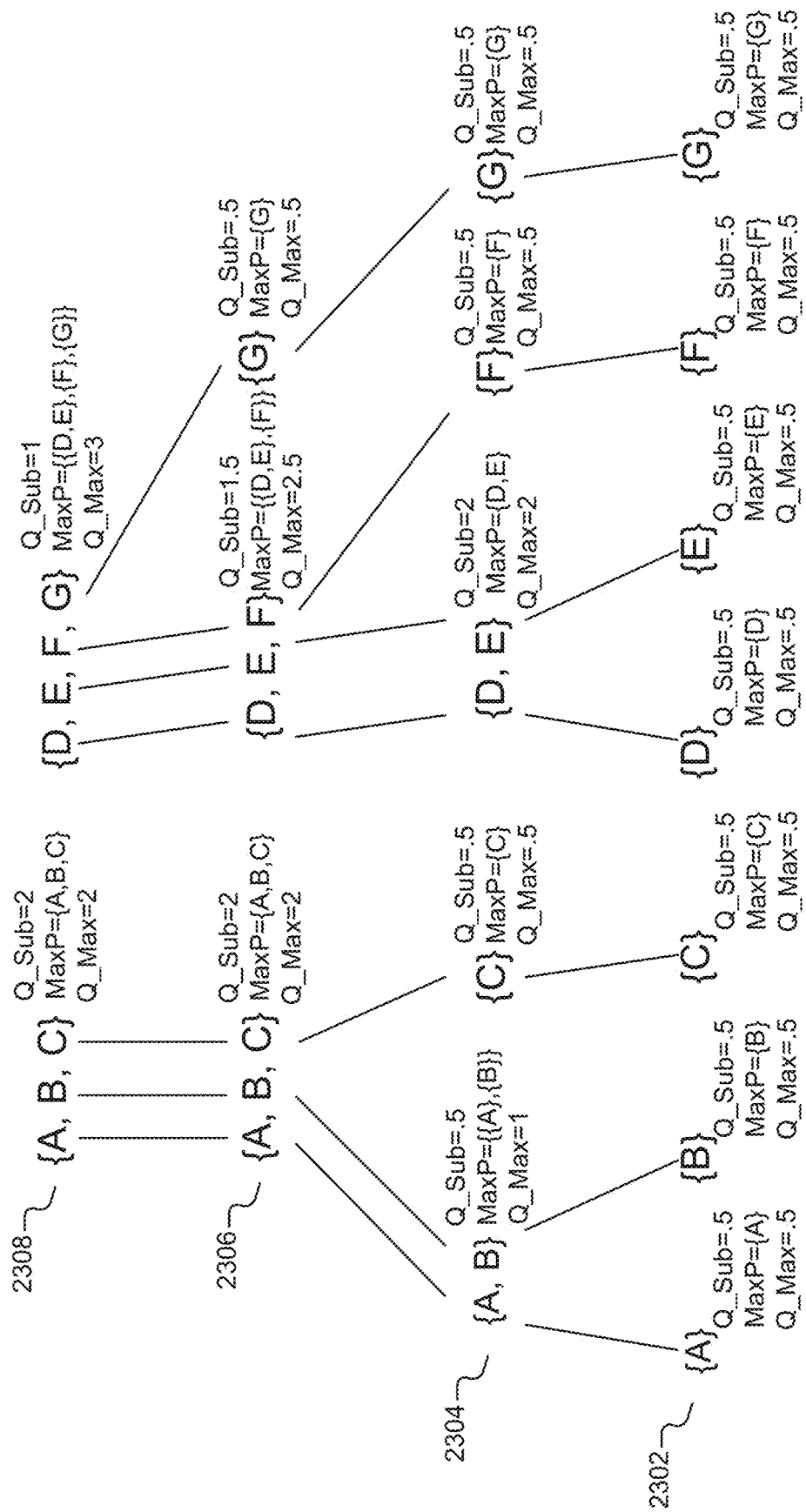
FIG. 23 depicts an example of determining a partition based on scoring in some embodiments.

In step 2212, the data structure module 2102 computes the next partition P_1 (the row labeled 2304 in FIG. 23). Namely, in this example, the data structure module 2102 groups subsets {A} and {B} into the subset {A, B} and subsets {D} and {E} into subset {D, E}. The data structure module 2102 preserved the subsets {C}, {F}, and {G} from the partition P_0 in the partition P_1.

It will be appreciated that the next partition P_1 may group subsets of previous partition(s) (e.g., partition 2304) in any number of ways. For example, the data structure module 2102 may group a predetermined number of subsets together at random and/or may group two or more subsets together based on the elements (e.g., based on the underlying data that the elements represent). In one example, the data structure module 2102 may group elements together using a distance metric and/or any other functions to define relationships in the underlying data and/or within a similarity space (e.g., reference space).

In various embodiments, the data structure module 2102 may determine whether the system ends and/or whether a new partition is to be computed. It will be appreciated that the data structure module 2102 may perform the determination based on any number of ways. In some embodiments, the data structure module 2102 determines if the next generated partition is equal to the previous partition. If the two partitions are equal (e.g., have the same subsets), the method may terminate, otherwise the method may continue to step 2214.

In some embodiments, the data structure module 2102 terminates the method after a predetermined number of partitions are generated, if a predetermined number of roots are found, and/or the like. In various embodiments, the data structure module 2102 may terminate the method if a predetermined number of subsets are present in a computed partition. In another example, the data structure module 2102 may terminate the method after a predetermined period of time, a predetermined period of memory usage, or based on any threshold (e.g., the threshold being calculated based on the amount of data received).

In step 2214, the Q_subset score module 2106 computes the Q_Subset score on each subset of the partition P_1. In this example, the Q_subset score module 2106 computes Q_Subset({A, B})=0.5 and Q_Subset({D,E})=2. In one example, the Q_subset score module 2106 calculates a modularity score for elements A and B for Subset {A,B} and a modularity score for elements D and E for Subset {D,E}. As discussed herein, the modularity score may be based on the edges of nodes A and B for Q_Subset({A, B}) modularity score and based on the edges of nodes D and E for Q_Subset({D, E}) modularity score.

As was discussed in the paragraph above describing step 2204, Q_Subset of each singleton subset is 0.5 (e.g., the previous Q_Subset score for singleton subsets in step 2304 remains unchanged from step 2302). These scores are associated with each subset and are visualized in the FIG. 23 as Q_Sub in 2304.

In step 2216, the Q_partition score module 2110 then computes the maximal partition at the children of each subset of P_1. The maximal partition of the children of the subsets {C}, {F}, and {G} are again the original singleton subset. The maximal partition of the children {A, B} is the set including the maximal partitions of the children of {A, B}, namely {{A}, {B}} as depicted in partition 2304 in FIG. 23. Similarly the maximal partition of the children of {D, E} is the set {{D}, {E}} as also depicted in partition 2304 in FIG. 23.

In step 2218, the Q_max score module 2108 computes the Q_Max on each subset of P_1. Recall Q_Max(a)=max(Q_Subset(a), Q_Partition(MaximalPartitionChildren(a))). For the subset {A, B}:

$$Q\_Max(\{A, B\}) = \max(Q\_Subset(\{A, B\}), Q\_Partition(\{\{A\}, \{B\}\}))$$
$$= \max(.5, Q\_Subset(\{A\}) + Q\_Subset(\{B\}))$$
$$= \max(0.5, 1)$$
$$= 1$$

For the subset {D, E}:

$$Q\_Max(\{D, E\}) = \max(Q\_Subset(\{D, E\}), Q\_Partition(\{\{D\}, \{E\}\}))$$
$$= \max(2, Q\_Subset(\{D\}) + Q\_Subset(\{E\}))$$
$$= \max(2, 1)$$
$$= 2.$$

As displayed in partition 2304 of FIG. 23, Q_Max of {A,B} is 1 and Q_Max of {D,E} is 2. The Q_Max of singletons {C}, {F}, and {G} in partition 2304 remain consistent with the respective subsets in partition 2302. Namely, the Q_Max of each of {C}, {F}, and {G} is 0.5.

In step 2220, we optionally record the maximal partition of each subset a in P_1 that resulted in the Q_Max score. As seen above and in FIG. 23, MaxPartition({A, B})={{A}, {B}} and MaxPartition({D, E})={D,E}.

Step 2212 is repeated. The data structure module 2102 computes the next partition P_2, depicted in FIG. 23 as row (partition) 2306. In various embodiments, the data structure module 2102 may determine whether the system ends and/or whether a new partition is to be computed. It will be appreciated that the data structure module 2102 may perform the determination based on any number of ways.

In step 2214, the Q_subset score module 2106 computes the Q_Subset score on each subset of the partition P_2. In this example, the Q_subset score module 2106 computes Q_Subset({A, B, C})=2 and Q_Subset({D, E, F})=1.5. Again, Q_Subset({G})=0.5. These scores are recorded with each subset and are visualized in the FIG. 23 in partition 2306.

In step 2216, the Q_partition score module 2110 computes the maximal partition at the children of each subset of P_2. The maximal partition of the children{G} is the subset {G}. The maximal partition of the children {A, B, C} is the set consisting of the maximal partitions of the children of {A, B, C}, namely {MaxPartition({A,B}), MaxPartition({C})={{A}, {B}, {C}}. Similarly the maximal partition of the children of {D, E, F} is the set {MaxPartition({D, E}), MaxPartition({F})}={{D, E}, {F}}.

This is shown in FIG. 23 for each subset of partition 2306 as MaxP={A, B, C} for subset {A, B, C}, MaxP={{D,E}, {F}} for subset {D, E, F,}, and MaxP{G} for subset {G}.

In step 2218, the Q_max score module 2108 computes the Q_Max on each subset of P_2. Recall Q_Max(a)=max(Q_Subset(a), Q_Partition(MaximalPartitionChildren(a))). For the subset {A, B, C}:

$$Q\_Max(\{A, B, C\}) = \max(Q\_Subset(\{A, B, C\}),$$
$$Q\_Partition(\{\{A\}, \{B\}, \{C\}\}))$$
$$= \max\binom{2, Q\_Subset(\{A\}) + }{Q\_Subset(\{B\}) + Q\_Subset(\{C\})}$$
$$= \max(2, 1.5)$$
$$= 2$$

For the subset {D, E, F}:

$$Q\_Max(\{D, E, F\}) = \max(Q\_Subset(\{D, E, F\}),$$
$$Q\_Partition(\{\{D, E\}, \{F\}\}))$$
$$= \max\binom{1.5, Q\_Subset(\{D, E\}) + }{Q\_Subset(\{F\})}$$
$$= \max(1.5, 2.5)$$
$$= 2.5$$

As displayed in partition 2306 of FIG. 23, Q_Max of {A, B, C} is 2 and Q_Max of {D, E, F} is 2.5 The Q_Max of singleton{G} in partition 2306 remains consistent with the respective subset in partition 2304. Namely, the Q_Max {G} is 0.5.

In step 2220, we optionally record the maximal partition of each subset a in P_2 that resulted in the Q_Max score. As seen above, MaxPartition({A, B, C})={{A, B, C}} and MaxPartition({D, E, F})={{D, E}, {F}}.

Step 2212 is repeated. The data structure module 2102 computes the next partition P_3, depicted in FIG. 23 as row (partition) 2308. The data structure module 2102 may determine whether the system ends and/or whether a new partition is to be computed.

In step 2214, the Q_subset score module 2106 computes the Q_Subset score on each subset of the partition P_3. In this example, the Q_subset score module 2106 computes Q_Subset({A, B, C})=2 and Q_Subset({D, E, F, G})=1. These scores are recorded with each subset and are visualized in FIG. 23 in partition 2308.

In step 2216, the Q_partition score module 2110 computes the maximal partition at the children of each subset of P_3. The maximal partition of the children {A, B, C} is the set consisting of the maximal partitions of the children of {A, B, C}, namely {MaxPartition({A, B, C})}={{A, B, C}.

Similarly the maximal partition of the children of {D, E, F, G} is the set {MaxPartition({D, E, F}), MaxPartition({G})}={{D, E}, {F}, {G}}.

This is shown in FIG. 23 for each subset of partition 2308 as MaxP={A, B, C} for subset {A, B, C} and MaxP={{D, E}, {F}, {G}} for subset {D, E, F, G}.

In step 2218, the Q_max score module 2108 computes the Q_Max on each subset of P_3. Recall Q_Max(a)=max (Q_Subset(a), Q_Partition(MaximalPartitionChildren(a)). For the subset {A, B, C}:

$$\begin{aligned}Q\_Max(\{A, B, C\}) &= \max(Q\_Subset(\{A, B, C\}), \\ &\quad Q\_Partition(\{A, B, C\})) \\ &= \max(2, Q\_Subset(\{A, B, C\})) \\ &= 2\end{aligned}$$

For the subset {D, E, F, G}:

$$\begin{aligned}Q\_Max(\{D, E, F, G\}) &= \max(Q\_Subset(\{D, E, F, G\}), \\ &\quad Q\_Partition(\{\{D, E\}, \{F\}, \{G\}\})) \\ &= \max\begin{pmatrix}1, Q\_Subset(\{D, E\}) + \\ Q\_Subset(\{F\}) + \\ Q\_Subset(\{G\})\end{pmatrix} \\ &= \max(1, 3) \\ &= 3\end{aligned}$$

As displayed in partition 2308 of FIG. 23, Q_Max of {A, B, C} is 2 and Q_Max of {D, E, F, G} is 3.

In step 2220, we optionally record the maximal partition of each subset a in P_3 that resulted in the Q_Max score. As seen above, MaxPartition({A, B, C})={{A, B, C}} and MaxPartition({D, E, F, G})={{D, E}, {F}, {G}}.

Although not depicted in method 2200, the method may continue. For example, the partition selection module 2112 may identify and/or generate a preferred partition from that maximizes one or more scoring functions. In this example, the preferred partition is the MaxPartition. As discussed immediately above, the maximal partition of each subset in P_3 is MaxPartition({A, B, C})={{A, B, C}} and MaxPartition({D, E, F, G})={{D, E}, {F}, {G}}. The partition selection module 2112 may identify and/or generate the autogrouped partition {{A, B, C}, {{D, E}, {F}, {G}}.

The data control module 2114 may provide the identified and/or generated autogrouped partition in a report and/or identify the autogrouped partition in data or a graph.

Figure 24:
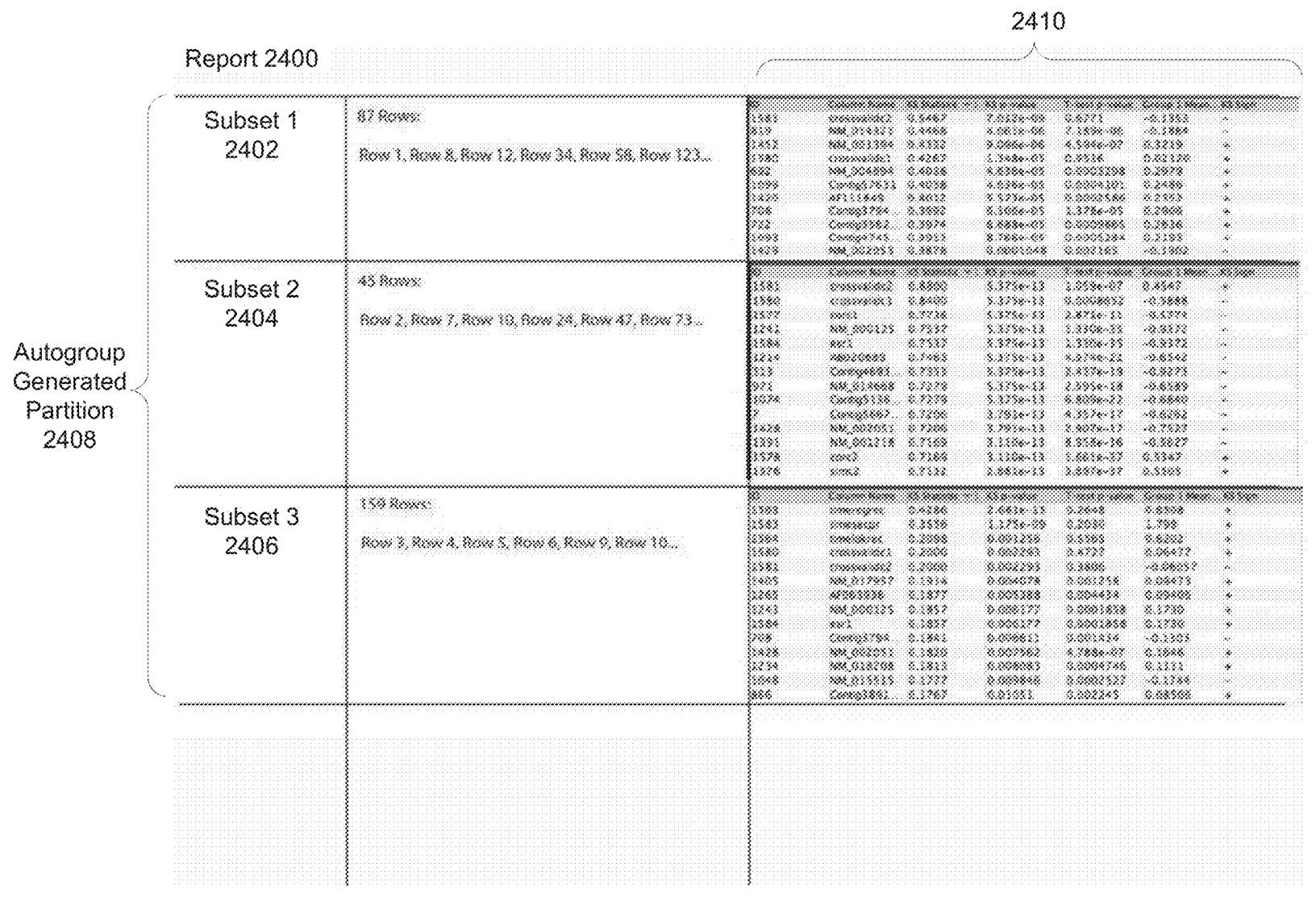

FIG. 24 is an example report 2400 of an autogrouped graph of data points that depicts the grouped data in some embodiments. Subsets 2402, 2404, and 2406 are subsets of data points that, together, make a partition (i.e., the autogrouped generated partition 2408). In various embodiments, data may be received and nodes generated utilizing embodiments described herein (e.g., see description regarding FIG. 4 or 8). The nodes that represent at least some of the received data may be autogrouped into a number of subsets 2402, 2404, and 2406 of an autogroup generated partition 2408. The report 2400 may depict the subets including the rows of the underlying data associated and/or within each subset as well as all or some of the underlying data 2410 for that subset.

For example, the autogroup module 2002 may generate a report that shows each subset of datapoints for an autogroup generated partition. The rows, columns, or other data identifiers may be associated with each subset. Further, all or some of the data associated with each subset may be displayed (e.g., including any independent variables such as data identifiers, for example, patient identifiers).

The report may allow groups of nodes (e.g., nodes that are part of a subset of the output partition) to be identified. The identified groups of nodes may be identified in a visualization by coloring the nodes in a group a similar color, shape of nodes, a graphical element associated with nodes in a group (e.g., a box around nodes in a group), and/or in any number of ways. In some embodiments, the identified groups of nodes allow a user to create queries, analyze, and/or view data associated with nodes in a group for insights.

In some embodiments, autogrouping may be utilized on a weighted graph. In this example, the set that will be autogrouping is the set of nodes of a weighted graph G. The idea is to automatically partition the graph into groups of nodes that are strongly-connected in the graph. An unweighted graph may be transformed into a weighted graph if there is a function $f$ on the nodes of the graph. The weight for an edge (a, b) between two nodes a and b in the graph G may be defined to be the difference between the function values: $wt(a, b)=|f(a)-f(b)|$. In another embodiment, this graph may be a visualization generated from a data set and the function on the nodes may be given by a color scheme on the nodes.

In one example, the input graph G may be generated from connecting points to their nearest neighbors, where the metric space is a set of 2200 points from 5 Gaussian samples in the Euclidean plane. The graph may be colored by the Gaussian density. The graph is made into a weighted graph by weighting each edge in G by the difference in the Gaussian density function at the edge's endpoints.

Figure 25:
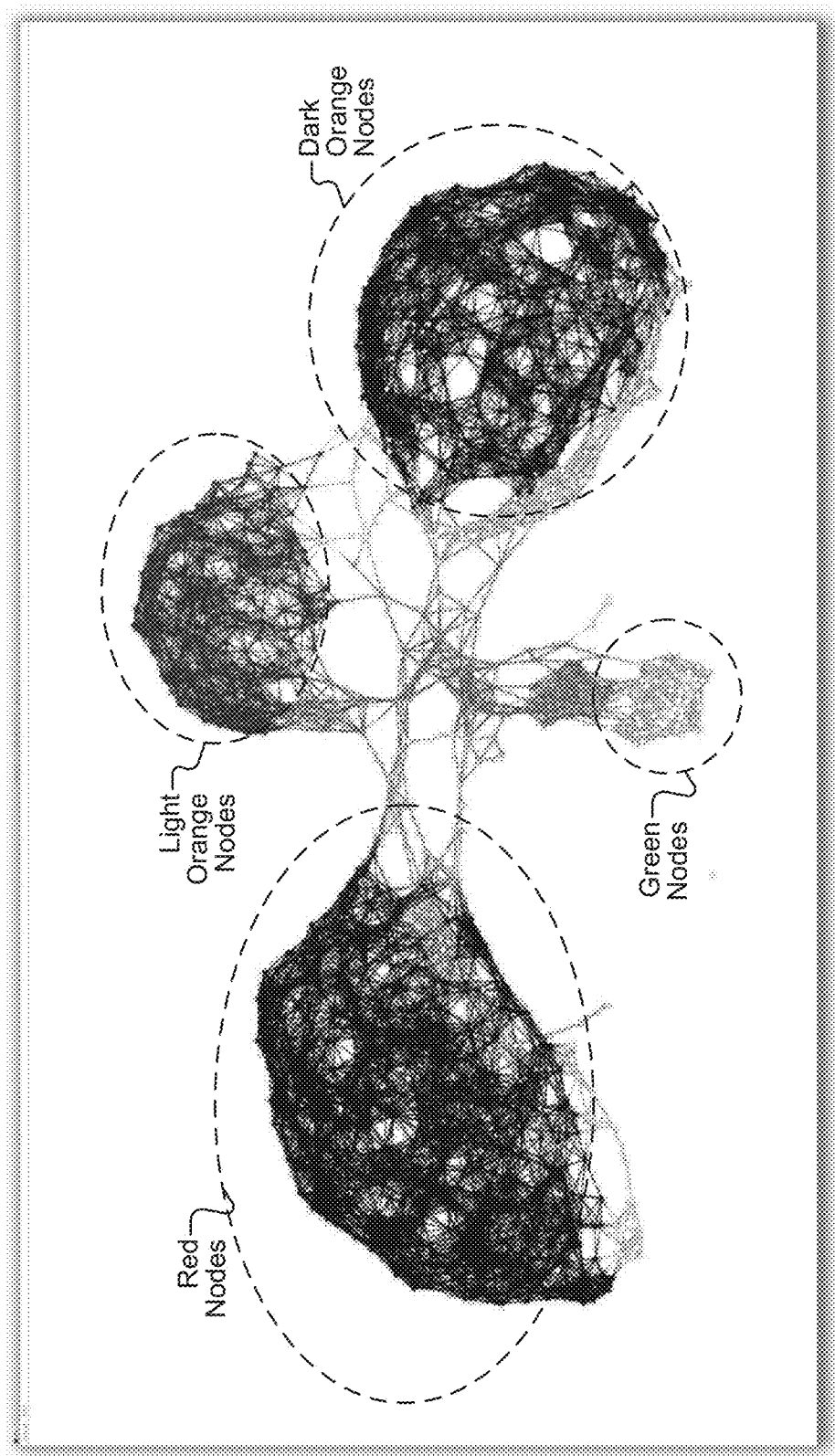
FIG. 25 is an example visualization generated based on an input graph, each edge being weighted by a difference of a density function at the edge endpoints.

The method is applied uses the scoring mechanisms described herein regarding weighted graphs and the modularity scorer applied to the weighted graph G. The resulting maximal partition may be "color coded" (utilizing greyscale) in FIG. 25.

Figure 26:
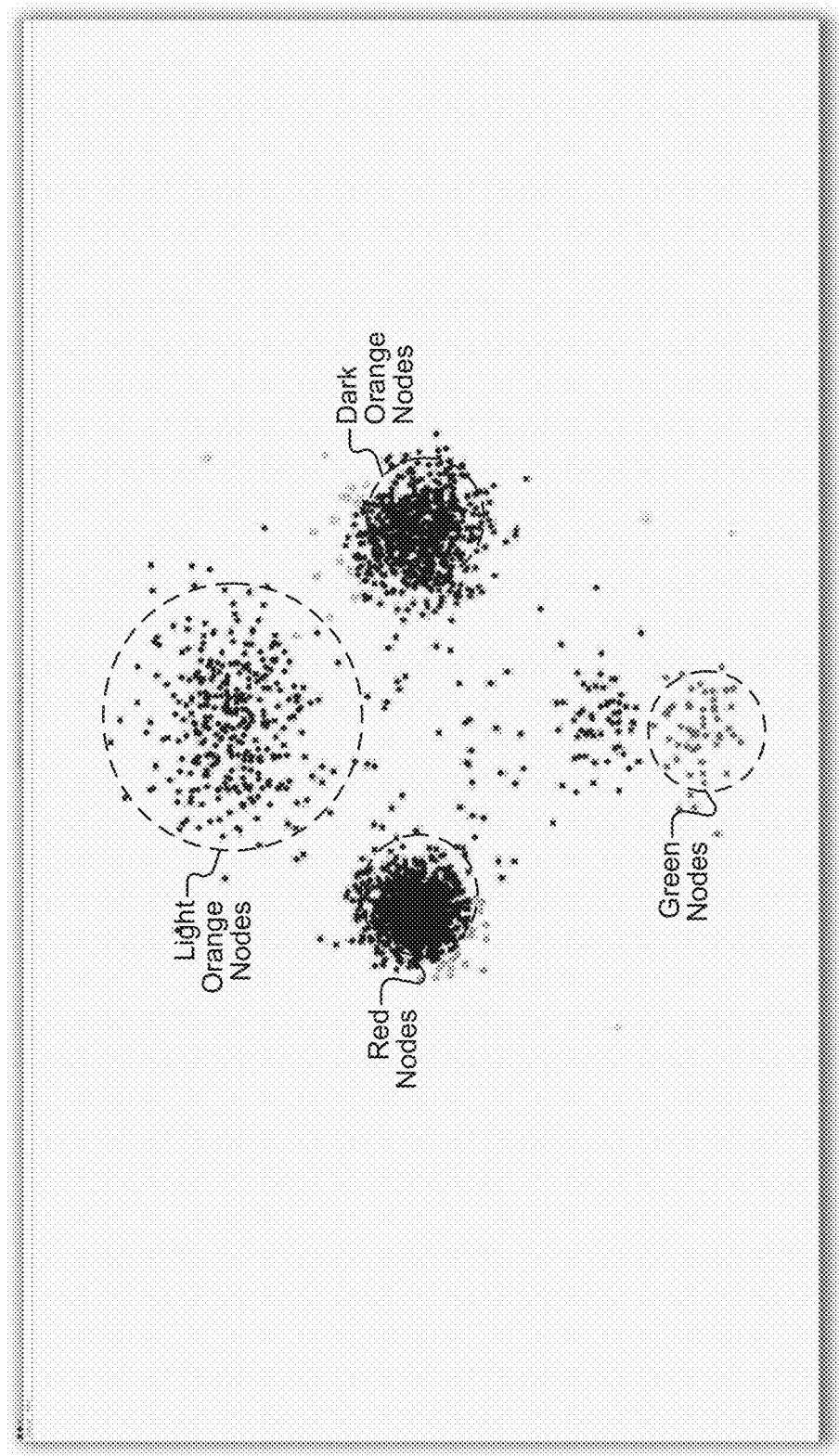
FIG. 26 is another example visualization generated using autogrouped partitions of a graph into regions that are strongly connected and have similar function values.

To elucidate the groups, we look at the corresponding points and assignments in a scatter plot of the points in the Euclidean plane in FIG. 26. As the graph G comes from the geometry in this data set, subtle geometric features are preserved in this decomposition. In other words, in this example, autogrouping partitioned the graph into regions of the graph that are strongly connected and have similar function (specifically density) values. This is helpful as the data points within each group are now very similar to each other drawing statistical conclusions from each subset is much more likely to be statistically significant.

In one application of this embodiment, the original data may be a data set that is input into the graph construction (e.g., as discussed regarding FIG. 8), which produces a graph (the graph may be in memory or a visualization). The visualization may be colored by the average value of a function of interest on the data points as discussed herein. One such coloring might be the outcome of interest for the data set such as survival of patients, power output in an electric generator, etc. The coloring is used to convert the graph (e.g., in memory or visualization) into a weighted graph that may be then autogrouped using one or more of the autogrouping embodiments described herein. Various autogrouping algorithm partitions the graph into subsets that are highly connected and have similar color values.

The groups may be used to create a new color scheme for the graph for use in a visualization. They may also be used for automatic statistical analysis and report generation. Moreover, this process may be used to start with the dataset, generate a graph (but not necessarily generate a visualization) (e.g., generate all or part of the graph in memory), and then report to the user the subsets of the final autogrouped maximal partition together with statistical calculations on those subsets.

As discussed herein, recall that once a filter is computed, data points may be mapped to a reference space and an open cover is generated in that reference space (see discussion regarding FIG. 8). The elements in the open cover may be iterated over, together with clustering, to generate the nodes in the resulting visualization. In one example described herein, the open cover may take intervals in the reference space (or cross-products of intervals in the case of more than one filter). The following embodiment is a data-driven alternative to generating the open cover in the reference space.

The set S in this embodiment are the projections of the original data points into the reference space (e.g., a function such as a gausian density function is applied on the received data points to project to the reference space). The autogroup module 2002 may operate on a weighted graph built from this projection of the data into the reference space. For example, for a fixed positive integer k, construct a graph G on the set S by connecting each point a in S to every point b in S if b is one of a's k-nearest neighbors and a is one of b's k-nearest neighbors (i.e. they are symmetric k-nearest neighbors of each other). In some testing, k=20 produces good results. The edges of the graph may be weighted by the distance between the edge's endpoints in the embedded reference space distance. This autogrouping embodiment may utilize a hierarchical single-linkage clusterer that uses distance between points in the reference space. The scorer modules (e.g., modules 2106, 2108, and/or 2110 in FIG. 21) may utilize a modularity score built off of the weighted neighborhood graph G.

The result of this embodiment may be a partition P of the projection of the data points in the reference space. Now for a fixed positive integer j, we can expand each subset a of P by adding all the j-nearest neighbors in the reference space of the elements in the subset a. The new, expanded subsets may no longer be a partition as some points may now exist in multiple subsets but this new collection of subsets forms the open cover of the reference space (see discussion regarding FIG. 8) in the graph construction.

In various embodiments, autogrouping may be used for clustering. For example, in the embodiments described with regard to FIG. 8, after a cover is generated either in the reference space or in the original space, data is clustered on each of the subsets in the open cover to identify nodes (e.g., see steps 808-812). Autogrouping clustering may be an adaptive alternative to single linkage clustering with a fixed distance cut-off.

For example, the set S is a set data together with a metric which defines a distance between any two points in the set S. In the discussion regarding FIG. 8, these points may have come from the open cover in the reference space. In the current example, the partition generation module 2104 (see FIG. 21) and one or more of the score modules (e.g., the Q_Subset score module 2106, the Q_Max score module 2108, and/or the Q_Partition score module 2110) operate on a weighted neighborhood graph built from the data. For a fixed positive integer k, a graph G may be constructed on the set S by connecting each point "a" in S to every point "b" in S if "b" is one of "a's" k-nearest neighbors and "a" is one of "b's" k-nearest neighbors under the given metric (i.e. they are symmetric k-nearest neighbors of each other). In some instances, k=20 produces good results. The edges of this graph may be weighted by the distance between the edge's endpoints. The partition generation module 2104 for this autogrouping example is a hierarchical single-linkage clusterer that uses the distance between points determined by the given metric. The one or more of the score modules (e.g., the Q_Subset score module 2106, the Q_Max score module 2108, and/or the Q_Partition score module 2110) uses the modularity score built off of the weighted neighborhood graph G. The resulting clustering would likely have clusters formed at a variety of distance cut-offs instead of a single fixed distance cut-off for the set S.

In another example, the elements of the set S might have additional information such as an associated classification, that is, for example, a function cls: $S \rightarrow \{1, 2, \ldots, k\}$ (i.e. there is a set and everything has some finite label.) The one or more of the score modules (e.g., the Q_Subset score module 2106, the Q_Max score module 2108, and/or the Q_Partition score module 2110) may score entropy (e.g., one or more of the score modules may be an entropy scorer).

One example of an entropy scorer $Q(a)=\text{sum}\_\{\text{classes } i\}$ $(p\_i(a)*\log(p\_i(a)))$ where $p\_i(a)=|\{x \text{ in } a: cls(x)==i\}|/|a|$, provided $|a|!=0$. The extension of the entropy scorer Q to a partition scorer, QP is given by the extension property (3) where $A(p, q)=|p|/|q|$. In other words, for a partition P, $QP(P)=\text{sum}\_\{p \text{ in } P\} (Q(p)*|p|/|U(P)|)$. The combination of the partition generation module 2104 and one or more of the score modules (e.g., the Q_Subset score module 2106, the Q_Max score module 2108, and/or the Q_Partition score module 2110) may produce the maximal partition (i.e. clustering) of the elements of the set S that emphasizes clusters that are very close in distance and have the lowest entropy in class type in the subsets of the partition. In other words, this example embodiment may locate clusters that have the largest proportion of each single class type possible under the constraint of the distance metric.

In some embodiments, autogrouping may be used for open cover generation without a reference space. For example, in the embodiments described with regard to FIG. 8, a filter may be generated, points may be mapped to the reference space, and an open cover may be generated in that reference space (e.g., see steps 802-808). The elements in the open cover may be iterated over, together with clustering, to identify nodes. In some embodiments, the open cover may be constructed in the reference space. Various embodiments include a data-driven alternative to generating the open cover of the original data without the need to have a filter or a reference space.

In one example, the set S is the original data together with a metric which defines a distance between any two points in the set S. Both the partition generation module 2104 and the one or more of the score modules (e.g., the Q_Subset score module 2106, the Q_Max score module 2108, and/or the Q_Partition score module 2110) may operate on a weighted neighborhood graph built from the data. Specifically, for a fixed positive integer k, a graph G on the set S is constructed by connecting each point "a" in S to every point "b" in S if "b" is one of "a's" k-nearest neighbors and "a" is one of "b's" k-nearest neighbors under the given metric (i.e. they are symmetric k-nearest neighbors of each other).). In some instances, k=20 produces good results. The edges of this graph may be weighted by the distance between the edge's endpoints. The partition generation module 2104 for this embodiment is a hierarchical single-linkage clusterer that uses the distance between points determined by the given metric. One or more of the score modules (e.g., the Q_Subset score module 2106, the Q_Max score module 2108, and/or the Q_Partition score module 2110) may use the modularity score built off of the weighted neighborhood graph G.

The result in this example is a partition P of the data points in the original space. For a fixed positive integer "j", we can expand each subset "a" of P by adding all the j-nearest neighbors of the elements in the subset "a". The new, expanded subsets may no longer be a partition as some points may now exist in multiple subsets but this new collection of subsets may form the open cover of the space for step 808 as described in FIG. 8.

In various embodiments, information (e.g., insights) from topological data analysis are used to create and improve various predictive modeling procedures.

Figure 27:
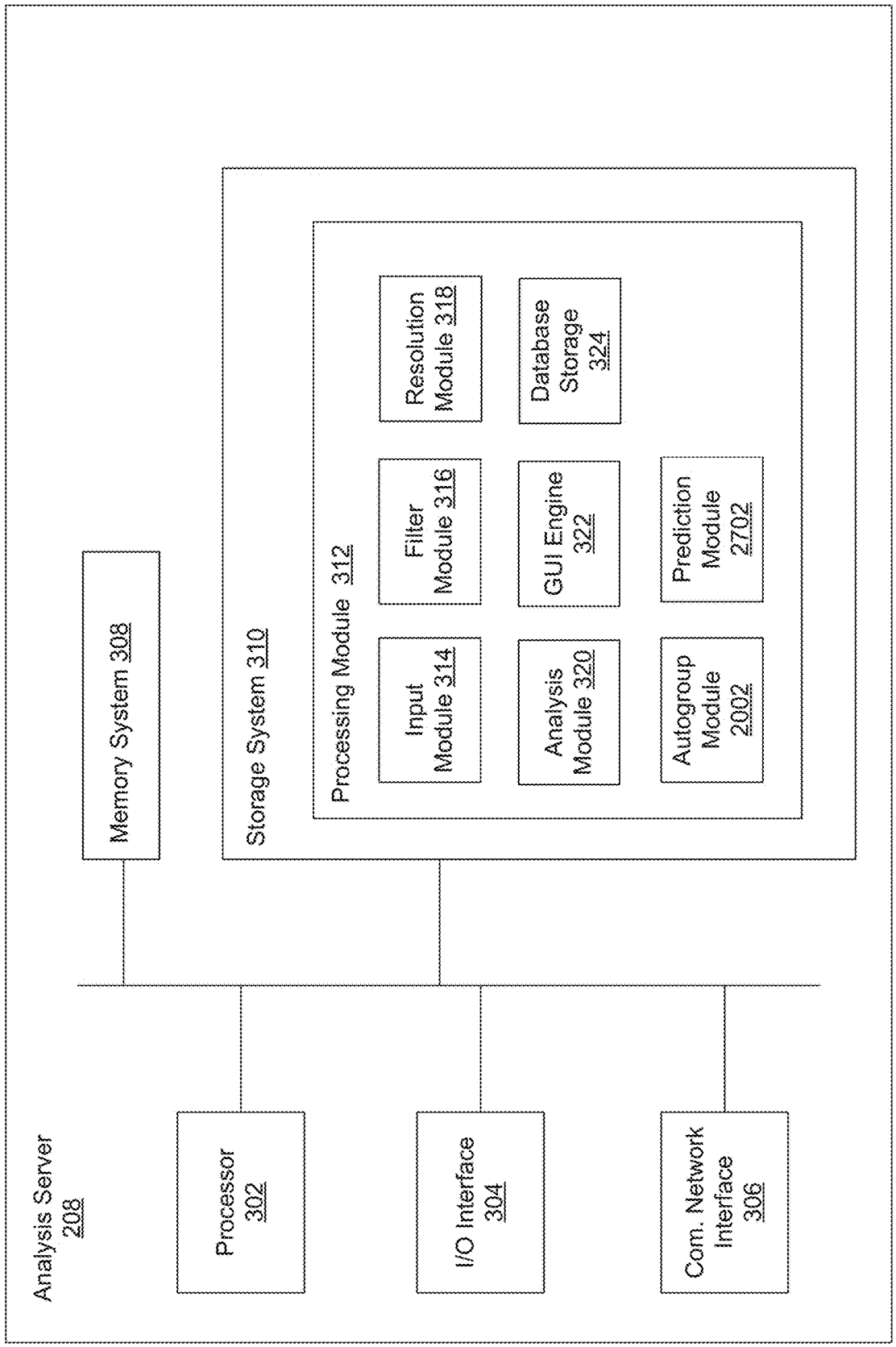
FIG. 27 is a block diagram of an example analysis server 208 including an autogroup module and a prediction module in some embodiments.

FIG. 27 is a block diagram of an example analysis server 208 including an autogroup module 2002 and a prediction module 2702. The example analysis server 208 depicted in FIG. 27 may be similar to the example analysis server 208 depicted in FIG. 3 and FIG. 20. In example embodiments, the analysis server 208 comprises a processor 302, input/output (I/O) interface 304, a communication network interface 306, a memory system 308, and a storage system 310.

The storage system 310 comprises a plurality of modules utilized by embodiments of the present invention. A module may be hardware (e.g., an ASIC), software (e.g., including instructions executable by a processor), or a combination of both. In one embodiment, the storage system 310 comprises a processing module 312 which comprises an input module 314, a filter module 316, a resolution module 318, an analysis module 320, a visualization engine (e.g., GUI engine) 322, a database storage 324, an autogroup module 2002, and a prediction module 2702. Alternative embodiments of the analysis server 208 and/or the storage system 310 may comprise more, less, or functionally equivalent components and modules.

The input module 314 may be configured to receive commands and preferences from the user device 202*a*. In various examples, the input module 314 receives selections from the user which will be used to perform the analysis. The output of the analysis may be an interactive visualization, a visualization that is not interactive, or a graph that is not visualized (e.g., the graph may contain the nodes and edges generated as described herein).

The input module 314 may provide the user a variety of interface windows allowing the user to select and access a database, choose fields associated with the database, choose a metric, choose one or more filters, and identify resolution parameters for the analysis. In one example, the input module 314 receives a database identifier and accesses a large multi-dimensional database. The input module 314 may scan the database and provide the user with an interface window allowing the user to identify an ID field. An ID field is an identifier for each data point. In one example, the identifier is unique. The same column name may be present in the table from which filters are selected. After the ID field is selected, the input module 314 may then provide the user with another interface window to allow the user to choose one or more data fields from a table of the database.

Although interactive windows may be described herein, it will be appreciated that any window, graphical user interface, and/or command line may be used to receive or prompt a user or user device 202*a* for information.

The filter module 316 may subsequently provide the user with an interface window to allow the user to select a metric to be used in analysis of the data within the chosen data fields. The filter module 316 may also allow the user to select and/or define one or more filters.

The resolution module 318 may allow the user to select a resolution, including filter parameters. In one example, the user enters a number of intervals and a percentage overlap for a filter.

The analysis module 320 may perform data analysis based on the database and the information provided by the user. In various embodiments, the analysis module 320 performs an algebraic topological analysis to identify structures and relationships within data and clusters of data. It will be appreciated that the analysis module 320 may use parallel algorithms or use generalizations of various statistical techniques (e.g., generalizing the bootstrap to zig-zag methods) to increase the size of data sets that can be processed. The analysis is further discussed in FIG. 8. It will be appreciated that the analysis module 320 is not limited to algebraic topological analysis but may perform any analysis.

The visualization engine 322 generates an interactive visualization including the output from the analysis module 320. The interactive visualization allows the user to see all or part of the analysis graphically. The interactive visualization also allows the user to interact with the visualization. For example, the user may select portions of a graph from within the visualization to see and/or interact with the underlying data and/or underlying analysis. The user may then change the parameters of the analysis (e.g., change the metric, filter(s), or resolution(s)) which allows the user to visually identify relationships in the data that may be otherwise undetectable using prior means. The interactive visualization is further described in FIGS. 9-11.

The database storage 324 is configured to store all or part of the database that is being accessed. In some embodiments, the database storage 324 may store saved portions of the database. Further, the database storage 324 may be used to store user preferences, parameters, and analysis output thereby allowing the user to perform many different functions on the database without losing previous work.

The autogroup module 2002 may be similar to the discussion with regard to FIG. 20. The autogroup module 2002 may be configured to autogroup data points of a data set or nodes in a graph. As discussed herein, the groupings may be approximations of possible maxima of a given scoring function that scores possible partitions of the original data object (e.g., a collection of data points or a collection of nodes of a graph). The autogroup module 2002 may, in some embodiments, perform autogrouping of nodes of a graph (whether a visualization is generated or not). In various embodiments, the autogroup module 2002 may perform autogrouping for reference space open cover generation. The autogroup module 2002 may autogroup any number of data points, sets of data points, representations, and/or the like. The autogroup module 2002 is further discussed in FIG. 21.

The prediction module 2702 may generate prediction machine learning models that may be utilized to predict outcomes based on a data set. For example, the prediction module 2702 may utilize a TDA graph, either visualized or not displayed, to generate a training data set. The training data set may be used in conjunction with a machine learning model to create a prediction model. For example, an initial data set (e.g., comprising a training data set) may be analyzed using TDA to create a TDA graph. It will be appreciated that a TDA graph groups similar data points together (e.g., in nodes and connected nodes). These groups of data points may be used to transform the initial data set (e.g., used to generate the TDA graph) into the training data set by adding information associated with the groups into the initial data set (e.g., "extending" the data set). Machine learning models that typically may not be effective against large, complex data sets on their own may be used in conjunction with the training data set to generate a prediction model. For example, the machine learning model may leverage the groups of similar data points in the training data set to generate improved results.

The prediction module 2702 may be tested using a test data set with known outcomes to assess whether the prediction model output is the same as or similar to known outcomes. Further, the prediction module 2702 may utilize new data to make outcome predictions.

It will be appreciated that that all or part of the processing module 312 may be at the user device 202*a* or the database storage server 206. In some embodiments, all or some of the functionality of the processing module 312 may be performed by the user device 202*a*.

Figure 28:
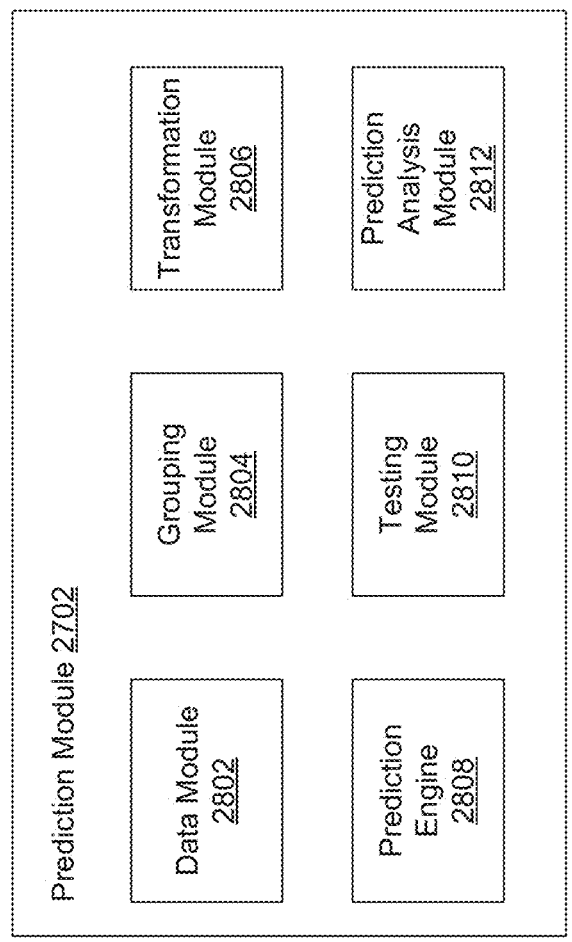
FIG. 28 depicts an example prediction module in some embodiments

FIG. 28 depicts an example prediction module 2702 in some embodiments. A prediction module 2702 may comprise a data module 2802, a grouping module 2804, a transformation module 2806, a prediction engine 2808, a testing module 2810, and a prediction analysis module 2812. The data module 2802 is configured to receive an initial data set.

In some embodiments, the data module 2802 may select a training data set from the initial data set. The data module 2802 may select the training data set in any number of ways. For example, the data module 2802 may select a subset of data points from the initial data set randomly or using any methodology. In some embodiments, all or some of the remaining data points (e.g., unselected data points) may be used to test the prediction model. In various embodiments, the test data set is selected and the training set may be all or some of the remaining data points.

In some embodiments, the training data set may be assessed by the analysis module 320 using TDA described herein and a visualization (e.g., a display) or a graph may be generated. It will be appreciated that a graph may not be displayed. A visualization may depict nodes and edges as described herein. A graph may indicate the nodes and edges described herein but a depiction of a network showing the nodes and edges may not be displayed.

The grouping module 2804 may group data points of the training data set into groups. In some embodiments, the grouping module 2804 may group nodes (e.g., connected nodes of shared data points as well as other nodes with similar data points) of a visualization or graph that was generated using TDA discussed herein together into groups. The grouping module 2804 may group the data points associated with each grouping of nodes into data point groupings. The processing of grouping is further described herein.

Figure 30:
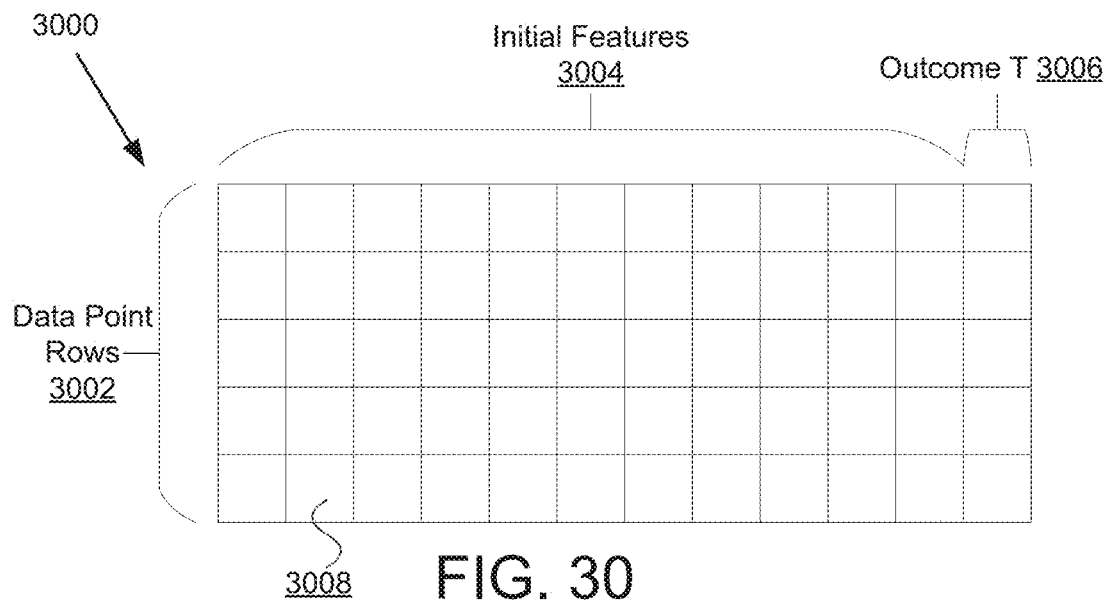
FIG. 30 depicts an example training data set 3000.

One example of a training data set is data matrix X, where the rows are regarded as the individual data points, and the columns are "features". FIG. 30 depicts an example training data set 3000. In some embodiments, the data matrix X (e.g., training data set 3000) may include one or more columns (e.g., outcome T 3006) (which we will denote by "T") that are related to outcome. In one example, the rightmost column in X is an outcome column. In a financial example, the rows might be time points and the columns may be values of economic indicators, and the matrix entries would be the values of the indicators at the given time point. The outcome variable may be the revenue of a business unit at the given time point. X' may denote the matrix X with the column(s) T removed. Each row of the data matrix X may be a data point 3002. Although FIG. 30 shows a limited number of columns and rows, it will be appreciated that there may be any number of rows (e.g., any number of data points) and any number of columns (e.g., any number of features and outcomes). There may be one or more values associated with each data point 3008 (e.g., there may be a value in each row for each column). It will be appreciated that a null or zero is a value. Further, if there is no information for a particular feature of a data point, this may be considered a value.

Figure 31:
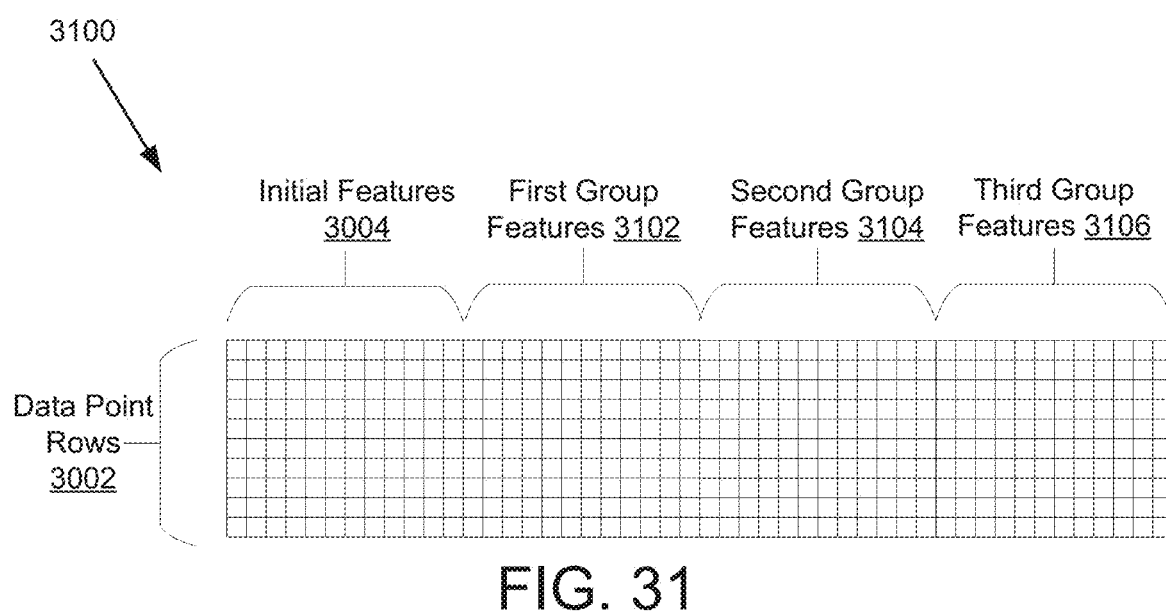
FIG. 31 depicts another example a first transformation data set 3100 in some embodiments.

The transformation module 2806 may generate a new transformation data set based on the training data set using the groups of data points identified by the grouping module 2804. In one example, for each group identified by the grouping module 2804, new sets of features may be added to the training data set. The number of features for each new set of features may be equal to the number of features of the training data set (e.g., which may or may not include outcome T). If a data point is not in the group, than the set of features associated with that group may be zero or null for that data point. If the data point is in the group, the values for the set of features associated with that group may be based on the values of the features of the data point in the training data set. For example, the values of the features of the training data set may be copied into the portion of the new transformation data set associated with the set of features of a particular group. In some embodiments, the values of the features of the training data set may be weighted or modified before being stored in the portion of the new transformation data set associated with the set of features of a particular group. For example, if the data point is in more than one group, the values of the features of the data point in the training data set may be weighted based on membership of multiple groups before being stored in the portion of the new transformation data set associated with the set of features of each particular group that the data point is a member. The weighting may be different for each data point or sets of data points. Data points that are a member of only one group may not, in some embodiments, be weighted before being stored in the portion of the new transformation data set associated with the set of features of a particular group. An example of a transformation data set is depicted in FIG. 31 and is described further herein.

The prediction engine 2808 may generate a prediction model by applying a machine learning model to the transformation data set. The generation of the prediction model is further described herein.

The testing module 2810 may apply the prediction model from the prediction engine 2808 to data (e.g., a testing data set) and compare the output of the prediction model to known outcomes. The testing module 2810 may assess accuracy, similarity, reliability, and the like of the prediction model against known outcomes.

The prediction analysis module 2812 may apply the prediction model from the prediction engine 2808 to any data to generate predicted outcomes. In one example, the prediction analysis module 2812 may receive an analysis data set (e.g., a data set to be analyzed). The analysis data set may include similar or the same features as that in the initial training data set. For each data point in the analysis data set, the predication analysis module 2812 may determine which group (e.g., of the groups identified by the grouping module 2804) to which that data point is a member. The prediction analysis module 2812 may then generate an analysis transformation data set.

As similarly discussed herein, for example, for each group identified by the grouping module 2804, new sets of features may be added to the analysis data set. The number of features for each new set of features may be equal to the number of features of the analysis data set (e.g., which may or may not include outcome T). If a data point is not in the group, than the set of features associated with that group may be zero or null for that data point. If the data point is in the group, the values for the set of features associated with that group may be based on the values of the features of the training data set. For example, the values of the features of the analysis data set may be copied into the portion of the analysis transformation data set associated with the set of features of a particular group. In some embodiments, the values of the features of the analysis data set may be weighted or modified before being stored in the portion of the analysis transformation data set associated with the set of features of a particular group. For example, if the data point is in more than one group, the values of the features of the analysis data set may be weighted based on membership of multiple groups before being stored in the portion of the analysis transformation data set associated with the set of features of each particular group that the data point is a member. The weighting may be different for each data point or sets of data points. Data points that are a member of only one group may not, in some embodiments, be weighted before being stored in the portion of the new transformation data set associated with the set of features of a particular group.

The prediction analysis module 2812 may apply the prediction model to the analysis transformation data set to generate at least one predicted outcome for one or more data point of the analysis transformation data.

Figure 29:
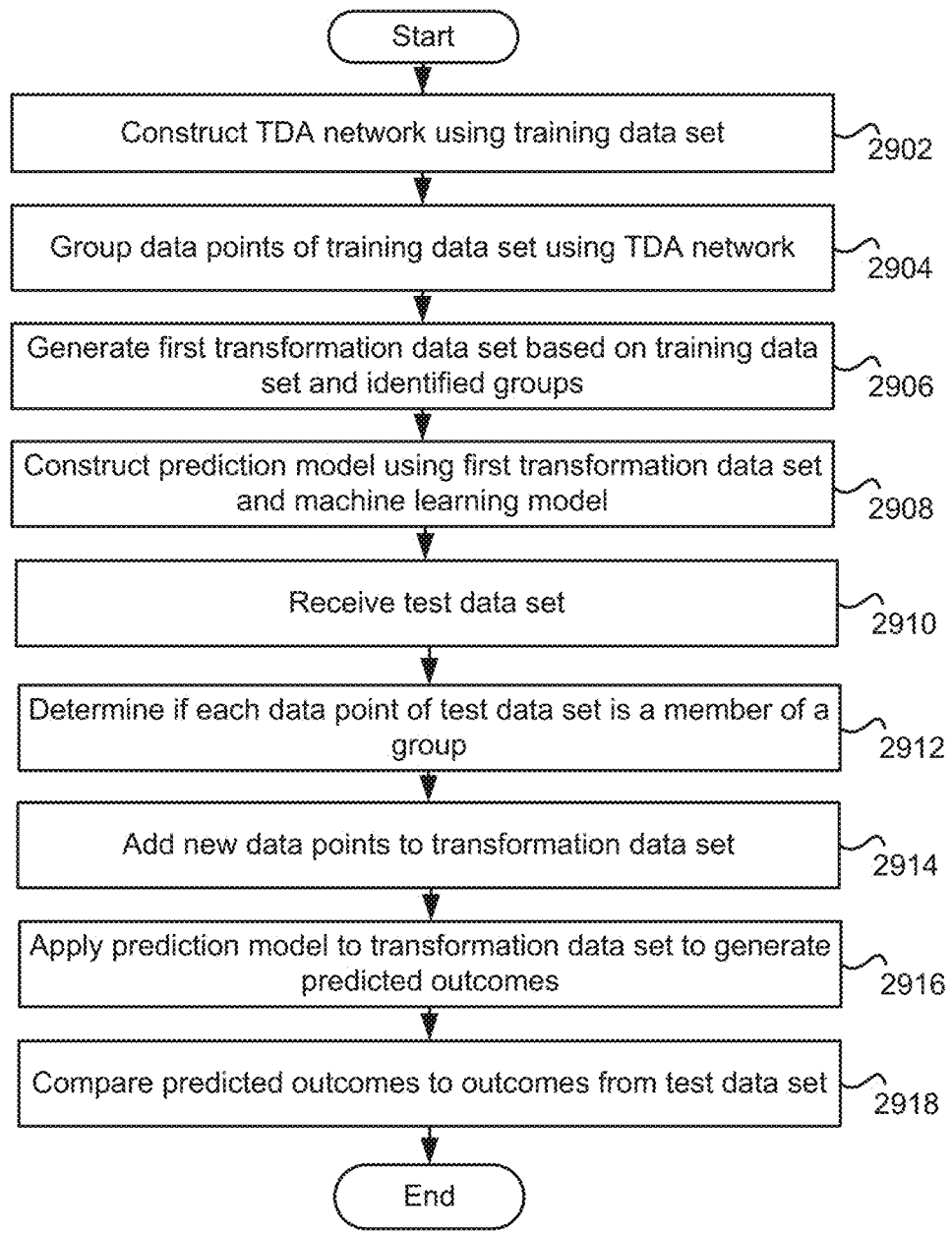
FIG. 29 is a flowchart for creating a prediction model in some embodiments.

FIG. 29 is a flowchart for creating a prediction model in some embodiments. In step 2902, an analysis server 208 constructs a TDA network $\Gamma$ on the rows of X'. The TDA network may be created using systems and methods described herein (e.g., as discussed with regard to FIG. 8). The analysis server 208 may receive a training data set and construct the TDA network $\Gamma$. The choices for metric, lens, resolution, and gain may vary with the kind of data, and may or may not be constructed with the outcome. It will be appreciated that the TDA network $\Gamma$ may or may not be a visualization. Recall that each node corresponds to a set of data points (i.e., a set of rows of X'). For a row $\rho$ and node v, we write $\rho \in v$ when $\rho$ is contained in the collection associated to v.

In step 2904, the grouping module 2804 groups data points of the training data set using the TDA network. For example, the grouping module 2804 may construct a covering of $\Gamma$ (i.e., a finite family $\cup=\{U_\alpha\}_{\alpha \in A}$ of subsets of the set V ($\Gamma$) of vertices of $\Gamma$), so that $$\bigcup_\alpha U_\alpha = V(\Gamma)$$

Grouping may be carried out without reference to any model. In some embodiments, grouping may be carried out by segmentation of the network using autogrouping discussed herein, or it can be carried out by one of outcome based autogrouping approaches based on the outcome being the model error, (i.e. absolute value of the difference between the actual value of the outcome variable and the predicted value using a model).

In step 2906, the transformation module 2806 generates a first transformation data set based on the training data set and the identified groups. In one example, the transformation of the training data set is based on the covering $\cup$.

In one example, for each data point $\rho$ (i.e. row) of X', define $c(\rho)$ to be the number of subscripts a so that $\alpha Åv$ for a node v $ÅU_\alpha$. Note $c(\rho)$ is a positive integer, so is non-zero. We will also totally order the rows into a list $\{\rho_1, \rho_2, \ldots, \rho_M\}$ and the columns into a list $\{\zeta_1, \zeta_2, \ldots, \zeta_N\}$. For any $\alpha ÅA$, and row $\rho$ of X', we define $\varphi_\alpha(\rho)$ to be 0 if $\rho$ is not in v for any $vÅU_\alpha$, and =

$$\frac{1}{c(\rho)}$$

otherwise. We now define, for each $\alpha \in A$, a new matrix $X'(\alpha)=[x'_{ij}(\alpha)]$, where the entry $x'_{ij}(\alpha)$ is defined by:

$$x'_{ij}(\alpha)=\varphi_\alpha(\rho_i)x'_{ij}$$

Note that $X'(\alpha)$ has exactly the same height and width as X'. The transformed data matrix is now obtained as follows. We totally order the set A into a list $\{\alpha_1, \alpha_2, \ldots, \alpha_k\}$, where K=#(A). The transformed matrix will is now obtained by placing each of the matrices $X'(\alpha)$ next to each other, in the total ordering just defined on the $\alpha$'s, and finally append T at the end. So if the original data matrix X was an M x(N+1) matrix, then the transformed matrix is M x(NK+1).

Schematically, the matrix is given as follows.

$$[X'(\alpha_1)|X'(\alpha_2)| \ldots |X'(\alpha_K)|T]$$

This completes the description of the transformation, and we denote it by $R_\cup(X)$. We will also use a second version of the construction, whose matrix is $$[X'|X'(\alpha_1)|X'(\alpha_2)| \ldots |X'(\alpha_K)|T]$$

We have adjoined the original data matrix (with T removed) on the left of $R_\cup(X)$. We will refer to this transform as $\hat{R}_\cup(X)$.

FIG. 31 depicts another example a first transformation data set 3100 in some embodiments. The first transformation data set 3100 may include, for example, data points (e.g., rows 3002) and initial features 3004 (which may or may not include outcome T 3006) of the training data set 3000 depicted in FIG. 31. The first transformation data set 3100 may include additional sets of features for each group. For example, the first transformation data set 3100 may include first group features 3102 which includes a set of features associated with that first group. Similarly, the first transformation data set 3100 may include second group features 3104, third group features 3106, and so on. There may be any number of groups.

In step 2208, the prediction module 2702 constructs a prediction model. In some embodiments, the prediction module 2702 may construct the prediction model based on any modeling scheme which operates on the data consisting of data matrix together with an outcome column. For example, a machine learning model may be applied to the first transformation data set. It will be appreciated that any different machine learning model (or models) may be applied to the first transformation data set. For example, a linear regression machine learning model, polynomial regression machine learning model, logistic regression machine learning model, decision trees machine learning model, or random forest machine learning model may be applied as further discussed herein.

This is a new data matrix, so any modeling method which produces models from data matrices with outcome column can be applied to it, and a new prediction model is obtained. Certain kinds of predictive methods have an additional property, namely that it is provable that the least squares error of the transformed matrix is less than or equal to the least squares error of the original matrix. There are a number of methods that qualify.

Linear regression: Standard linear regression proceeds by defining a feasible space, consisting of all possible linear combinations of the columns, on which the norm of the difference between a linear combination of the columns and the outcome column is minimized.

Noting the property that $\Sigma_{\alpha \bar{A} A} \varphi_\alpha$, it is clear that the feasible space for X is included in the feasible space for $R_U(X)$, in such a way that the errors are preserved. It follows that the minimum error for $R_U(X)$ is less than that for X, since all values obtained in computing the minimum error for X occur in the minimization for $R_U(X)$.

Polynomial regression: This same argument may apply when the feasible space is (a) a vector space and (b) contains each of the original columns. So, as is often done, it can be considered that the vector space of all polynomials of degree less than or equal to k, for some fixed positive integer k, in the set of features. This is also a vector space, and it contains all the columns as monomials of degree 1 inside this set. So in this case, the minimum for the original model may be greater than that for the transformed model.

Logistic regression: Logistic regression may be obtained when a function is applied each of the entries of the outcome column, and then linear regression is applied. One example specific function is:

$$\log \frac{p(x)}{1 - p(x)}$$

where it is understood that $0<p(x)<1$. It follows that in this case, too, the error for the original data matrix is greater than or equal to that for RU(X). This generalizes to optimization of L2-norm of the difference a linear combination of the columns to an arbitrary transform of the outcome data. There are a number of situations directly related to logistic regression.

Decision trees, random forest, etc.: When the predictor is not based on an explicit optimization, there may or may not be error improvement by adjoining additional features. However, there may be improvement in these cases as well. Here the original features may be used (e.g., $\hat{R}_U(X)$).

Another example of the steps 2902-2908 are discussed as follows. Some embodiments of prediction include a framework that may be used to build and improve machine learning models. It will be appreciated that some embodiments described herein may operate in a manual or automatic process. An example process includes a workflow that iterates over selected subsets of training data created using topological data analysis (TDA) described herein.

Various examples of a process for prediction may include: 1) methods to find meaningful subsets of points in both automated and manual ways; 2) methods for integrating the subsets in way that improves machine learning models; and/or 3) methods for automating model construction and improvement TDA approaches may be utilized (such as those described herein, for example) to produce topological summaries of point cloud data. The summaries may be created using at least one metric on received data (either structured or unstructured) in conjunction with a set of functions that may be called "lenses." The summaries may take the form of a network or graph (e.g., a visualization as described herein or unvisualized graph) which comprises a collection of nodes and edges, $G=(\{N_i\}, \{E_j\})$, where each edge connects at least two nodes. Each node in the network may represent a cluster of related points (e.g., two or more related points) and edges between nodes may represent points shared between nodes (e.g., an edge between two nodes represents at least one point being a member of both the connected nodes). When a graph or network is a topological summary, the graph or network may be referred to as an Extended Reeb Graph or ERG. The nodes and edges of a graph may not be depicted, in some embodiments.

Groups of nodes may be selected from a graph or network and a union of points in the nodes may be placed in subsets. In some embodiments, groups are formed in two ways: 1) using "community detection" algorithms based on the combinatorial network structure; and 2) using "outcome groups" which are formed using a function in conjunction with the network.

In a network or graph, communities are collections of nodes that contain more edges within the group than to nodes outside of the group. In some embodiments, off-the-shelf community detection algorithms may be used to create groups of nodes from which to create subsets. For example, the Louvain modularity maximization method may be utilized.

In some embodiments of outcome groups, given a function on the nodes of a network or graph, g: $\{N_i\} \rightarrow R$ connected regions of super level sets of this function may be formed. The following description is a method for selecting super level sets for the case that the network or graph is as described herein (e.g., a collection of nodes and edges) and also for smoothing using relative density of the selected nodes in the network or graph. Consider a network or graph $G=(\{N_i\}, \{E_j\})$ formed from point cloud data $X=(X, d)$ where $X=\{p_i\}$ is a finite set of points and d is a metric on X. In G each $N_i$ represents a set of points $N_i=\{p_j\}_{j \bar{A} I N i}$ recall that a given point $p_k$ can be contained in more than one $N_i$. From any function h on X a function on G may be formed by taking the average value of h on $N_i$ $$H(N_i) = \frac{1}{\#N_i} \sum_{p_i \in N_i} h(p_i)$$

Nodes may be identified for where H is statistically higher than would be expected from a random sample of the points of X A permutation on the values of the error function may be initiated, thereby creating a collection of functions $\{h_1, \ldots, h_k\}$. From each of these there may be a corresponding function on the nodes $\{H_1, \ldots, H_K\}$ yielding a vector of values for each node $\{H^1(N_i), \ldots, H^k(N_i)\}$. A set $S_{top}$ may be created by selecting nodes for membership if the actual error function on the node $H(N_i)$ is in the top P percent of permutation test error values $\{H^1(N_i), \ldots, H^k(N_i)\}$. The K and P parameters may be set by a user (e.g., the user considering how sure to be that the node values are statistical outliers), for a typical example K=1000 and P=0.5 percent. In a similar manner, a set $S_{bottom}$ may be created for nodes with statistically low values by consider sub-level sets of the function h. Write S for either $S_{top}$ or $S_{bottom}$.

The following description is how to do relative density smoothing of S in some embodiments. Given a set S in a metric space (X, d) and a density estimator $\delta_{94}$, depending on a parameter σ, it may be determined how much of the local density is from the set S. In one example, a Gaussian kernel is used to define the density at a point pÅX $$\delta_\sigma(p) = \frac{\sum_{q \in X} e^{\frac{-d(p,q)^2}{\sigma^2}}}{\sum_{q,q' \in X} e^{\frac{-d(q,q')^2}{\sigma^2}}}$$

The density induced by S, $\delta_\sigma^2$ may be defined to be:

$$\delta_\sigma^2(p) = \frac{\sum_{q \in S} e^{\frac{-d(p,q)^2}{\sigma^2}}}{\sum_{q \in X, q' \in S} e^{\frac{-d(q,q')^2}{\sigma}}}$$

In this example, the relative density $\Delta_{94}$ (p, S) is the ratio $$\frac{\delta_\sigma^S}{\delta_\sigma}.$$

Holding p and S fixed and letting σ vary may result in the assignment of a function $\Delta_p^S(\sigma)$ to each point of X measuring the local density over a range σ choices. $0 \leq \Delta_p^S(\sigma) \leq 1$ and $\Delta_p^S(\sigma)$ is a monotonically increasing function in σ. The test statistic:

$$\emptyset_s(p) = \int_\sigma \Delta_p^S(\sigma)$$

may measure the relative density independent of the choice of σ. The higher the test statistic the larger higher confidence that the point p is in a region of high relative density. A background empirical distribution for this test statistic may be established by a permutation test on sets $S_i$, i=1 ... K of size #S. Points from S may be added and removed by checking if the test statistic for is in the top P percent according to the empirical distribution. This creates a set S~. In one example, K=1000 and P=0.2%.

For the case of networks or graphs discussed herein, the metric space may be chosen to be the underlying network G with the graph distance as the distance metric. The test statistic may be calculated by doing a Riemann sum with from 12 to the network diameters in step size ½. The connected components of S~, $U_1, \ldots, U_k$ may be identified as groups and subsets may be identified as points in each $U_i$. For the model correction use case given a function to predict $f: X \to R$ and a model $f: X \to R$, this method may be used to find subsets of points where the error function $e(p_i)=f(p_i)-f\sim(p_i)$ is statistically high or low. In particular for model $f\sim$ the average node error function may be formed:

$$H(N_i) = \frac{1}{\#N_i} \sum_{p_i \in N_i} h(p_i)$$

and follow the procedure to find $U_1, \ldots, U_k$.

In some embodiments of using TDA prediction, it is assumed that there is a given metric space (or similarity space) X and an isometric embedding of X in some larger metric space (e.g., $R^n$, equipped with the Euclidean metric) from which points may be drawn on with which to predict values. In various embodiments, there is a given real valued function $f$ on X, with which to approximate with a learned model.

In this example, there is a Euclidean data set X with coordinates $\{x_1, \ldots, x_n\}$, and a function $f: X \to R$. $\Phi = \{\varphi_0, \varphi_1, \ldots, \varphi_{0n}\}$ denotes the set of functions $\{1, x_1, \ldots, x_n\}$. A may be written to consider X as a matrix with points as rows and features as columns. In particular, A may be expressed an m×(n+1) matrix whose entry $a_{ij}$ is the value $\varphi(x_i)$, where j runs through between 0 and n, inclusively. When building a machine learning model, there may be a desire to minimize the difference between the predicted values $f\sim$ and the actual values $f$ of something to be predicted. In some examples, the $L_2$-norm may be taken of the difference $\|\vec{f} - \vec{f}\|^2$ Where $\vec{f}$ is the function $f$ regarded as a vector of length m=#(X)(mut. mut. $f\sim$).

Assuming the given Euclidean data set X as before, with a function $f: X \to R$, but now with a covering $\cup = \{U_\alpha\}_{\alpha \text{Å} A}$. Functions $\varphi_i^\alpha: X \to R$ may be defined by the formula $$\varphi_i^\alpha(x) = O_x \notin U_\alpha$$

$$\varphi_i^\alpha(x) = \frac{\varphi_i(x)}{c(x)}$$

where c(x) denotes the cardinality of the set $\#\{\alpha | x \text{ Å} U_\alpha\}$. Functions $\varphi_0^\alpha$ may form a kind of partition of unity for the data set with given cover. A new matrix is defined $A(\cup)$, which will be a m x t matrix, where t((n+1 #(A)), and where an identification of the set $\Phi x$ A is made with the set of integers $\{1, 2, \ldots, t\}$. The entry of $A(\cup)$ in the i-th row corresponding to the element (j, α) is now equal to $\varphi_j^\alpha(x_i)$, where $x_i$ is the i-th data point in X. $A(\cup)$ may be identified as a $\cup$-localized data matrix.

In some embodiments, a linear regression is used to minimize or reduce an $L_2$-norm of the difference: $A\vec{x} - \vec{f}$ where $\vec{f}$ is the function $f$ regarded as a vector of length m=#(X). The resulting solution gives a linear combination of the functions in $\Phi$.

In various embodiments, a $\cup$-localized linear regression for the set X is the minimizer for $A(\cup)\vec{t} - \vec{f}$ where $\vec{t}$ is a vector of length t, with the entry corresponding to (j, α) being the coefficient of $\varphi_j^\alpha$. A solution to the $\cup$-localized problem may have better performance on the training data.

It will be appreciated that many machine learning modules that can learn from a feature matrix A can be $\cup$-localized by substituting $A(\cup)$ for A in the learning process.

It will be appreciated that coverings may be chosen in many ways. For example, a covering may be chosen using the nodes in a network or graph as described herein as an open covering. In another example, a covering may also be chosen using a network community detection algorithm such as the Louvain method to create node groups to use as open cover. In another example, a covering may be chosen for a existing predictive model $f\sim$ with ground truth $f$, using an error function $e=f\sim-f$ in the relative density method described herein. The subsets $U_1, \ldots, U_k$ found this way may not form a cover of the space X so we augment the list of subsets with $U_0=X$. In another example, a covering may be chosen by allowing a user to select a covering by selecting groups by coloring of a visualization by the same error function as above.

The number of features going into the model may scale linearly with the number of sets in the cover. Depending on the ability to scale, it will be appreciated that, in some embodiments, the number of groups are pared back. In one example of paring back, group may be sorted by total error, mean error, max error or similar characterization of the error in the group. The sorted groups may be added until the maximum number of groups can be achieved.

In some embodiments, to predict new data of new data point, p, coordinates from A are expanded into the ∪-localized coordinates of A(∪). In some embodiments, it is determined which groups $U_1, \ldots, U_k$p belong. Using the original data matrix A, k classifiers are trained in a one-vs-rest manner predicting membership in each $U_1$. The classifiers can be any standard machine learning algorithm such as support vector machines, logistic regression, random forest, gradient boosted forest or a decision tree.

Returning to FIG. 29, the prediction model may be subsequently tested using a test data set containing data points and known outcomes. In step 2910, the testing module 2810 may receive a test data set. The test data set may comprise data points (e.g., rows) and features. The number of features of the test data set may be similar, the same, or different than the number of features of the training data set.

In step 2912, the testing module 2810 determines for each new data point of the test data set if the new data point is a member of one or more of the groups identified by the grouping module 2804. Determining whether a new data point is within one or more of the groups identified by the grouping module 2804 may be done in any number of ways. In some embodiments, the testing module 2810 may train a random forest classifier or any group classifier for each group. For each new point, the testing module 2810 may take output of the random forest classifier or group based classifier to predict which group (if any) that the data point is a member.

In another embodiment, the testing module 2810 may determine positions of data points in the test data set relative to the data points of the training data set and/or groups of data points (e.g., the groups being identified as nodes, groups of nodes, or the groups identified by the grouping module 2804). The process of identifying a position for a new data point relative to a TDA graph and/or groups is further discussed regarding FIG. 32.

In step 2914, the testing module 2810 adds the new data points to the transformation data set. This may be similar to the initial creation of the transformation data set. In one example, recall that for each group identified by the grouping module 2804, new sets of features may be added to the training data set. The number of features for each new set of features may be equal to the number of features of the training data set (e.g., which may or may not include outcome T) and the features of the test data set. If a new data point from the test data set is not in the group, than the set of features associated with that group may be zero or null for that data point. If the new data point from the test data set is in the group, the values for the set of features associated with that group may be based on the values of the features of the new data point from the test data set. For example, the values of the features of the data point in the test data set may be copied into the portion of the new transformation data set associated with the set of features of a particular group. In some embodiments, the values of the features of the data point from the test data set may be weighted or modified before being stored in the portion of the new transformation data set associated with the set of features of a particular group. For example, if the data point is in more than one group, the values of the features of the data point of the test data set may be weighted based on membership of multiple groups before being stored in the portion of the new transformation data set associated with the set of features of each particular group that the data point is a member. The weighting may be different for each data point or sets of data points. Data points that are a member of only one group may not, in some embodiments, be weighted before being stored in the portion of the new transformation data set associated with the set of features of a particular group.

It will be appreciated that, while in some embodiments there may be additions to the transformation data set, there are other embodiments where a new transformation data set may be constructed in a manner as similarly discussed herein.

In step 2916, the testing module 2810 applies the prediction model to the transformation data set to generate predicted outcomes for the new data points from the test data set. In step 2918, the testing module 2810 compares predicted outcomes to one or more outcomes of the test data set to determine similarity or differences.

In various embodiments, the prediction model may be used to analyze data (e.g., not test data). For example, the prediction model may be used to analyze analysis data to generate predicted outcomes. For example, returning to step 2910, the prediction analysis module 2812 may receive an analysis data set. The analysis data set may comprise data points (e.g., rows) and features. The number of features of the analysis data set may be similar, the same, or different than the number of features of the training data set.

In step 2912, the prediction analysis module 2812 determines for each new data point of the analysis data set if the new data point is a member of one or more of the groups identified by the grouping module 2804. Determining whether a new data point is within one or more of the groups identified by the grouping module 2804 may be done in any number of ways. In some embodiments, the prediction analysis module 2812 may train a random forest classifier or any group classifier for each group. For each new point, the prediction analysis module 2812 may take output of the random forest classifier or group based classifier to predict which group (if any) that the data point is a member.

In another embodiment, the prediction analysis module 2812 may determine positions of data points in the analysis data set relative to the data points of the training data set and/or groups of data points (e.g., the groups being identified as nodes, groups of nodes, or the groups identified by the grouping module 2804).

In step 2914, the prediction analysis module 2812 adds the new data points to the transformation data set. This may be similar to the initial creation of the transformation data set. In one example, recall that for each group identified by the grouping module 2804, new sets of features may be added to the training data set. The number of features for each new set of features may be equal to the number of features of the training data set (e.g., which may or may not include outcome T) and the features of the analysis data set. If a new data point from the analysis data set is not in the group, than the set of features associated with that group may be zero or null for that data point. If the new data point from the analysis data set is in the group, the values for the set of features associated with that group may be based on the values of the features of the new data point from the analysis data set. For example, the values of the features of the data point in the analysis data set may be copied into the portion of the new transformation data set associated with the set of features of a particular group. In some embodiments, the values of the features of the data point from the analysis data set may be weighted or modified before being stored in the portion of the new transformation data set associated with the set of features of a particular group. For example, if the data point is in more than one group, the values of the features of the data point of the analysis data set may be weighted based on membership of multiple groups before being stored in the portion of the new transformation data set associated with the set of features of each particular group that the data point is a member. The weighting may be different for each data point or sets of data points. Data points that are a member of only one group may not, in some embodiments, be weighted before being stored in the portion of the new transformation data set associated with the set of features of a particular group.

It will be appreciated that, while in some embodiments there may be additions to the transformation data set, there are other embodiments where a new transformation data set may be constructed in a manner as similarly discussed herein.

In step 2916, the prediction analysis module 2812 applies the prediction model to the transformation data set to generate predicted outcomes for the new data points from the analysis data set.

Further examples of using the prediction analysis module 2812 and/or the prediction model are discussed herein.

Figure 32:
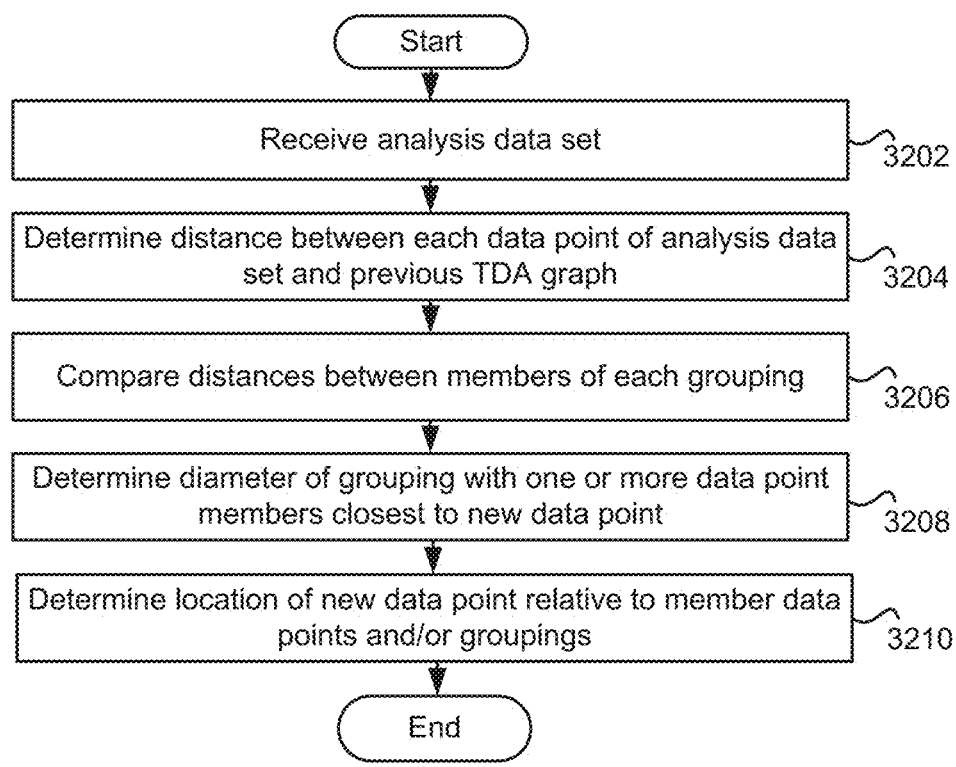
FIG. 32 is a flowchart of for positioning new data relative to a TDA graph in some embodiments.

FIG. 32 is a flowchart of for positioning new data relative to a TDA graph in some embodiments. The process described herein for positioning new data relative to a graph is further described in nonprovisional application Ser. No. 13/648,237, entitled "Systems and Methods for Mapping New Patient Information to Historic Outcomes for Treatment Assistance," filed Oct. 9, 2012, which is incorporated by reference herein. For convenience, financial data will be referred. It will be appreciated that the initial data set used to generate the TDA graph may use any data (e.g., biological data).

In step 3202, an analysis data set containing financial data is received. In various embodiments, an input module 214 of an analysis server (e.g., analysis server 208 of FIGS. 2 and 3) may receive the analysis data set of financial data from a bank, financial entity, regulator, or any other source(s). The financial data may indicate a financial regime, prices, trends, or any other information regarding valuation of or related to any financial vehicle or the like.

In some embodiments, the analysis server 208 may comprise a new data distance module and a location engine. In step 3204, the new data distance module determines distances between the financial data of each point (e.g., row of the analysis data set) and data points of the TDA graph. For example, the previous data that was utilized in the generation of the TDA graph may be stored in mapped data structures. Distances may be determined between the new financial data of each data point and each of the data points previously mapped in the data structure.

It will be appreciated that distances may be determined in any number of ways using any number of different metrics or functions. Distances may be determined between the financial data of the data points in an initial data set (e.g., used in the training data set) and the financial data of the new data points of the analysis data set. For example, a distance may be determined between financial values for a set of features associated with a new data point of the analysis data set and financial values for a set of features associated with a previously existing data point of the training data set. In various embodiments, a location of data point of the analysis data set may be determined relative to other data points of the TDA graph (e.g., from the training data set).

In step 3206, the new data distance module may compare distances between the members of each grouping (e.g., of the groups determined by the grouping module 2804) to the new data point of the analysis data set (or distances determined for the new data point). The new data point may be located in the grouping of previously existing members that are closest in distance to the new data point. In some embodiments, the new point location may be determined to be within a grouping that contains the one or more data points that are closest to the new data point (even if other members of the grouping have longer distances with the new data point). In some embodiments, this step is optional.

In various embodiments, a representative data point may be determined for each grouping. For example, some or all of the data points of a grouping may be averaged or otherwise combined to generate a representative data point member of the grouping (e.g., the distances and/or financial data associated with data points may be averaged or aggregated). Distances may be determined between the new data point of the analysis data set and the averaged or combined financial data of one or more representative data points of the training data set of one or more groupings. The location engine may determine the location of the new data point based on the distances. In some embodiments, once the closest distance between the new data point and the representative data point member is found, distances may be determined between the new data point and the individual data point members of the grouping associated with the closest representative data point member.

In optional step 3208, a diameter of the grouping with the one or more of the data point members that are closest to the new data point (based on the determined distances) may be determined. In one example, the diameters of the groupings of data point members closest to the new data point are calculated. The diameter of the grouping may be a distance between two data point members who are the farthest from each other when compared to the distances between all data point members of the grouping. If the distance between the new data point and the closest data point member of the grouping is less than the diameter of the grouping, the new data point may be located within the grouping. If the distance between the new data point and the closest data point member of the grouping is greater than the diameter of the grouping, the new data point may be outside the grouping (e.g., a new grouping may be identified and/or displayed on a graph with the new data point as the single data point member of the grouping). If the distance between the new data point and the closest data point member of the grouping is equal to the diameter of the grouping, the new data point may be placed within or outside the grouping.

It will be appreciated that the determination of the diameter of the grouping is not required in determining whether the new data point location is within or outside of a grouping. In various embodiments, a distribution of distances between member data points and between member data points and the new data point is determined. The decision to locate the new data point within or outside of the grouping may be based on the distribution. For example, if there is a gap in the distribution of distances, the new data point may be separated from the grouping (e.g., as a new grouping). In some embodiments, if the gap is greater than a preexisting threshold (e.g., established by the user, data scientist, or previously programmed), the new data point may be placed in a new grouping that is placed relative to the grouping of the closest member data points. The process of calculating the distribution of distances of candidate member data points to determine whether there may be two or more groupings may be utilized in generation of a visualization. It will be appreciated that there may be any number of ways to determine whether a new data point should be included within a grouping of other data point members.

In step 3210, the location engine determines the location of the new data point relative to the member data points and/or groupings. The new location may be relative to the determined distances between the new data point and the previous data points. The location of the new data point may be part of a previously existing grouping or may form a new grouping.

Figure 33:
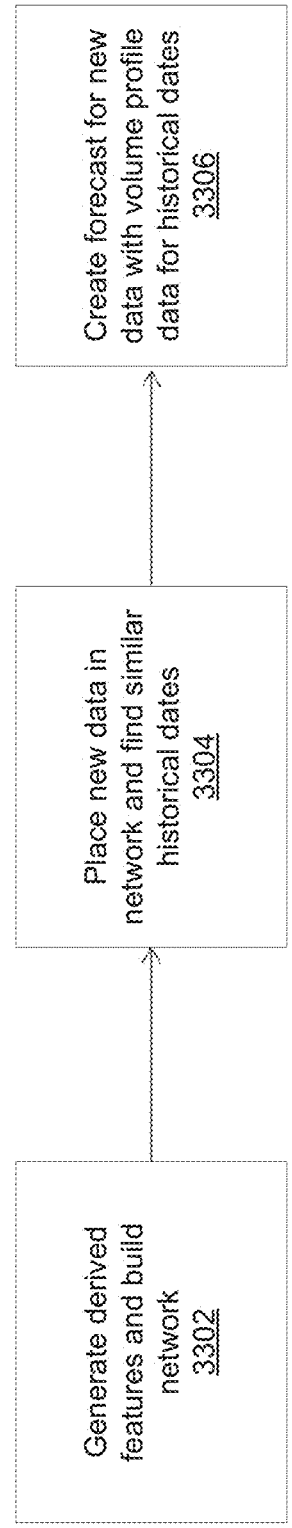
FIG. 33 is a chart regarding a general overview of the following discussed examples.

FIGS. 33-38 related to generating a prediction model and using the prediction models to predict outcomes related to financial data. Although the following embodiments are directed to market conditions analysis and liquidity forecasting, it will be appreciated that any kind of data may be used to create prediction models and/or calculate predicted outcomes using systems and/or methods described herein. FIG. 33 is a chart regarding a general overview of the following discussed examples. For example, derived features may be identified and/or calculated to create a financial data set in step 3302. For example, the data module 2802 may receive financial data to generate the financial data set and/or receive a financial data step. The financial data set may include any financial data including, for example information from and/or about equity indices (e.g., S&P 500, NASDAQ, Euro Stoxx, Nikkei), commodities (e.g., crude oil, natural gas, gold, copper, corn, wheat), yield curves (e.g., US Treasury, AAA Corporate, BAA Corporate), currencies (e.g., Euro, British Pound, Canadian Dollar, Yen, US Dollar), and/or economic data (e.g., unemployment rate, US Dollar Index, and/or other leading indicators).

Figure 35:
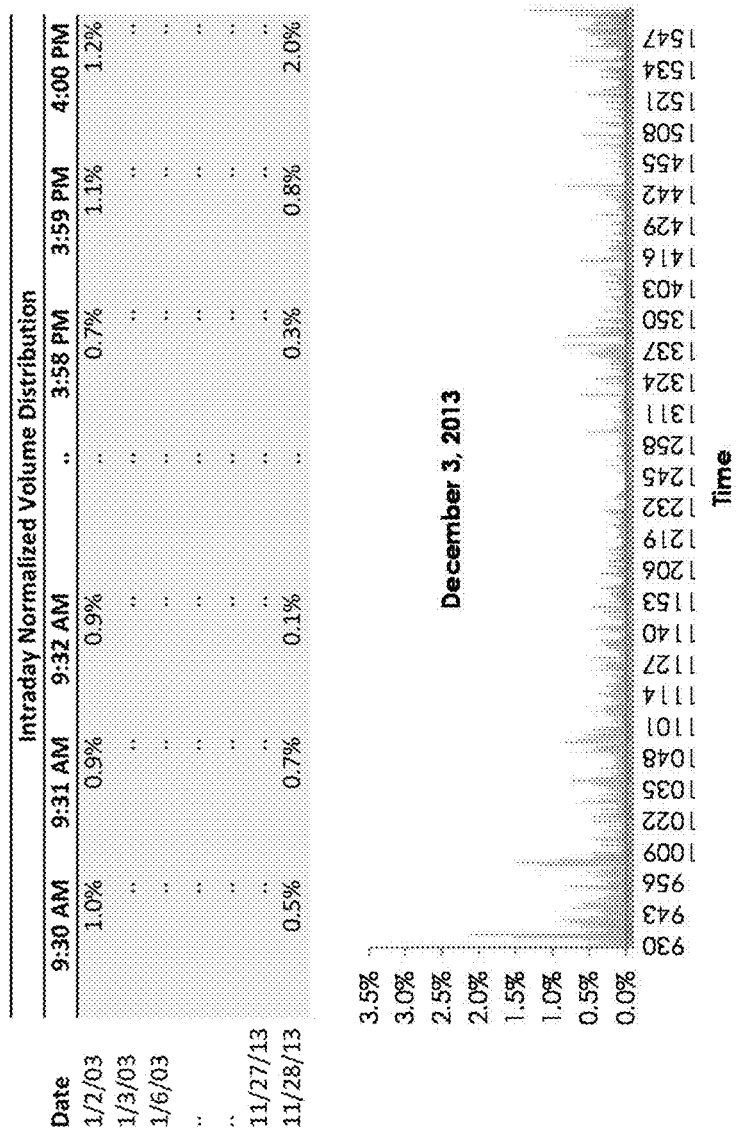
FIG. 35 depicts derived features such as trading volume in this example.

FIG. 34 depicts an example of structure of financial data. In this example, there are 2,600 rows representing 10+ years of daily trading data and 300 features. FIG. 35 depicts derived features such as trading volume in this example. In this example, intraday volume distribution is normalized and this information may be utilized to generate and/or included as features in the financial data set. Trading volume may, in some embodiments, be used as a proxy to measure liquidity. Volumes in each row total 100% and intraday 1 minute volume distribution may show peaks and valleys corresponding to spikes in order flow.

A TDA network may be generated (either visualization or undisplayed graph). The TDA network may then be used to find similar historical dates. In one example, an analysis server 208 constructs a TDA network Γ on the rows of X' of the financial data set. The TDA network may be created using systems and methods described herein (e.g., as discussed with regard to FIG. 8. The choices for metric, lens, resolution, and gain may vary with the kind of data, and may or may not be constructed with the outcome. Each node may correspond to a set of data points (i.e., a set of rows of X'). For a row ρ and node v, we write ρ∈v when ρ is contained in the collection associated to v.

Figure 36:
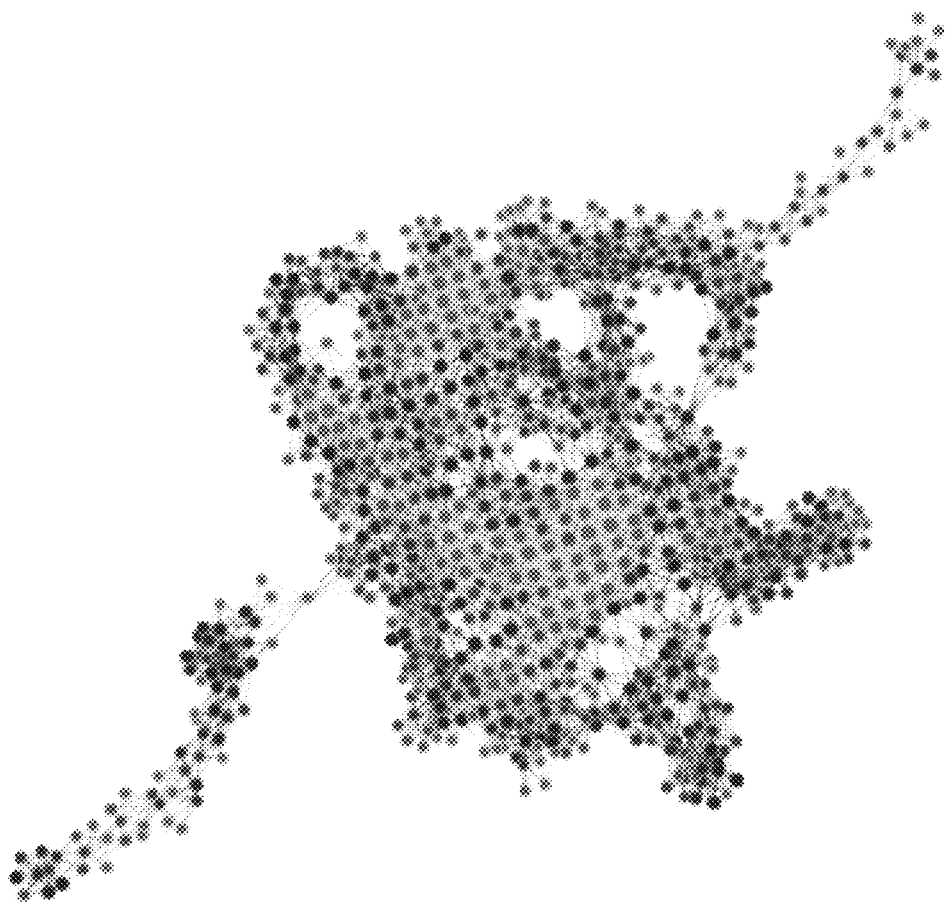
FIG. 36 depicts a TDA network in this example.

FIG. 36 depicts a TDA network in this example.

The grouping module 2804 may groups data points of the financial data set using the TDA network (e.g., using the TDA network depicted in FIG. 36). For example, the grouping module 2804 may construct a covering of Γ (i.e., a finite family $\cup = \{U_\alpha\}_{\alpha \in A}$ of subsets of the set V (Γ) of vertices of Γ), so that $$\bigcup_\alpha U_\alpha = V(\Gamma)$$

Grouping may be carried out without reference to any model. FIG. 34 depicts data that is grouped in similar dates in this example.

As similarly discussed herein, the transformation module 2806 may generates a first transformation data set based on the financial data set and the identified groups. In one example, the transformation of the financial data set is based on the covering ∪. Schematically, the matrix may be as follows.

$$[X'(\alpha_1)|X'(\alpha_2)| \ldots |X'(\alpha_K)|T]$$

A second version of the construction may include the matrix $$[X'|X'(\alpha_1)|X'(\alpha_2)| \ldots |X'(\alpha_K)|T].$$

The prediction module 2702 may construct a prediction model based on any modeling scheme which operates on the data consisting of data matrix. For example, a machine learning model may be applied to the first transformation data set. It will be appreciated that any different machine learning model (or models) may be applied to the first transformation data set. For example, a linear regression machine learning model, polynomial regression machine learning model, logistic regression machine learning model, decision trees machine learning model, or random forest machine learning model may be applied as further discussed herein.

This is a new data matrix, so any modeling method which produces models from data matrices may be applied, and a new prediction model is obtained.

In step 3304 of FIG. 33, new financial data is used to create a financial analysis data set. Previously identified groups (e.g., grouped by similar historical dates) identified by the grouping module 2804 may be utilized to create a second transformation data set. The second transformation data set may include the first transformation data set as well as the information from data points of the financial analysis data set. FIG. 37 depicts groupings of financial data based on similar dates in this example.

For example, the prediction analysis module 2812 may determine for each new data point of the financial analysis data set if the new data point is a member of one or more of the groups identified by the grouping module 2804. Determining whether a new data point is within one or more of the groups identified by the grouping module 2804 may be done in any number of ways as discussed herein.

The transformation module 2806 may add the new data points from the financial analysis data set to the second transformation data set. This may be similar to the initial creation of the first transformation data set. In one example, recall that for each group identified by the grouping module 2804, new sets of features may be added to the training data set. The number of features for each new set of features may be equal to the number of features of the initial data set and the features of the test data set. If a new data point from the financial analysis data set is not in the group, than the set of features associated with that group may be zero or null for that data point. If the new data point from the financial analysis data set is in the group, the values for the set of features associated with that group may be based on the values of the features of the new data point from the financial analysis data set. For example, the values of the features of the data point in the financial analysis data set may be copied into the portion of the new second transformation data set associated with the set of features of a particular group. In some embodiments, the values of the features of the data point from the financial analysis data set may be weighted or modified before being stored in the portion of the new transformation data set associated with the set of features of a particular group. For example, if the data point is in more than one group, the values of the features of the data point of the financial analysis data set may be weighted based on membership of multiple groups before being stored in the portion of the new second transformation data set associated with the set of features of each particular group that the data point is a member. The weighting may be different for each data point or sets of data points. Data points that are a member of only one group may not, in some embodiments, be weighted before being stored in the portion of the new transformation data set associated with the set of features of a particular group.

Figure 38:
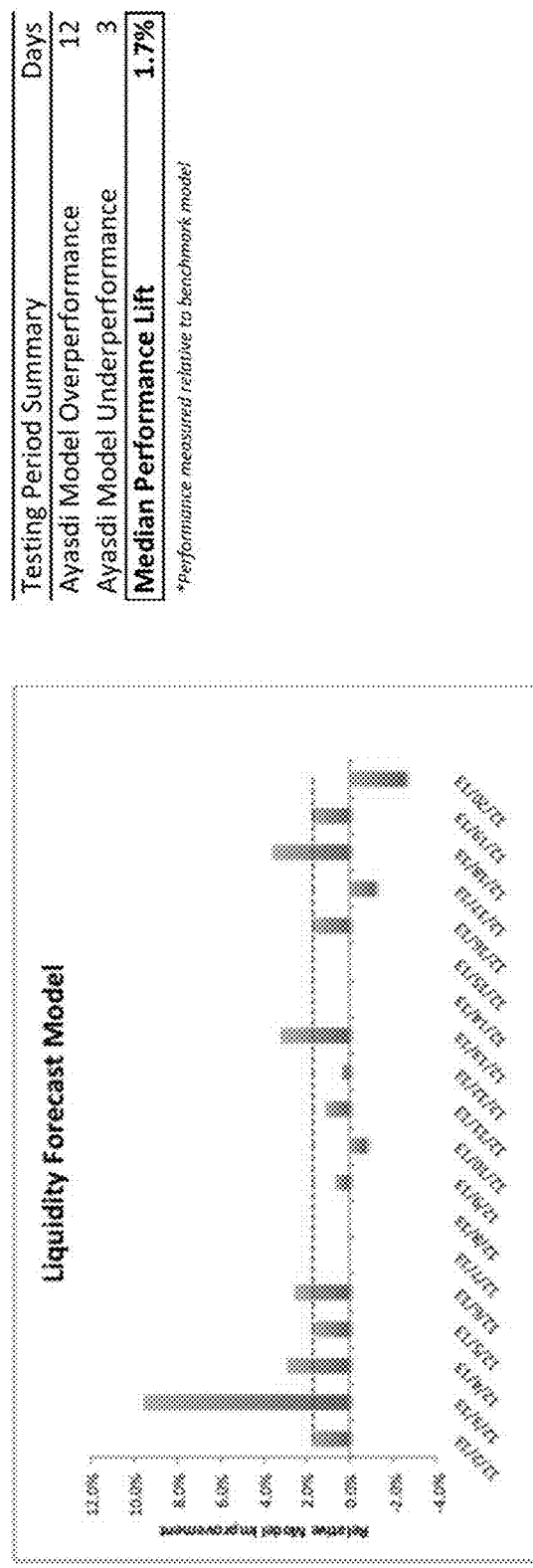
FIG. 38 depicts an output (e.g., predicted outcomes) from the prediction module.

In step 3306 of FIG. 33, a new forecast for new data with volume profile data for historical dates may be created using the prediction model. In one example, the prediction analysis module 2812 may apply the prediction model to the second transformation data set to generate predicted outcomes for the new data points from the financial analysis data set. FIG. 38 depicts an output (e.g., predicted outcomes) from the prediction module.

The predicted outcomes may predict outcomes associated with data from the financial analysis data set. The predicted outcomes may be a report identifying predicted outcomes and/or any information identifying or providing context from the financial analysis data set. In some embodiments, the predicted outcome may be a chart or graph. In various embodiments, the prediction analysis module 2812 may generate messages to provide the predicted outcomes to another digital device or user. It will be appreciated that the predicted analysis module 2812 may compare any or all predicted outcomes to one or more thresholds (e.g., created by a user or digital device) to send messages or alerts when one or more predicted outcomes is greater, lesser, or equal to the one or more outcomes.

The above-described functions and components can be comprised of instructions that are stored on a storage medium (e.g., a computer readable storage medium). The computer readable storage medium may be non-transitory. The instructions can be retrieved and executed by a processor. Some examples of instructions are software, program code, and firmware. Some examples of storage medium are memory devices, tape, disks, integrated circuits, and servers. The instructions are operational when executed by the processor (e.g., a data processing device) to direct the processor to operate in accord with embodiments of the present invention. Those skilled in the art are familiar with instructions, processor(s), and storage medium.

The present invention(s) have been described above with reference to example embodiments. It will be apparent that various modifications may be made and other embodiments can be used without departing from the broader scope of the invention(s). Therefore, these and other variations upon the example embodiments are intended to be covered by the present invention(s).

What is claimed is:

1. A non-transitory computer-readable medium including executable instructions, the instructions being executable by a processor to perform a method, the method comprising:
receiving a network of a plurality of nodes and a plurality of edges, each of the nodes of the plurality of nodes comprising members representative of at least one subset of initial data points, each of the edges of the plurality of edges connecting nodes that share at least one data point of the initial data points, each node of the plurality of nodes being defined by a mapping of the initial data points to a reference space using a distance metric and a location of the initial data points within a set of overlapping open sets within the reference space, each node of the plurality of nodes including at least a subset of the initial data points within one open set of the set of overlapping open sets, distance between two or more of the initial data points being based at least in part on distance between values of feature sets of the two or more of the initial data points, a data point of the initial data points including biological data of a first person, the biological data of the first person representing conditions of the first person;
generating a training data set using the network of the plurality of nodes and the plurality of edges, the training data set including at least a subset of the initial data points that are members of a subset of nodes of the plurality of nodes and at least one feature of a plurality of features of the initial data points based on at least one edge of the plurality of edges between at least two nodes of the plurality of nodes, the training data set including rows and columns, each row defining a data point of the training data set and each column defining at least one of the plurality of features, the training data set including an initial number of columns, each column including values associated with a feature of a plurality of features, the plurality of features representing biological data of persons;
grouping the data points of the training data set into a plurality of groups, each group including data points of the training data set that are members of a set of interconnected nodes of the subset of nodes of the plurality of nodes, each group of the plurality of groups including a different subset of data points of the training data set, each data point of the training data set being a member of at least one group of the plurality of groups, each group of the plurality of groups including the initial data points that are members of a subset of the plurality of nodes;
creating a first transformation data set, the first transformation data set including the training data set as well as a plurality of feature subsets, each of the plurality of feature subsets being associated with at least one group of the plurality of groups, values of a particular data point for a particular feature subset for a particular group being based on values of the particular data point in the training data set if the particular data point is a member of the particular group;
applying a machine learning model to the first transformation data set to generate a prediction model;
receiving an analysis data set, the analysis data set including at least one row and the columns, the at least one row defining at least one data point including biological data of a second person;
grouping the at least one data point of the analysis data set into one or more groups of the plurality of groups;
creating a second transformation data set, the second transformation data set including the analysis data set as well as the plurality of feature subsets, each of the plurality of feature subsets being associated with the at least one group of the plurality of groups, values of a particular data point of the analysis data set for a particular feature subset for a particular group being based on values of the particular data point in the analysis data set if the particular data point is a member of the particular group;

applying the prediction model to the second transformation data set to generate predicted outcomes, the predicted outcomes related to clinical outcomes of the second person; and generating a report indicating one or more of the predicted outcomes related to clinical outcomes of the second person.

2. The non-transitory computer-readable medium of claim 1, the method further comprising comparing the predicted outcomes to known outcomes to assess a quality of the prediction model.

3. The non-transitory computer-readable medium of claim 1, wherein the network of the plurality of nodes and the plurality of edges are a result of topological data analysis applied to the training data set.

4. The non-transitory computer-readable medium of claim 1, wherein values of a particular data point for a particular feature subset for a particular group are zero if the particular data point of the training data set is not a member of the particular group.

5. The non-transitory computer-readable medium of claim 1, wherein values of a particular data point for a particular feature subset for a particular group are null if the particular data point of the training data set is not a member of the particular group.

6. The non-transitory computer-readable medium of claim 1, wherein the values of a particular data point for a particular feature subset for a particular group of which the particular data point is a member are weighted.

7. The non-transitory computer-readable medium of claim 6, wherein weighting of the values for the particular data point at least partially depend on how many the plurality of groups the particular data point is a member of.

8. The non-transitory computer-readable medium of claim 1, wherein the machine learning model is selected from a group consisting of a linear regression machine learning model, a polynomial regression machine learning model, a logistic regression machine learning model, and a random forest machine learning model.

9. A method comprising:
receiving a network of a plurality of nodes and a plurality of edges, each of the nodes of the plurality of nodes comprising members representative of at least one subset of initial data points, each of the edges of the plurality of edges connecting nodes that share at least one data point of the initial data points, each node of the plurality of nodes being defined by a mapping of the initial data points to a reference space using a distance metric and a location of the initial data points within a set of overlapping open sets within the reference space, each node of the plurality of nodes including at least a subset of the initial data points within one open set of the set of overlapping open sets, distance between two or more of the initial data points being based at least in part on distance between values of feature sets of the two or more of the initial data points, a data point of the initial data points including biological data of a first person, the biological data of the first person representing conditions of the first person;

generating a training data set using the network of the plurality of nodes and the plurality of edges, the training data set including at least a subset of the initial data points that are members of a subset of the plurality of nodes and at least one feature of a plurality of features of the initial data points based on at least one edge of the plurality of edges between at least two nodes of the plurality of nodes, the training data set including rows and columns, each row defining a data point of the training data set and each column defining at least one of the plurality of features, the training data set including an initial number of columns, each column including values associated with a feature of a plurality of features, the plurality of features representing biological data of persons;

grouping the data points of the training data set into a plurality of groups, each group including data points of the training data set that are members of a set of interconnected nodes of the subset of nodes of the plurality of nodes, each group of the plurality of groups including a different subset of data points of the training data set, each data point of the training data set being a member of at least one group of the plurality of groups, each group of the plurality of groups including the initial data points that are members of a subset of the plurality of nodes;

creating a first transformation data set, the first transformation data set including the training data set as well as a plurality of feature subsets, each of the plurality of feature subsets being associated with at least one group of the plurality of groups, values of a particular data point for a particular feature subset for a particular group being based on values of the particular data point in the training data set if the particular data point is a member of the particular group;

applying a machine learning model to the first transformation data set to generate a prediction model;

receiving an analysis data set, the analysis data set including at least one row and the columns, the at least one row defining at least one data point including biological data of a second person;

grouping the at least one data point of the analysis data set into one or more groups of the plurality of groups;

creating a second transformation data set, the second transformation data set including the analysis data set as well as the plurality of feature subsets, each of the plurality of feature subsets being associated with the at least one group of the plurality of groups, values of a particular data point of the analysis data set for a particular feature subset for a particular group being based on values of the particular data point in the analysis data set if the particular data point is a member of the particular group;

applying the prediction model to the second transformation data set to generate predicted outcomes, the predicted outcomes related to clinical outcomes of the second person; and generating a report indicating one or more of the predicted outcomes related to clinical outcomes of the second person.

10. The method of claim 9, further comprising comparing the predicted outcomes to known outcomes to assess a quality of the prediction model.

11. The method of claim 9, wherein the network of the plurality of nodes and the plurality of edges are a result of topological data analysis applied to the training data set.

12. The method of claim 9, wherein values of a particular data point for a particular feature subset for a particular group are zero if the particular data point of the training data set is not a member of the particular group.

13. The method of claim 9, wherein values of a particular data point for a particular feature subset for a particular group are null if the particular data point of the training data set is not a member of the particular group.

14. The method of claim 9, wherein the values of a particular data point for a particular feature subset for a particular group of which the particular data point is a member are weighted.

15. The method of claim 14, wherein weighting of the values for the particular data point at least partially depend on how many the plurality of groups the particular data point is a member of.

16. The method of claim 9, wherein the machine learning model is selected from a group consisting of a linear regression machine learning model, a polynomial regression machine learning model, a logistic regression machine learning model, and a random forest machine learning model.

17. A system comprising:
a processor; and
a memory, the memory comprising instructions executable by the processor to perform the steps of:
receiving a network of a plurality of nodes and a plurality of edges, each of the nodes of the plurality of nodes comprising members representative of at least one subset of initial data points, each of the edges of the plurality of edges connecting nodes that share at least one data point of the initial data points, each node of the plurality of nodes being defined by a mapping of the initial data points to a reference space using a distance metric and a location of the initial data points within a set of overlapping open sets within the reference space, each node of the plurality of nodes including at least a subset of the initial data points within one open set of the set of overlapping open sets, distance between two or more of the initial data points being based at least in part on distance between values of feature sets of the two or more of the initial data points, a data point of the initial data points including biological data of a first person, the biological data of the first person representing conditions of the first person;
generating a training data set using the network of the plurality of nodes and the plurality of edges, the training data set including at least a subset of the initial data points that are members of a subset of nodes of the plurality of nodes and at least one feature of a plurality of features of the initial data points based on at least one edge of the plurality of edges between at least two nodes of the plurality of nodes, the training data set including rows and columns, each row defining a data point of the training data set and each column defining at least one of the plurality of features, the training data set including an initial number of columns, each column including values associated with a feature of a plurality of features, the plurality of features representing biological data of persons;
grouping the data points of the training data set into a plurality of groups, each group including data points of the training data set that are members of a set of interconnected nodes of the subset of nodes of the plurality of nodes, each group of the plurality of groups including a different subset of data points of the training data set, each data point of the training data set being a member of at least one group of the plurality of groups, each group of the plurality of groups including the initial data points that are members of a subset of the plurality of nodes;
creating a first transformation data set, the first transformation data set including the training data set as well as a plurality of feature subsets, each of the plurality of feature subsets being associated with at least one group of the plurality of groups, values of a particular data point for a particular feature subset for a particular group being based on values of the particular data point in the training data set if the particular data point is a member of the particular group;
applying a machine learning model to the first transformation data set to generate a prediction model;
receiving an analysis data set, the analysis data set including at least one row and the columns, the at least one row defining at least one data point including biological data of a second person;
grouping the at least one data point of the analysis data set into one or more groups of the plurality of groups;
creating a second transformation data set, the second transformation data set including the analysis data set as well as the plurality of feature subsets, each of the plurality of feature subsets being associated with the at least one group of the plurality of groups, values of a particular data point of the analysis data set for a particular feature subset for a particular group being based on values of the particular data point in the analysis data set if the particular data point is a member of the particular group;
applying the prediction model to the second transformation data set to generate predicted outcomes, the predicted outcomes related to clinical outcomes of the second person; and
generating a report indicating one or more of the predicted outcomes related to clinical outcomes of the second person.

* * * * *